United States Patent
Schalk et al.

(10) Patent No.: US 10,337,031 B2
(45) Date of Patent: Jul. 2, 2019

(54) PRODUCTION OF FRAGRANT COMPOUNDS

(71) Applicant: Firmenich SA, Geneva (CH)

(72) Inventors: Michel Schalk, Geneva (CH); Fabienne Deguerry, Geneva (CH); Pan Li, Hangzhou (CN); Xiufeng He, Shanghai (CN); Qi Wang, Shanghai (CN)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 15/564,671

(22) PCT Filed: Apr. 11, 2016

(86) PCT No.: PCT/CN2016/078956
§ 371 (c)(1),
(2) Date: Oct. 5, 2017

(87) PCT Pub. No.: WO2016/161984
PCT Pub. Date: Oct. 13, 2016

(65) Prior Publication Data
US 2018/0094281 A1    Apr. 5, 2018

(30) Foreign Application Priority Data
Apr. 9, 2015  (WO) ............... PCT/EP2015/057792

(51) Int. Cl.
C12P 5/00     (2006.01)
C12N 9/88     (2006.01)

(52) U.S. Cl.
CPC ............ C12P 5/007 (2013.01); C12N 9/88 (2013.01); C12Y 402/03039 (2013.01); C12Y 402/03079 (2013.01)

(58) Field of Classification Search
CPC .................. C12N 9/88; C12P 5/007
See application file for complete search history.

(56) References Cited

U.S. PATENT DOCUMENTS

| 3,845,132 A | 10/1974 | Ohloff et al. |
| 4,446,651 A | 5/1984 | Spitz, Jr. et al. |
| 7,615,525 B2 | 11/2009 | Goeke |
| 2012/0077722 A1 | 3/2012 | Dilk et al. |

FOREIGN PATENT DOCUMENTS

| WO | WO2005083045 A1 | 9/2005 |
| WO | WO2006014837 A1 | 2/2006 |
| WO | WO2009036067 A2 | 3/2009 |
| WO | WO2010019696 A2 | 2/2010 |
| WO | WO2013064411 A1 | 5/2013 |
| WO | WO2014027118 A1 | 2/2014 |

OTHER PUBLICATIONS

Mercke et al, "Cloning, Expression, and characterization of epi-cedrol synthase . . . ", Archives of Biochemistry and Biophysics, vol. 369, No. 2, 1999, p. 2013-222.
Liu et al., "Extraction and GC-MS analysis of volatile secondary metabolites of Platycladus orientalis", Chinese Wild Plant Resource, 2011, vol. 30(3), p. 51-55 (see abstract).
Liu et al., "GC-MS analysis of essential oils in Chamaecyparis pisifera and Platycladus orientalis", Nonwood Forest Research, 2011, No. 3, vol. 29, p. 88-92 (see abstract).
Ohloff et al., Scent and Chemistry, The Molecular World of Odors, "4.8 Odorants from alpha-cedrene and thujopsene", Verlag Helvetica Chimica Acta, Zurich, 2011, p. 172-178.
Sakamaki et al., "Biotransformation of thujopsene by Caragana chamlagu", Journal of Natural Products, 2001, vol. 64, No. 5, p. 630-631.
Schalk et al., "Toward a biosynthetic route to sclareol and amber odorants", J. of the American Chemical Society, vol. 134, 2012, p. 18900-18903.
Shen et al., "Advances in sesquiterpene synthases cyclases of Artemisia annua", Chinese Journal of Biotechnology, 2007, No. 6, vol. 369, p. 213-222 (see abstract).
Takigawa et al., "Novel allylic oxidation of alpha-cedrene to sec-cedrenol by Rhodococcus strain", Applied and Environmental Microbiology, 1993, vol. 9(5), p. 1336-1341.
Tatusova et al., "BLAST 2 Sequences, a new tool for comparing protein and nucleotide sequences", FEMS, Microbiology Letters, 1999, vol. 174, p. 247-250.
International Search Report and Written Opinion, application PCT/CN2016/078956 dated Jul. 7, 2016.
Abraham W.R et al., "Microbial Hydroxylation of Cedrol and Cedrene", Z Naturforsch,1987, vol. 42c, p. 414-419.
Altschul et al., "Basic Local Alignment Search Tool", J. Mol. Biol., 1990, vol. 215, p. 403-410.
Sell, A Fragrant Introduction to Terpenoid Chemistry, "6.2.4 Cedrol and Cedrene", The Royal Society of Chemistry, 2003, p. 163-170.

(Continued)

Primary Examiner — Tekchand Saidha
(74) Attorney, Agent, or Firm — Armstrong Teasdale LLP

(57) ABSTRACT

Provided herein is an isolated polypeptide from *Juniperus virginiana*, *Platycladus orientalis* 'Beverleyensis' or *Platycladus orientalis* comprising a (+)-cedrol or a (−)-thujopsene synthase. Further provided herein is an isolated nucleic acid molecule from *Juniperus virginiana*, *Platycladus orientalis* 'Beverleyensis' or *Platycladus orientalis* encoding a (+)-cedrol or (−)-thujopsene synthase. Further provided herein are methods of producing (+)-cedrol or (−)-thujopsene.

11 Claims, 12 Drawing Sheets

Specification includes a Sequence Listing.

(56) References Cited

OTHER PUBLICATIONS

Lamare et al., "Microbial transformations 9. biohydroxylation of alpha-cedrene and cedrol", Tetrahedron Letters, vol. 28, No. 50, 1987, p. 6269-6272.
Lamare et al., "Tetrahedron Report No. 276. Bioconversion of sesquiterpenes", Tetrahedron, 1990, vol. 46, No. 12, p. 4109-4132.

- Figure 1 -
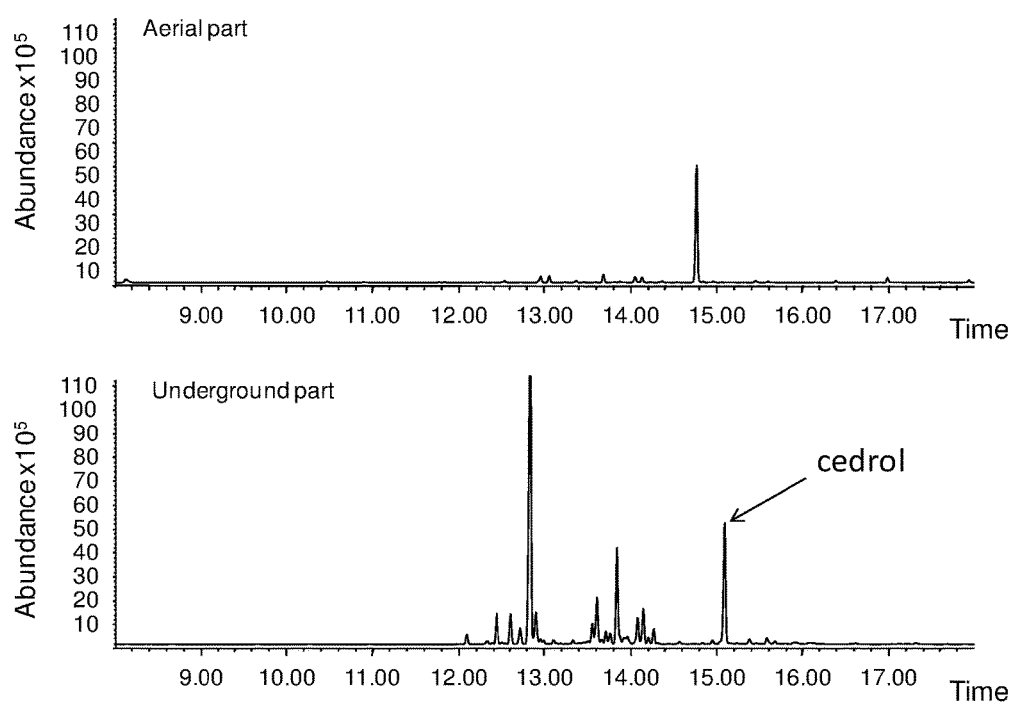

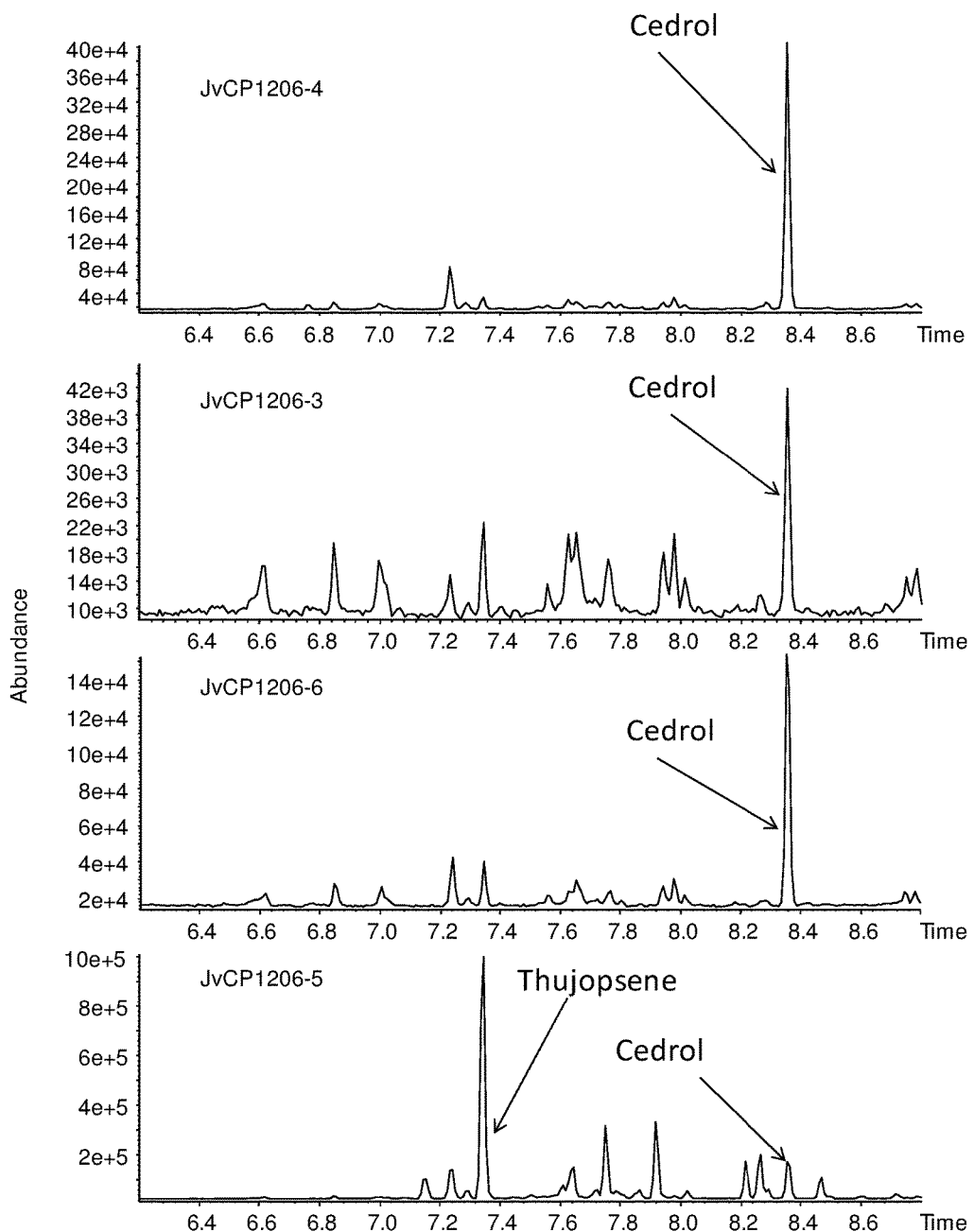
- Figure 2 –

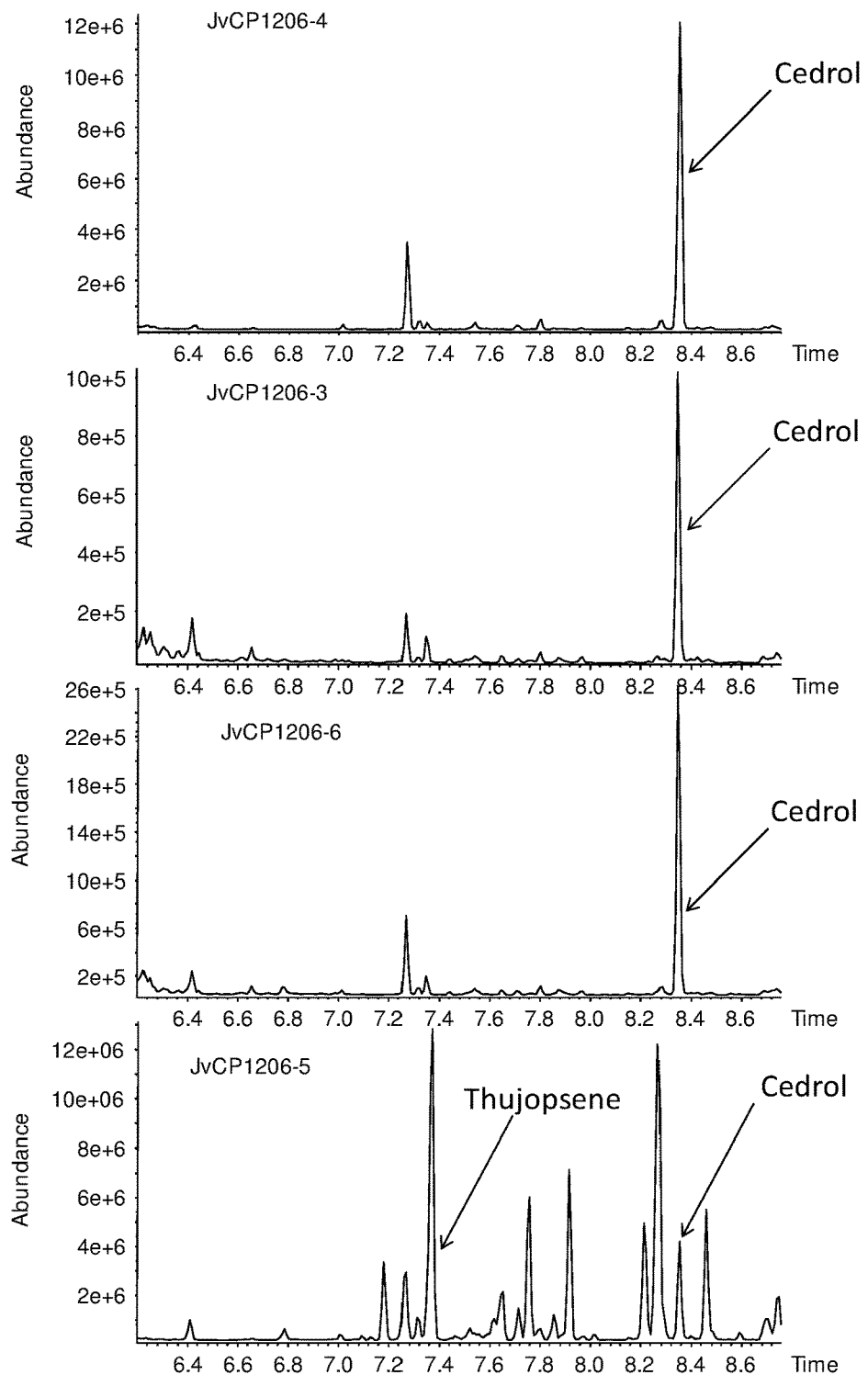
- Figure 3 –

- Figure 4 –
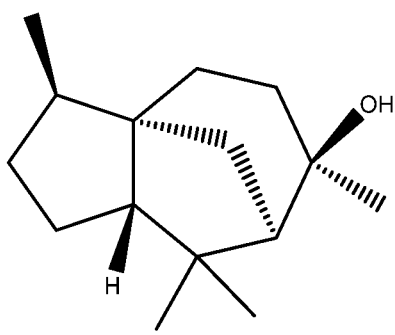
(+)-cedrol
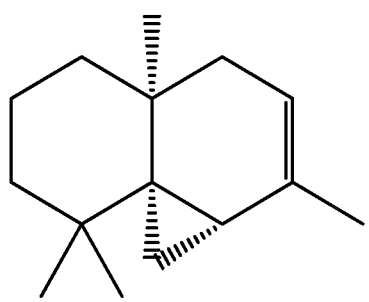
(-)-thujopsene

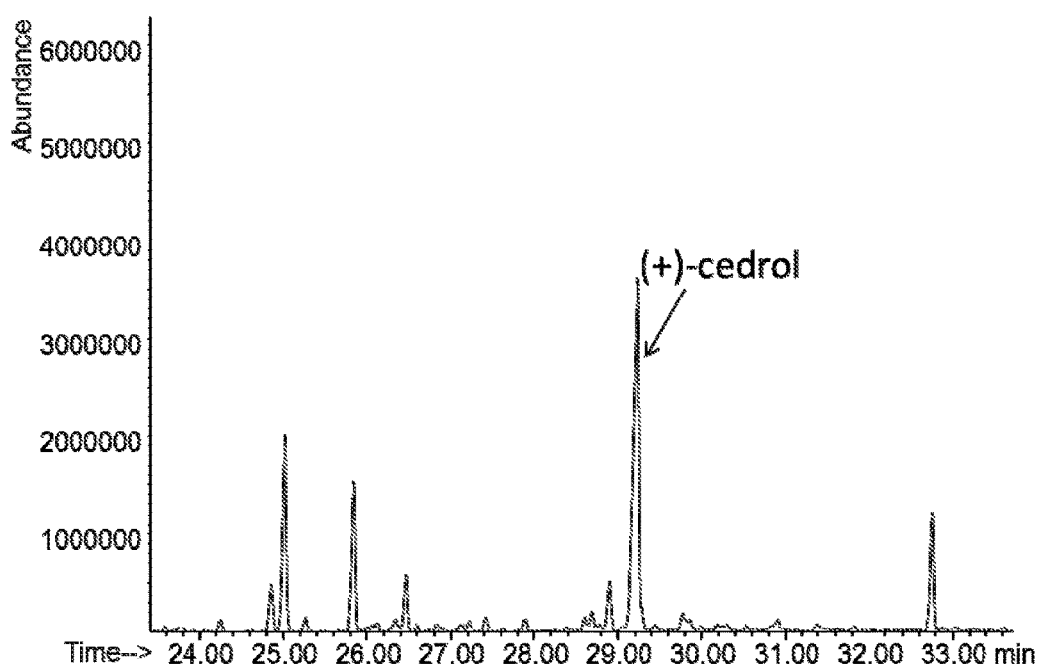
-Figure 5-

-Figure 6-
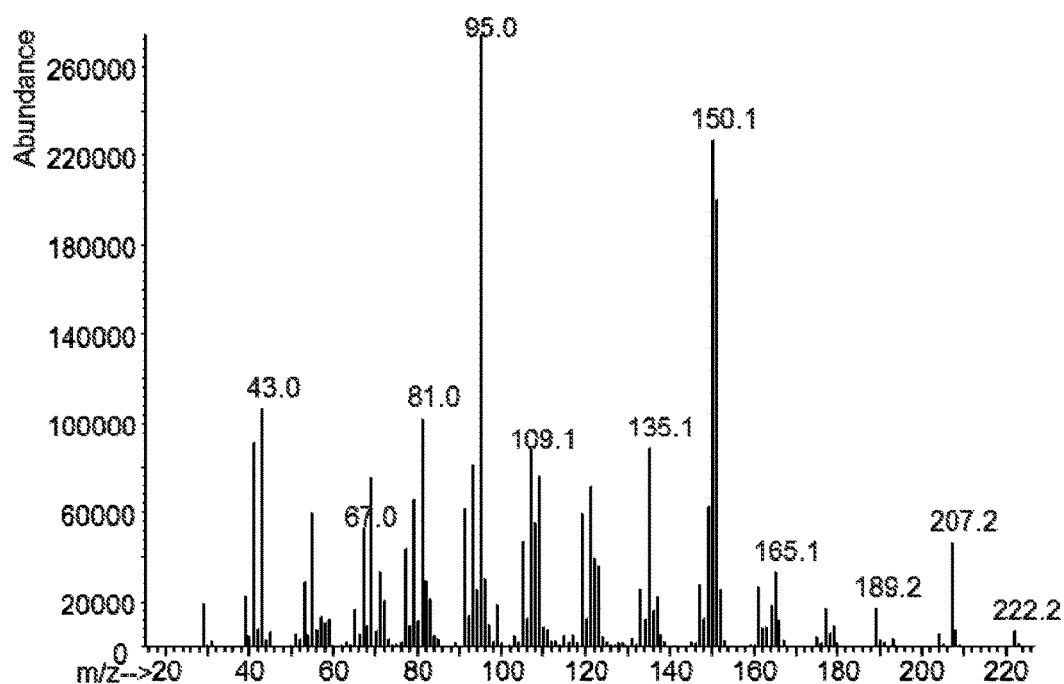

-Figure 7-
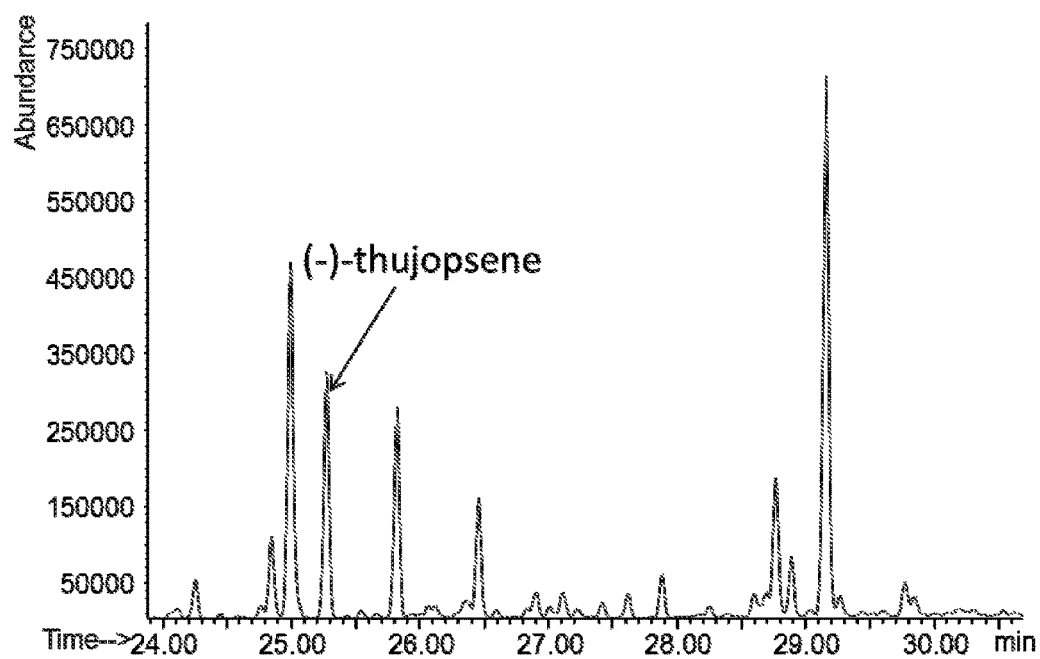

-Figure 8-
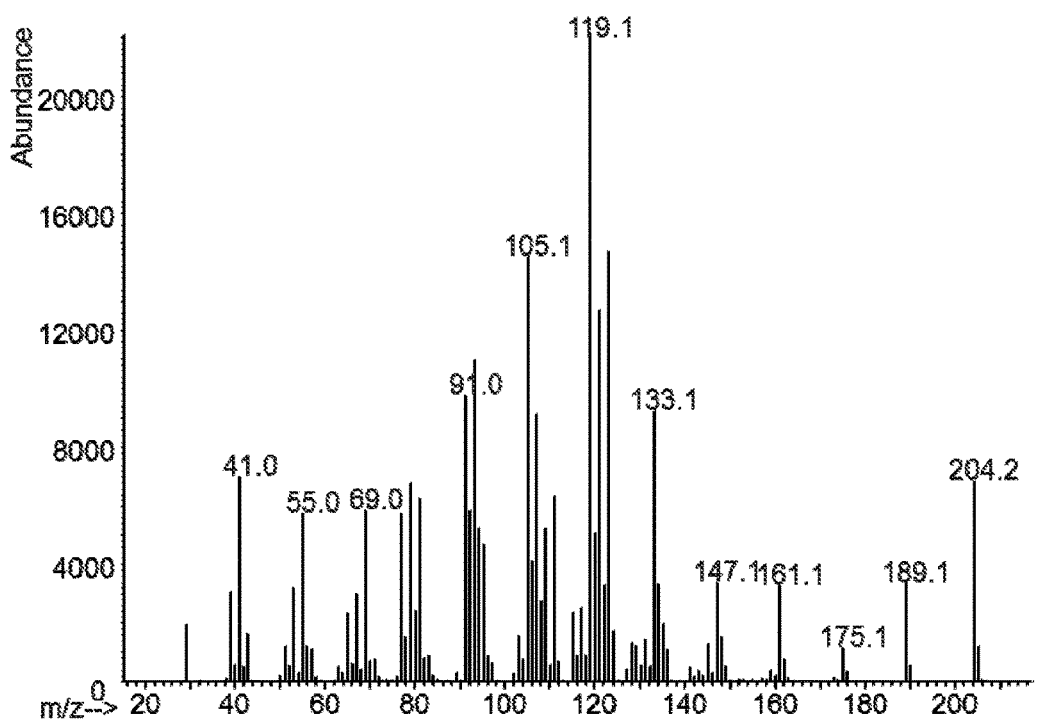

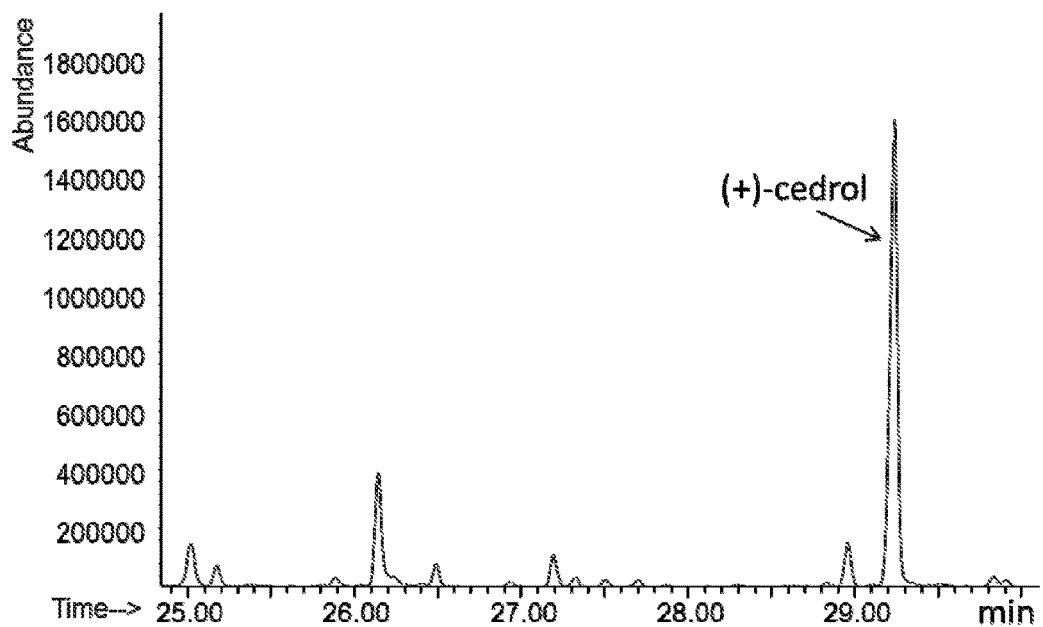
-Figure 9-

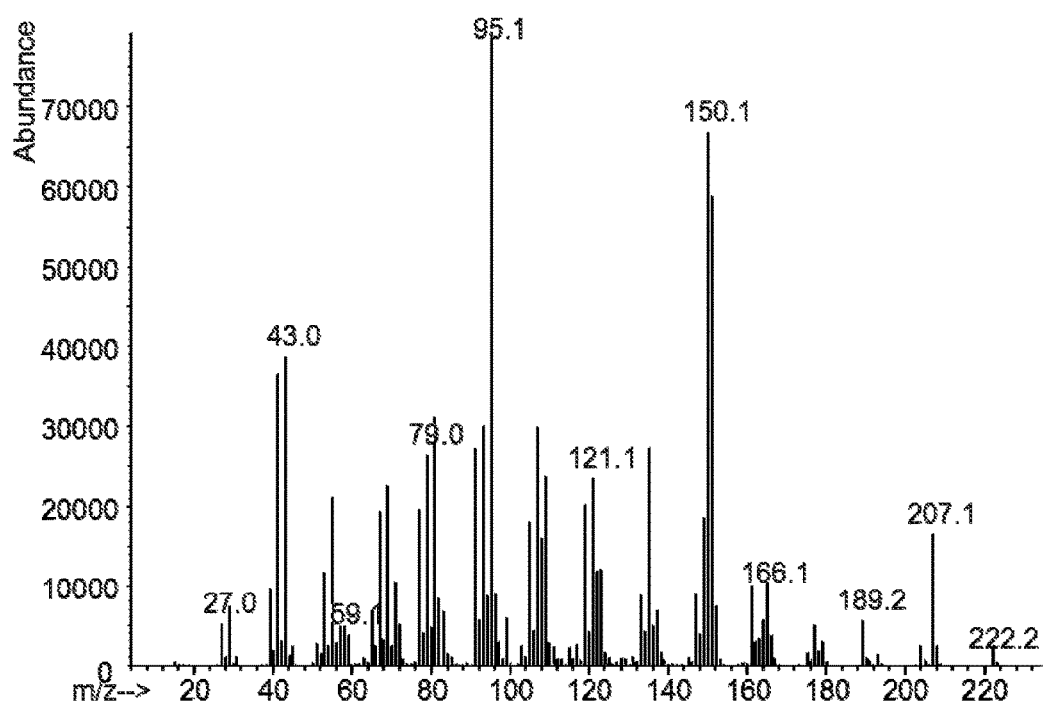
-Figure 10-

-Figure 11-
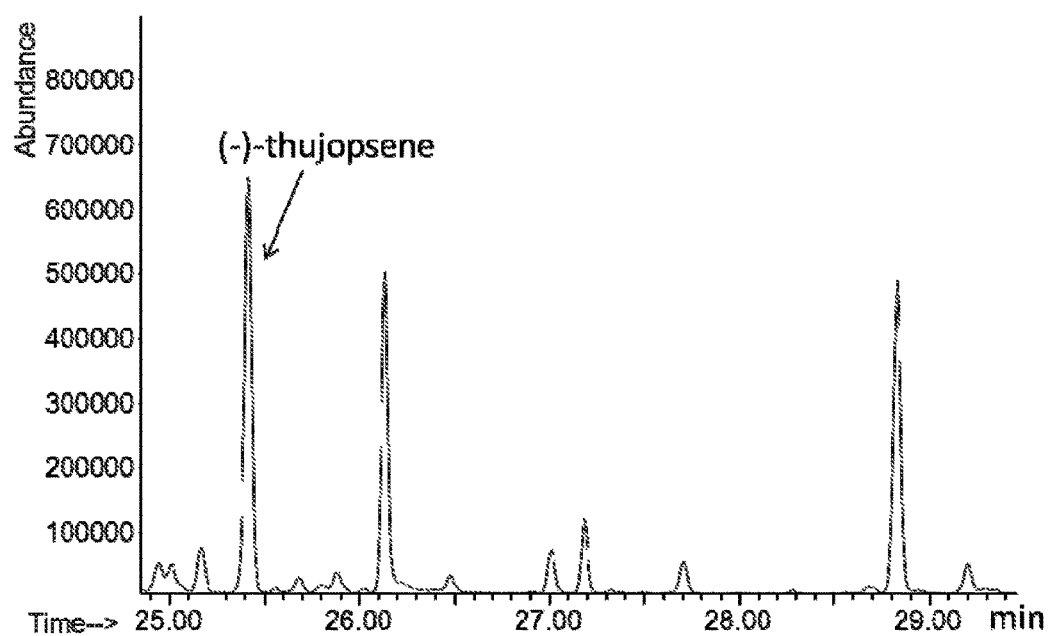

-Figure 12-
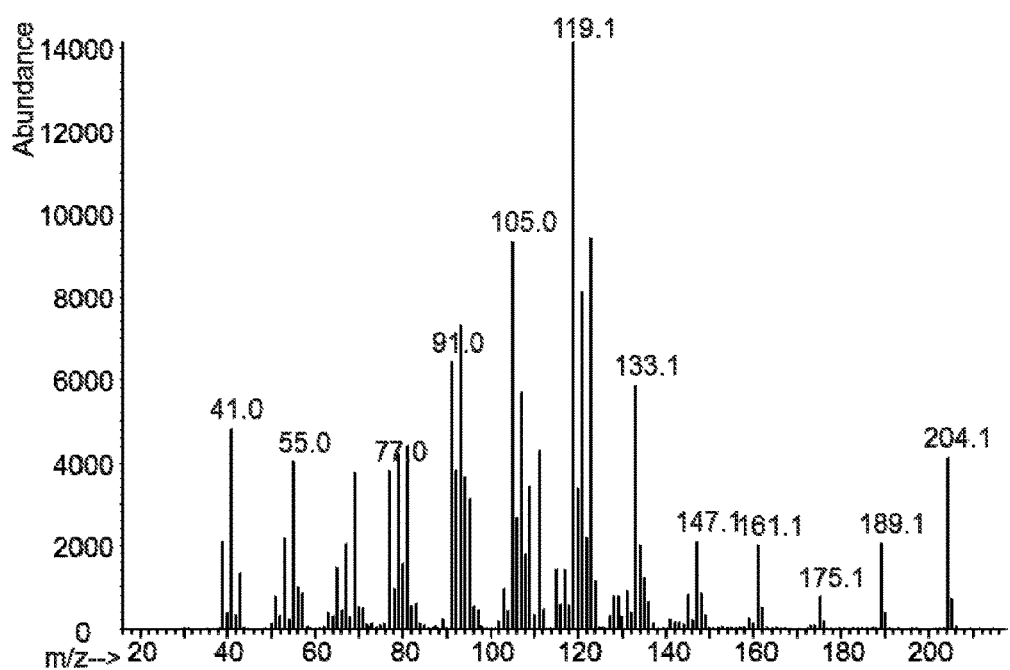

PRODUCTION OF FRAGRANT COMPOUNDS

RELATED APPLICATIONS

This application is a national stage application filing under 35 U.S.C. § 371 of International Patent Application PCT/CN2016/078956, filed Apr. 11, 2016, which claims the benefit of European patent application PCT/EP2015/057792 filed Apr. 9, 2015.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 9340US_SequenceListing. The size of the text file is 62 KB, and the text file was created on Oct. 4, 2017.

TECHNICAL FIELD

The field relates to nucleic acids, enzymes, vectors and cells used in methods to produce terpenes such as (+)-cedrol and (−)-thujopsene.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. Sesquiterpene synthases are present in the plant kingdom and use the substrate farnesyl pyrophosphate (FPP) but they have different product profiles. Genes and cDNAs encoding sesquiterpene synthases have been cloned and the corresponding recombinant enzymes characterized.

Current sources for (+)-cedrol are conifers containing cedar oil. Current sources for (−)-thujopsene are conifers such as *Juniperus cedrus* and *Thujopsis dolabrata*.

SUMMARY

Provided herein is an isolate from *Juniperus virginiana, Platycladus orientalis* 'Beverleyensis' or *Platycladus orientalis* comprising (+)-cedrol or (−)-thujopsene synthase.

Further provided herein is an isolated nucleic acid molecule from *Juniperus virginiana, Platycladus orientalis* 'Beverleyensis' or *Platycladus orientalis* encoding a (+)-cedrol or (−)-thujopsene synthase.

Further provided herein is a method of producing (+)-cedrol or (−)-thujopsene comprising:
a. contacting an acyclic farnesyl diphosphate (FPP) precursor with a polypeptide having an activity selected from the group consisting of a (+)-cedrol synthase activity and a (−)-thujopsene synthase activity wherein the polypeptide comprises:

i. a sequence of amino acids that has at least 70%, 75%, 80%, 85%, 90%, 95%, 98% and/or 99% sequence identity to a polypeptide selected from the group consisting of SEQ ID NO: 1, SEQ ID NO:2, SEQ ID NO:3, SEQ ID NO:4, SEQ ID NO: 13 and SEQ ID NO: 14; or ii. a sequence of amino acids selected from the group consisting of SEQ ID NO:1, SEQ ID NO:2, SEQ ID NO:3, SEQ ID NO:4, SEQ ID NO: 13 and SEQ ID NO: 14;

to produce a compound selected from the group consisting of (+)-cedrol and (−)-thujopsene; and b. optionally isolating the (+)-cedrol and/or the (−)-thujopsene provided that when the polypeptide comprises:

i. a sequence of amino acids that has at least 70%, 75%, 80%, 85%, 90%, 95%, 98% and/or 99% sequence identity to a sequence selected from the group consisting of SEQ ID NO:1, SEQ ID NO:2, SEQ ID NO:3 and SEQ ID NO: 13; or ii. a sequence of amino acids selected from the group consisting of SEQ ID NO:1, SEQ ID NO:2, SEQ ID NO:3 and SEQ ID NO: 13;

the compound produced is (+)-cedrol in the absence of (−)-thujopsene.

Also provided herein is a polypeptide wherein the polypeptide comprises:

a) a sequence of amino acids that has at least 70%, 75%, 80%, 85%, 90%, 95%, 98% and/or 99% sequence identity to a polypeptide selected from the group consisting of SEQ ID NO:1, SEQ ID NO:2, SEQ ID NO:3, SEQ ID NO:4, SEQ ID NO: 13 and SEQ ID NO: 14; or b) a sequence of amino acids selected from the group consisting of SEQ ID NO:1, SEQ ID NO:2, SEQ ID NO:3, SEQ ID NO:4, SEQ ID NO: 13 and SEQ ID NO: 14;

Also provided herein is a nucleic acid encoding a polypeptide described above.

Also provided herein is a nucleic acid comprising:

a. a nucleotide sequence at least 70%, 75%, 80%, 85%, 90%, 95%, 98%, and/or 99% similar or at least 70%, 75%, 80%, 85%, 90%, 95%, 98%, and/or 99% identical to a nucleotide sequence selected from the group consisting of SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO: 15, SEQ ID NO: 16, SEQ ID NO: 17, SEQ ID NO: 18 and SEQ ID NO: 19; or b. a nucleotide sequence selected from the group consisting of SEQ ID NO:5, SEQ ID NO:6, SEQ ID NO:7, SEQ ID NO:8, SEQ ID NO:9, SEQ ID NO: 10, SEQ ID NO: 11, SEQ ID NO:12, SEQ ID NO: 15, SEQ ID NO: 16, SEQ ID NO: 17, SEQ ID NO: 18 and SEQ ID NO: 19.

DESCRIPTION OF THE DRAWINGS

FIG. 1. GCMS analysis of the aerial and underground parts of *Juniperus Virginiana* seedlings (1-2 years-old). The peak of (+)-cedrol is indicated.

FIG. 2. GCMS analysis of the sesquiterpene mixture produce in an in-vitro assay by 4 different *J. virginiana* sesquiterpene synthases, JvCP1206-4, JvCP1206-3, JV1206-6 and JvCP1206-5. The peaks corresponding to (+)-cedrol and (−)-thujopsene are indicated.

FIG. 3. GCMS analysis of the sesquiterpene mixture produce in-vivo by engineered bacteria cells expressing four different *J. virginiana* sesquiterpene synthases, JvCP1206-4, JvCP1206-3, JV1206-6 and JvCP1206-5. The peaks corresponding to (+)-cedrol and (−)-thujopsene are indicated.

FIG. 4. Structure of (+)-cedrol and (−)-thujopsene produced by the recombinant *J. virginiana* sesquiterpene synthases.

FIG. 5. GC/MS chromatogram of *P. orientalis* 'Beverleyensis' leaves dichloromethane extract (only the zone for sesquiterpenes is displayed). The arrow denotes the peak of (+)-cedrol.

FIG. 6. Mass spectrum of the peak of (+)-cedrol in FIG. 5

FIG. 7. GC/MS chromatogram of *P. orientalis* leaves dichloromethane extract (only the zone for sesquiterpenes is displayed). The arrow denotes the peak of (−)-thujopsene.

FIG. 8. Mass spectrum of the peak of (−)-thujopsene in FIG. 7.

FIG. 9. GC/MS chromatogram of the *E. coli* expression experiment of PorB1 (only the zone for sesquiterpene is displayed). Arrow denotes the peak of (+)-cedrol.

FIG. 10. Mass spectrum of the peak of (+)-cedrol in FIG. 9.

FIG. 11. GC/MS chromatogram of the *E. coli* expression experiment of Por2-3-5 (only the zone for sesquiterpene is displayed). Arrow denotes the peak of (−)-thujopsene.

FIG. 12. Mass spectrum of the peak of (−)-thujopsene in FIG. 11.

DETAILED DESCRIPTION

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of.

In one embodiment a method provided herein comprises the steps of transforming a host cell or non-human organism with a nucleic acid encoding a polypeptide having a (+)-cedrol synthase or a (−)-thujopsene synthase activity wherein the polypeptide comprises:
  a. a sequence of amino acids that has at least 70%, 75%, 80%, 85%, 90%, 95%, 98% and/or 99% sequence identity to a polypeptide selected from the group consisting of SEQ ID NO:1, SEQ ID NO:2, SEQ ID NO:3, SEQ ID NO:4, SEQ ID NO: 13 and SEQ ID NO: 14; or
  b. a sequence of amino acids selected from the group consisting SEQ ID NO:1, SEQ ID NO:2, SEQ ID NO:3, SEQ ID NO:4, SEQ ID NO: 13 and SEQ ID NO: 14;
and culturing the host cell or organism under conditions that allow for the production of the polypeptide.

In another embodiment a method provided herein further comprises cultivating a non-human host organism or cell capable of producing FPP and transformed to express a polypeptide wherein the polypeptide comprises:
  a. a sequence of amino acids that has at least 70%, 75%, 80%, 85%, 90%, 95%, 98% and/or 99% sequence identity to a sequence selected from the group consisting of SEQ ID NO:1, SEQ ID NO:2, SEQ ID NO:3, SEQ ID NO:4, SEQ ID NO: 13 and SEQ ID NO: 14; or
  b. a sequence of amino acids selected from the group consisting of SEQ ID NO: 1, SEQ ID NO:2, SEQ ID NO:3, SEQ ID NO:4, SEQ ID NO:13 and SEQ ID NO: 14;
under conditions conducive to the production of (+)-cedrol or (−)-thujopsene.

In another embodiment, provided herein is an expression vector comprising the nucleic acid described herein.

In another embodiment, provided herein is a non-human host organism or cell transformed to harbor at least one nucleic acid described herein so that it heterologously expresses or over-expresses at least one polypeptide described herein.

In one embodiment, the non-human host organism provided herein is a plant, a prokaryote or a fungus.

In one embodiment, the non-human host provided herein is a microorganism, particularly a bacteria or yeast.

In one embodiment, the non-human organism provided herein is *E. coli* and said yeast is *Saccharomyces cerevisiae*.

In one embodiment, the non-human organism provided herein is *Saccharomyces cerevisiae*.

In one embodiment, the cell is a prokaryotic cell.

In another embodiment the cell is a bacterial cell.

In one embodiment the cell is a eukaryotic cell.

In one embodiment the eukaryotic cell is a yeast cell or a plant cell.

In another embodiment a method provided herein further comprising processing the (+)-cedrol to a derivative using a chemical or biochemical synthesis or a combination of both.

In another embodiment a method provided herein further comprising contacting the (+)-cedrol with at least one enzyme to produce a (+)-cedrol derivative.

In another embodiment a method provided herein comprises converting the (−)-thujopsene to a (−)-thujopsene derivative using a chemical or biochemical synthesis or a combination of both.

In another embodiment a method provided herein further comprises contacting the (−)-thujopsene with at least one enzyme to produce a thujopsene derivative.

The ability of a polypeptide to catalyze the synthesis of a particular sesquiterpene (for example a (+)-cedrol synthase and/or a (−)-thujopsene synthase) can be simply confirmed by performing the enzyme assay as detailed in the Examples provided herein.

Polypeptides are also meant to include truncated polypeptides provided that they keep their (+)-cedrol synthase activity and/or their (−)-thujopsene synthase activity.

As intended herein below, a nucleotide sequence obtained by modifying the sequences described herein may be obtained using any method known in the art, for example by introducing any type of mutations such as deletion, insertion or substitution mutations. Examples of such methods are cited in the part of the description relative to the variant polypeptides and the methods to prepare them.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the World Wide Web. Preferably, the BLAST program (Tatiana et al, *FEMS Microbiol Lett.*, 1999, 174:247-250, 1999) set to the default parameters, available from the National Center for Biotechnology Information (NCBI) at http://www.ncbi.nlm.nih.gov/BLAST/bl2seq/wblast2.cgi, can be used to obtain an optimal alignment of peptidic or nucleotidic sequences and to calculate the percentage of sequence identity.

ABBREVIATIONS USED bp base pair
kb kilo base
DNA deoxyribonucleic acid
cDNA complementary DNA
DTT dithiothreitol
FPP farnesyl pyrophosphate
GC gaseous chromatograph
IPTG isopropyl-D-thiogalacto-pyranoside
LB lysogeny broth
MS mass spectrometer
MVA mevalonic acid
PCR polymerase chain reaction
RNA ribonucleic acid
mRNA messenger RNA
miRNA micro RNA
siRNA small interfering RNA
rRNA ribosomal RNA
tRNA transfer RNA

DEFINITIONS

The term "polypeptide" means an amino acid sequence of consecutively polymerized amino acid residues, for instance, at least 15 residues, at least 30 residues, at least 50 residues. In some embodiments provided herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "(+)-cedrol synthase", "(−)-thujopsene synthase", "(+)-cedrol synthase activity", "(−)-thujopsene synthase activity" "(+)-cedrol synthase protein" and "(−)-thujopsene synthase protein" refer to enzymes capable of converting farnesyl diphosphate (FPP) to (+)-cedrol or to (−)-thujopsene.

The terms "biological function," "function," "biological activity" or "activity" refer to the ability of the (+)-cedrol synthase and (−)-thujopsene synthase to catalyze the formation of (+)-cedrol and (−)-thujopsene from FPP.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

An "isolated nucleic acid" or "isolated nucleic acid sequence" is defined as a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which it has not been intentionally modified by a human in the laboratory is naturally occurring.

"Recombinant nucleic acid sequences" are nucleic acid sequences that result from the use of laboratory methods (molecular cloning) to bring together genetic material from more than one source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene, which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein. "Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the host organism or cell, e.g. plant, bacteria or yeast cells, to be transformed. The sequence also may be entirely or partially synthetic. Regardless of the origin, the nucleic acid sequence associated with the promoter sequence will be expressed or silenced in accordance with promoter properties to which it is linked. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of a (+)-cedrol synthase and/or of a (−)-thujopsene synthase in the organism. Particularly, the nucleotide sequence encodes a (+)-cedrol synthase and/or a (−)-thujopsene synthase.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a (+)-cedrol synthase protein or a (−)-thujopsene synthase protein useful to produce (+)-cedrol and/or (−)-thujopsene. The host cell is particularly a bacterial cell, a fungal cell or a plant cell. The host cell may contain a recombinant gene which has been integrated into the nuclear or organelle genomes of the host cell. Alternatively, the host may contain the recombinant gene extrachromosomally. Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related e.g. plant species. Paralogs are found in groups of similar genes using pairwise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

The polypeptide to be contacted with an acyclic pyrophosphate, e.g. FPP, in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a (+)-cedrol synthase activity and/or a (−)-thujopsene synthase activity, either in an isolated form or together with other proteins, for example in a crude protein extract obtained from cultured cells or micro-organisms, may then be suspended in a buffer solution at optimal pH. If adequate, salts, DTT, inorganic cations and other kinds of enzymatic co-factors, may be added in order to optimize enzyme activity. The precursor FPP may be added to the polypeptide suspension, which is then incubated at optimal temperature, for example between 15 and 40° C., particularly between 25 and 35° C., more particularly at 30° C. After incubation, the (+)-cedrol and/or a (−)-thujopsene produced may be isolated from the incubated solution by standard isolation procedures, such as solvent extraction and distillation, optionally after removal of polypeptides from the solution.

According to another particular embodiment, the method of any of the above-described embodiments is carried out in vivo. In one aspect, an embodiment comprises cultivating a non-human host organism or cell capable of producing FPP and transformed to express at least one polypeptide comprising an amino acid sequence at least 70% identical to a sequence selected from the group consisting of SEQ ID NO: 1, SEQ ID NO: 2, SEQ ID NO: 3 SEQ ID NO: 4, SEQ ID NO: 13 and SEQ ID NO: 14 and having a (+)-cedrol synthase activity and/or (−)-thujopsene synthase activity, under conditions conducive to the production of (+)-cedrol and/or (−)-thujopsene.

According to a more particular embodiment, the method further comprises transforming a non-human organism or cell capable of producing FPP with at least one nucleic acid encoding a polypeptide comprising an amino acid sequence at least 70% identical to a sequence selected from the group consisting of SEQ ID NO: 1, SEQ ID NO: 2, SEQ ID NO: 3, SEQ ID NO: 4, SEQ ID NO: 13 and SEQ ID NO: 14 and having a (+)-cedrol synthase activity and/or a (−)-thujopsene synthase activity, so that said organism expresses said polypeptide.

These embodiments provided herein are particularly advantageous since it is possible to carry out the method in vivo without previously isolating the polypeptide. The reaction occurs directly within the organism or cell transformed to express said polypeptide.

According to a more particular embodiment at least one nucleic acid used herein comprises a nucleotide sequence that has been obtained by modifying SEQ ID NO: 5, SEQ ID NO: 6, SEQ ID NO: 7, SEQ ID NO: 8, SEQ ID NO: 9, SEQ ID NO: 10, SEQ ID NO: 11 SEQ ID SEQ ID NO: 12, SEQ ID NO: 15, SEQ ID NO: 16, SEQ ID NO: 17, SEQ ID NO: 18 or SEQ ID NO: 19 or the complement thereof.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art.

To carry out an embodiment herein in vivo, the host organism or cell is cultivated under conditions conducive to the production of a (+)-cedrol synthase and/or a (−)-thujopsene synthase. Accordingly, if the host is a transgenic plant, optimal growth conditions are provided, such as optimal light, water and nutrient conditions, for example. If the host is a unicellular organism, conditions conducive to the production of a (+)-cedrol synthase and/or a (−)-thujopsene synthase may comprise addition of suitable cofactors to the culture medium of the host. In addition, a culture medium may be selected, so as to maximize (+)-cedrol synthase activity and/or a (−)-thujopsene synthase activity. Optimal culture conditions are described in a more detailed manner in the following Examples.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. Most particularly, said bacteria is *E. coli* and said yeast is *Saccharomyces cerevisiae*.

Some of these organisms do not produce FPP naturally or only in small amounts. To be suitable to carry out the method of an embodiment herein, these organisms have to be transformed to produce said precursor or to produce said precursor in larger amounts. They can be so transformed either before the modification with the nucleic acid described according to any of the above embodiments or simultaneously, as explained above.

Isolated higher eukaryotic cells can also be used, instead of complete organisms, as hosts to carry out the method of an embodiment herein in vivo. Suitable eukaryotic cells may be any non-human cell, but are particularly plant or fungal cells.

In another particular embodiment the polypeptide comprises:
c. a sequence of amino acids that has at least 70%, 75%, 80%, 85%, 90%, 95%, 98% and/or 99% sequence identity to a polypeptide selected from the group consisting of SEQ ID NO:1, SEQ ID NO:2, SEQ ID NO:3, SEQ ID NO:4, SEQ ID NO: 13 and SEQ ID NO: 14; or
d. a sequence of amino acids selected from the group consisting of SEQ ID NO:1, SEQ ID NO:2, SEQ ID NO:3, SEQ ID NO:4, SEQ ID NO: 13 and SEQ ID NO: 14.

According to another particular embodiment, the at least one polypeptide having a (+)-cedrol synthase activity and/or a (−)-thujopsene synthase activity used in any of the embodiments described herein or encoded by the nucleic acid described herein comprises an amino acid sequence that is a variant of SEQ ID NO: 1, SEQ ID NO: 2, SEQ ID NO: 3, SEQ ID NO: 4, SEQ ID NO: 13 or SEQ ID NO: 14 obtained by genetic engineering, provided that said variant keeps its (+)-cedrol synthase activity and/or its (−)-thujopsene synthase activity.

As used herein, the polypeptide is intended as a polypeptide or peptide fragment that encompasses the amino acid sequences identified herein, as well as truncated or variant polypeptides, provided that they keep their (+)-cedrol synthase activity and/or a (−)-thujopsene synthase activity as defined above and that they share at least the defined percentage of identity with the corresponding fragment of SEQ ID NO: 1, SEQ ID NO: 2, SEQ ID NO: 3, SEQ ID NO: 4, SEQ ID NO: 13 or SEQ ID NO: 14.

A fragment of a polypeptide described herein may comprise, for example, at least 50%, 60%, 70%, 80%, 90%, 95% or 99% of the polypeptide amino acid sequence described herein.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, encompassed herein are methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of an embodiment herein.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 75%, particularly at least 80%, particularly at least 85%, particularly at least 90%, particularly at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

In a further embodiment, the polypeptide comprises an amino acid sequence at least 80%, particularly at least 85%, particularly at least 90%, particularly at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 85%, particularly at least 90%, particularly at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 90%, particularly at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 95%, particularly at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 98%, and even more particularly at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 99% identical to a sequence selected from the group consisting of SEQ ID NO: 1, SEQ ID NO: 2, SEQ ID NO: 3, SEQ ID NO: 4, SEQ ID NO: 13 and SEQ ID NO: 14.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 1.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 2.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 3.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 4.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 13.

According to a particular embodiment, the polypeptide comprises an amino acid sequence at least 70%, particularly at least 75%, particularly at least 80%, particularly at least 85%, particularly at least 90%, particularly at least 95%, particularly at least 98%, and even more particularly at least 99% identical to SEQ ID NO: 14.

In one aspect, a polypeptide having a (+)-cedrol synthase activity and/or a (−)-thujopsene synthase activity may have a particular selectivity for (+)-cedrol or (−)-thujopsene product when the polypeptide is contacted with FPP as described herein. Selectivity for (+)-cedrol or (−)-thujopsene product as used herein refers to the amount of (+)-cedrol or (−)-thujopsene product produced compared to the total amount of sesquiterpene products, and is typically expressed as a percentage. Selectivity may be given for a particular gene expression system, e.g. an *E. coli* expression system.

In one aspect a polypeptide may produce (+)-cedrol as the major sesquiterpene product. For example, a polypeptide may have a selectivity for (+)-cedrol of about 70-90%, for example, 70% or more, 72% or more, 73% or more, 74% or more, 75% or more, 78% or more, 79% or more, 82% or more, 84% or more, 86% or more or 88% or more. Such selectivities may be obtained, for example, in an *E. coli* expression system such as those described in the present Examples. In one aspect, the polypeptide may produce (+)-cedrol in the absence of (−)-thujopsene.

In one aspect, a polypeptide may produce (−)-thujopsene as the major sesquiterpene product. For example, a polypeptide may have a selectivity for (−)-thujopsene product of about 15-60%, for example, 18% or more, 20% or more, 25% or more, 26% or more, 30% or more, 35% or more, 40% or more, 44% or more, 45% or more, 50% or more, 53% or more, 55% or more, or 57% or more. Such selectivities may be obtained, for example, in an *E. coli* expression system such as those described in the present Examples. In one aspect, the polypeptide may produce (−)-thujopsene in the absence of (+)-cedrol, or may produce (+)-cedrol in addition to (−)-thujopsene but in a lesser amount.

In one aspect, a polypeptide described herein which comprises:
(i) a sequence of amino acids that has at least 70%, 75%, 80%, 85%, 90%, 95%, 98% and/or 99% sequence identity to a sequence selected from the group consisting of SEQ ID NO:1, SEQ ID NO:2, SEQ ID NO:3 and SEQ ID NO: 13; or
(ii) a sequence of amino acids selected from the group consisting of SEQ ID NO: 1, SEQ ID NO:2, SEQ ID NO:3 and SEQ ID NO: 13;

produces (+)-cedrol as the major sesquiterpene product, and may have a selectivity for (+)-cedrol described herein above. Such a polypeptide may produce (+)-cedrol in the absence of (−)-thujopsene.

For example, the PorB1 polypeptide described herein, having the amino acid sequence in SEQ ID NO: 13 can achieve a selectivity for (+)-cedrol of about 88% and in the absence of (−)-thujopsene in an *E. coli* expression system. For example, the JvCP1206-4 polypeptide described herein, having the amino acid sequence in SEQ ID NO: 1 can achieve a selectivity for (+)-cedrol of about 75% and in the absence of (−)-thujopsene in an *E. coli* expression system. For example, the JvCP1206-6 polypeptide described herein, having the amino acid sequence in SEQ ID NO:3 can achieve a selectivity for (+)-cedrol of about 84% and in the absence of (−)-thujopsene in an *E. coli* expression system.

In one aspect, a polypeptide described herein which comprises
(i) a sequence of amino acids that has at least 70%, 75%, 80%, 85%, 90%, 95%, 98% and/or 99% sequence identity to a sequence selected from the group consisting of SEQ ID NO: 4 and SEQ ID NO: 14; or
(ii) a sequence of amino acids selected from the group consisting of SEQ ID NO:4, and SEQ ID NO: 14;

produces (−)-thujopsene as the major sesquiterpene product, and may have a selectivity for (−)-thujopsene described herein above. Such a polypeptide may, for example, produce (−)-thujopsene in the absence of (+)-cedrol, or may produce (+)-cedrol in addition to (−)-thujopsene but in a lesser amount.

For example, the Por2-3-5 polypeptide described herein, having the amino acid sequence in SEQ ID NO: 14 can achieve a selectivity for (−)-thujopsene of about 57% in an *E. coli* expression system. For example, the JvCP1206-5 polypeptide described herein, having the amino acid sequence in SEQ ID NO: 4 can achieve a selectivity for (−)-thujopsene of about 26% in an *E. coli* expression system.

As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 75%, particularly at least 80%, particularly at least 85%, particularly at least 90%, particularly at least 95%, particularly at least 98%, and more particularly at least 99%, identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 80%, particularly at least 85%, particularly at least 90%, particularly at least 95%, more particularly 98% and even more particularly at least 99%, identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 85%, particularly at least 90%, particularly at least 95%, more particularly a least 98% and even more particularly at least 99% identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 90%, particularly at least 95%, more particularly a least 98% and even more particularly at least 99% identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 95%, more particularly a least 98%, and even more particularly at least 99% identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 98% and even more particularly at least 99% identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 99% identical to a sequence selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 5 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 6 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 7 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 8 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 9 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 10 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 11 or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 12, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 15, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 16, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 17, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 18, or the complement thereof.

According to a particular embodiment, the nucleic acid comprises a nucleotide sequence at least 70%, particularly at least 75%, particularly at least 80%, particularly at least 85%, particularly at least 90%, particularly at least 95%, particularly at least 98%, and particularly at least 99%, identical to SEQ ID NO: 19, or the complement thereof.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of an embodiment herein also encompass certain isolated nucleotide sequences including those that are substantially free from contaminating endogenous material. The nucleic acid of an embodiment herein may be truncated, provided that it encodes a polypeptide encompassed herein, as described above.

In one embodiment, the nucleic acid of an embodiment herein can be either present naturally in a plant such as *Juniperus viginiana, Platycladus orientalis* 'Beverleyensis', or *Platycladus orientalis*, or other species, or be obtained by modifying SEQ ID NO: 5, SEQ ID NO: 6, SEQ ID NO: 7, SEQ ID NO: 8, SEQ ID NO: 9, SEQ ID NO: 10, SEQ ID NO: 11 SEQ ID NO: 12, SEQ ID NO: 15, SEQ ID NO: 16, SEQ ID NO: 17, SEQ ID NO: 18 or SEQ ID NO: 19, or the complement thereof.

Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the (+)-cedrol synthase and/or the (−)-thujopsene synthase may be optimized for increased expression in the host cell. For example, nucleotides of an embodiment herein may be synthesized using codons particular by a host for improved expression.

Another important tool for transforming host organisms or cells suitable to carry out the method of an embodiment herein in vivo is an expression vector comprising a nucleic acid according to any embodiment of an embodiment herein. Such a vector is therefore also provided herein.

The expression vectors provided herein may be used in the methods for preparing a genetically transformed host organism and/or cell, in host organisms and/or cells harboring the nucleic acids of an embodiment herein and in the methods for making polypeptides having a (+)-cedrol synthase activity and a (−)-thujopsene synthase activity, as disclosed further below.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and cells are therefore also provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods provided herein. Particularly useful plants are those that naturally produce high amounts of terpenes.

In a more particular embodiment the non-human host organism is a microorganism. Any microorganism is suitable to be used herein, but according to an even more particular embodiment said microorganism is a bacteria or yeast. Most particularly, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

A variant may also differ from the polypeptide of an embodiment herein by attachment of modifying groups which are covalently or non-covalently linked to the polypeptide backbone. The variant also includes a polypeptide which differs from the polypeptide described herein by introduced N-linked or O-linked glycosylation sites, and/or an addition of cysteine residues. The skilled artisan will recognize how to modify an amino acid sequence and preserve biological activity.

The functionality or activity of any (+)-cedrol synthase and/or a (−)-thujopsene synthase protein, variant or fragment, may be determined using various methods. For example, transient or stable overexpression in plant, bacterial or yeast cells can be used to test whether the protein has activity, i.e., produces (+)-cedrol and/or (−)-thujopsene from the FPP precursors. A (+)-cedrol synthase activity and/or a (−)-thujopsene synthase activity may be assessed in a microbial expression system, such as an assay described in the Examples provided herein.

An embodiment herein provides polypeptides of an embodiment herein to be used in a method to produce (+)-cedrol and/or a (−)-thujopsene by contacting an FPP precursor with the polypeptides of an embodiment herein either in vitro or in vivo.

Provided herein is also an isolated, recombinant or synthetic polynucleotide encoding a polypeptide or variant polypeptide provided herein.

Embodiments provided herein include, but are not limited to cDNA, genomic DNA and RNA sequences. Any nucleic acid sequence encoding the (+)-cedrol synthase and/or the (−)-thujopsene synthase or variants thereof is referred herein as a (+)-cedrol synthase and/or a (−)-thujopsene synthase encoding sequence.

It is clear to the person skilled in the art that genes, including the polynucleotides of an embodiment herein, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermostable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

Provided herein are nucleic acid sequences obtained by mutations of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 15, SEQ ID NO: 16, SEQ ID NO: 17, SEQ ID NO: 18 or SEQ ID NO: 19; such mutations can be routinely made. It is clear to the skilled artisan that mutations, deletions, insertions, and/or substitutions of one or more nucleotides can be introduced into these DNA sequence To test a function of variant DNA sequences according to an embodiment herein, the sequence of interest is operably linked to a selectable or screenable marker gene and expression of the reporter gene is tested in transient expression assays with protoplasts or in stably transformed plants. The skilled artisan will recognize that DNA sequences capable of driving expression are built as modules. Accordingly, expression levels from shorter DNA fragments may be different than the one from the longest fragment and may be different from each other. Further provided herein are also functional equivalents of the nucleic acid sequence coding the (+)-cedrol synthase and/or the (−)-thujopsene synthase proteins, i.e., nucleotide sequences that hybridize under stringent conditions to the nucleic acid sequence of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID SEQ ID NO: 12, SEQ ID NO: 15, SEQ ID NO: 16, SEQ ID NO: 17, SEQ ID NO: 18 or SEQ ID NO: 19.

The skilled artisan will be aware of methods to identify homologous sequences in other organisms and methods (identified in the Definition section herein) to determine the percentage of sequence identity between homologous sequences.

An alternative embodiment provided herein provides a method to alter gene expression in a host cell. For instance, the polynucleotide of an embodiment herein may be enhanced or overexpressed or induced in certain contexts (e.g. following insect bites or stings or upon exposure to a certain temperature) in a host cell or host organism.

Alteration of expression of a polynucleotide provided herein also results in "ectopic expression" which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, several (+)-cedrol synthase and/or a (−)-thujopsene synthase encoding nucleic acid sequences are co-expressed in a single host, particularly under control of different promoters. Alternatively, several (+)-cedrol synthases and/or (−)-thujopsene synthases protein encoding nucleic acid sequences can be present on a single transformation vector or be co-transformed at the same time using separate vectors and selecting transformants comprising both chimeric genes.

The nucleic acid sequences of an embodiment herein encoding (+)-cedrol synthase and/or (−)-thujopsene synthase proteins can be inserted in expression vectors and/or be contained in chimeric genes inserted in expression vectors, to produce (+)-cedrol synthase and/or a (−)-thujopsene synthase proteins in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

An embodiment provided herein provides recombinant expression vectors comprising a nucleic acid encoding for a (+)-cedrol synthase and/or a (−)-thujopsene synthase, or a chimeric gene comprising a nucleic acid sequence encoding for a (+)-cedrol synthase and/or a (−)-thujopsene synthase, operably linked to associated nucleic acid sequences such as, for instance, promoter sequences.

Alternatively, the promoter sequence may already be present in a vector so that the nucleic acid sequence which is to be transcribed is inserted into the vector downstream of the promoter sequence. Vectors are typically engineered to have an origin of replication, a multiple cloning site, and a selectable marker.

In one aspect, (+)-cedrol and (−)-thujopsene may be purified from synthase products.

The (+)-cedrol and (−)-thujopsene produced by any of the methods described herein can be converted to derivatives such as, but not limited to hydrocarbons, esters, amides, glycosides, ethers, epoxides, aldehydes, ketons, alcohols, diols, acetals or ketals.

The (+)-cedrol and (−)-thujopsene derivatives can be obtained by a chemical method such as, but not limited to oxidation, reduction, alkylation, acylation, deshydration and/or rearrangement. Examples of chemical conversion of (+)-cedrol and (−)-thujopsene can be found in Charles S. Cell. A Fragrant Introduction to Terpenoid Chemistry. The royal Society of chemistry, 2003. Page 163-172; G. Ohloff, W. Pickenhagen, P. Kraft. Scent and Chemistry—The Molecular World of Odors, Verlag Helvetica Chimica Acta, Zurich, 2011, page 172-174; US007615525; US 20120077722; U.S. Pat. No. 3,845,132 or WO2005083045.

Alternatively, the (+)-cedrol and (−)-thujopsene derivatives can be obtained using a biochemical method by contacting the (+)-cedrol or (−)-thujopsene with an enzyme such as, but not limited to an oxidoreductase, a monooxygenase, a dioxygenase, a transferase. The biochemical conversion can be performed in-vitro using isolated enzymes or in-vivo using whole cells. For example, the same host organisms or cells which produce the (+)-cedrol and (−)-thujopsene can be engineered to express enzymes which are needed to produce derivatives. Examples of biochemical conversion of (+)-cedrol and (−)-thujopsene can be found in Abraham, W. R., P. Washausen, and K. Kieslich. 1987. *Z. Naturforsch.* 42c, 414-419; Takigawa H., Kubota H., Sonohara H., Okuda M., Tanaka S., Fujikura Y. and Ito S. Novel. 1993, *Environ Microbiol.* 59(5), 1336-1341; Lamare, V., J. D. Fourneron, and R. Furstoss. 1987, *Tetrahedron Lett.* 28, 6269-6272; Lamare, V., and R. Furstoss. 1990, *Tetrahedron* 46. 4109-132; Sakamaki H1, Kitanaka S, Chai W, Hayashida Y, Takagi Y, Horiuchi C A. 2001. *J. Nat. Prod.* 64(5). 630-631.

Further provided herein are (+)-cedrol derivatives selected from the compounds set forth in Table I.

TABLE 1

(Examples of cedrol derivatives)

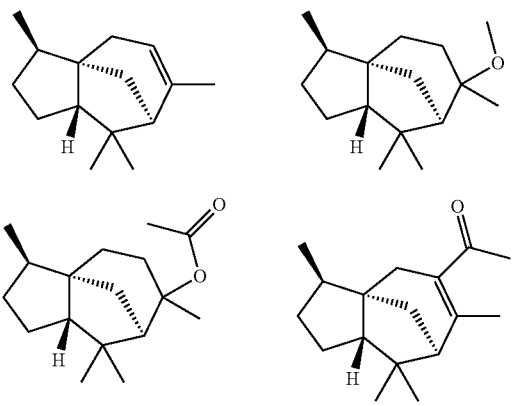

TABLE 1-continued (Examples of cedrol derivatives)

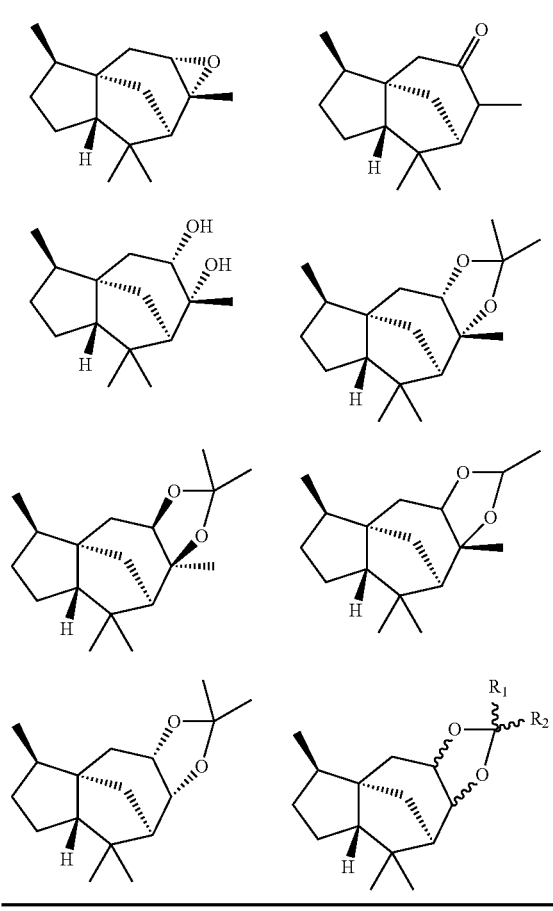

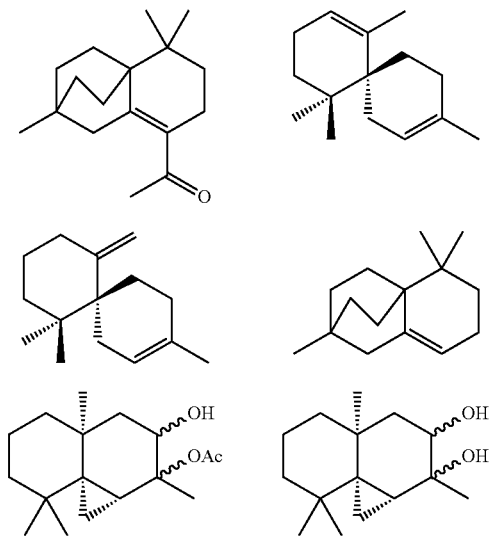

Further provided herein are (−)-thujopsene derivatives selected from the compounds set forth in Table 2.

TABLE 2

(Examples of thujopsene derivates)

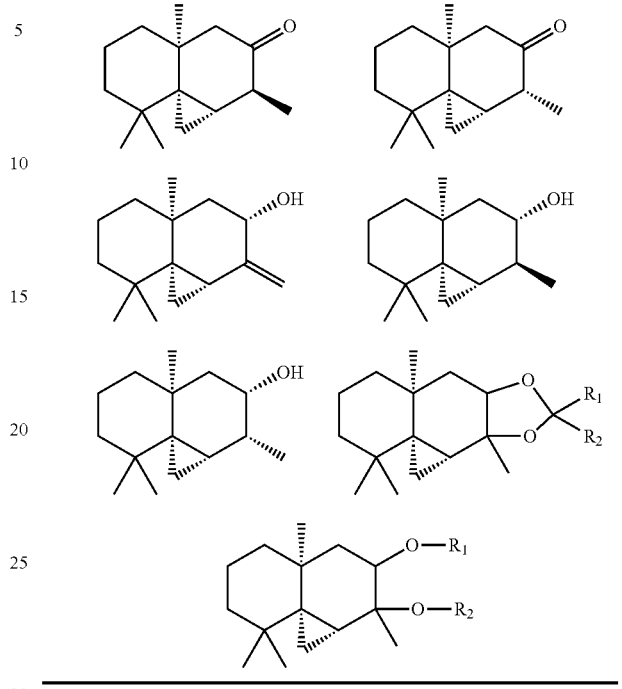

TABLE 2-continued (Examples of thujopsene derivates)

Also provided herein are products comprising (+)-cedrol and (−)-thujopsene or derivatives thereof produced according to the methods described herein.

The following examples are illustrative only and are not intended to limit the scope of the claims or embodiments provided herein.

Example 1

*Juniperus virginiana* Plant Material and Root Transcriptome Sequencing

Seeds of *Juniperus virginiana* were obtained from B&T World SEEDS (Aigues-Vives, France). Seeds were germinated directly in soil in 0.5 L pots. One to two-year old plants were collected for the analysis of the composition in metabolites and transcriptome analysis. The plants were removed from the pots and the roots rinsed with tap water.

The areal part and the roots were separated and frozen in liquid nitrogen. The tissues were first roughly chopped in liquid nitrogen using a Waring Blender (Waring Laboratory, Torrington, USA) and then ground to a fine powder using a mortar and pestle. Samples of the aerial and underground part were extracted with an excess of MTBE (Methyl tert-butyl ether) and analyzed by GCMS. The analysis was performed on an Agilent 6890 Series GC system connected to an Agilent 5975 mass detector. The GC was equipped with 0.25 mm inner diameter by 30 m DB-1 ms capillary column (Agilent). The carrier gas was He at a constant flow of 1 mL/min. The initial oven temperature was 50° C. (1 min hold) followed by a gradient of 10° C./min to 300° C. The identification of the products was based on the comparison of the mass spectra and retention indices with authentic standards and internal databases. The analysis showed that cedrol was present only in the roots and not in the aerial part (FIG. 1).

The roots of the *J. virginiana* plants were thus taken for the transcriptome analysis. Total RNA was extracted following the procedure described in Kolosova et al (Kolosova N, Miller B, Ralph S, Ellis B E, Douglas C, Ritland K, and Bohlmann J, Isolation of high-quality RNA from gymnosperm and angiosperm trees. *J. Biotechniques,* 36(5), 821-4, 2004) with the following modifications. A volume of 10 ml of extraction buffer was used for 1 grams of ground tissue and the extraction buffer was supplemented with 2% (w/v) of PVP (polyvinylpyrrolidone, Sigma-Aldrich). For the CTAB (cethyltrimethylammonium bromide, Sigma-Aldrich) extraction, the nucleic acid pellet was resuspended in 2 ml TE buffer (10 mM Tris-HCl, pH 8, 1 mM EDTA) and the extraction was performed with 2 ml of 5M NaCl and 1 ml 10% CTAB. For the isopropanol precipitation, the nucleic acid pellet was dissolved in 500 µl TE. The final RNA pellet was resuspended in sterile distilled water.

The root transcriptome was sequenced using the Illumina Total RNA-Seq technique and the Illumina HiSeq 2000 sequencer. A total of 16.2 millions of paired-reads of 2×100 bp were generated. The reads were assembled using the Velvet de novo genomic assembler (http://www.ebi.ac.uk/~zerbino/velvet/) and the Oases software (http://www.ebi.ac.uk/~zerbino/oases/). A total 46,644 contigs with an average size of 1,241 bp were assembled. The contigs were search using the tBlastn algorithm (Altschul et al, J. Mol. Biol. 215, 403-410, 1990) and using as query the amino acid sequences of known sesquiterpene synthases. This approach allowed the detection of 138 different terpene synthases encoding sequences. After further sorting of the data, 17 full-length sequences were retained based on their amino-acid sequence homology with known sesquiterpene synthases.

Example 2

Functional Expression of *J. virginiana* Sesquiterpene Synthases

Codon optimized versions of the selected putative terpene-encoding sequences were synthesized in-vitro and cloned in the pJ411 expression plasmid (DNA2.0, Menlo Park, Calif., USA). Heterologous expression of the *J. virginiana* terpene synthases was performed in KRX *E. coli* cells (Promega). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and 0.2% rhamnose and the culture was incubated overnight at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g) and the supernatants containing the soluble proteins were used for further experiments.

The crude *E. coli* protein extracts containing the recombinant protein were used for the characterization of the enzymatic activities. The assays were performed in 2 mL of 50 mM MOPSO pH 7, 10% glycerol, 1 mM DTT, 10 mM $MgCl_2$ in the presence of 10 to 100 µM of farnesyl-diphosphate (FPP, Sigma) and 0.1 to 0.5 mg of crude protein. The tubes were incubated 12 to 24 hours at 30° C. and extracted twice with one volume of pentane. After concentration under a nitrogen flux, the extracts were analysed by GC and GC-MS and compared to extracts from assays with control proteins. The analysis of the products formed by the enzymes was made by GCMS as described in example 1. In these conditions, four recombinant terpene synthases produce cedrol in addition to several other sesquiterpene products. Thus, JvCP1206-3, JvCP1206-4 and JvCP1206-6 produces a mixture of sequiterpene of which cedrol represents at least 70 to 80% of the total sesquiterpene compounds produced. The JvCP1206-5 enzyme produced a mixture in which (−)-thujopsene was the major product and cedrol represented 10% of the total sesquiterpene compounds (FIG. 2).

Example 3

Use of the Recombinant *J. virginiana* Sesquiterpene Synthase for In-Vivo Production of (+)-Cedrol and (−)-Thujopsene in Engineered Cells To evaluate the in-vivo production of cedrol and thujopsene in heterologous cells, *E. coli* cells were transformed with the pJ411 (pJ411-JvCP1206-4, pJ411-JvCP1206-3, pJ411-JvCP1206-6 and pJ411-JvCP1206-5) plasmids containing one of the four *J. virginiana* sesquiterpene synthase identified in Example 2 and the production of sesquiterpenes from the endogenous FPP pool was evaluated. To increase the productivity of the cells, an heterologous FPP synthase and an the enzymes from a complete heterologous mevalonate (MVA) pathway were also expressed in the same cells. The construction of the expression plasmid containing an FPP synthase gene and the gene for a complete MVA pathway was described in patent WO2013064411 or in Schalk et al (2013) *J. Am. Chem. Soc.* 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

KRX *E. coli* cells (Promega) were co-transformed with the plasmid pACYC-29258-4506 and either the plasmid pJ411-JvCP1206-4, pJ411-JvCP1206-3, pJ411-JvCP1206-6 or pJ411-JvCP1206-5. Transformed cells were selected on carbenicillin (50 µg/ml) and chloramphenicol (34 µg/ml) LB-agarose plates. Single colonies were used to inoculate 5 mL liquid LB medium supplemented with the same antibiotics. The culture was incubated overnight at 37° C. The next day 2 mL of TB medium supplemented with the same antibiotics were inoculated with 0.2 mL of the overnight culture. After 6 hours incubation at 37° C., the culture was cooled down to 28° C. and 0.1 mM IPTG and 0.2% rhamnose were added to each tube. The cultures were incubated for 48 hours at 28° C. The cultures were then extracted twice with 2 volumes of MTBE, the organic phase were concentrated to 500 µL and analyzed by GC-MS as described above in Example 1.

In this in-vivo conditions the four sesquiterpene synthases produced mixtures of sesquiterpene with the same ratio of (+)-cedrol as in the in-vitro assays: 70 to 80% of (+)-cedrol for JvCP1206-3, JvCP1206-4 and JvCP1206-6 and 10% for JvCP1206-5 (FIG. 3). With JvCP1206-5, (−)-thujopsene was the major product in the mixture of sesquiterpene produced.

Using these engineered *E. coli* cells, larger (1 L) cultures were used to produce larger quantities of the sequiterpene product mixture produced by these enzymes. The (+)-cedrol was purified from the product mixture by flash chromatography on a silica gel column. A sufficient quantity was obtained to confirm the structure by NMR analysis. The optical rotation was measured using a Bruker Avance 500 MHz spectrometer. The value of $[\alpha]^D_{20}$=+10.6° (0.85%, $CHCl_3$) was in accordance with the literature and confirmed the production of (+)-cedrol.

Example 4

Sequence Comparison of the Four *J. virginiana* Cedrol Synthases

The amino acid sequences of the four *J. virginiana* cedrol synthases were aligned using the ClustalW program and the sequence identities were deduced from the alignment.

The sequence identities between the four cedrol synthases are shown in the table below.

|  | JvCP1206-3 | JvCP1206-4 | JvCP1206-6 | JvCP1206-5 |
|---|---|---|---|---|
| JvCP1206-3 | ID | 97 | 98.6 | 93.4 |
| JvCP1206-4 | 97 | ID | 98.4 | 92.2 |
| JvCP1206-6 | 98.6 | 98.4 | ID | 93.7 |
| JvCP1206-5 | 92.4 | 92.2 | 93.7 | ID |

Example 5

Cedarwood Plant Material Sourcing and Leaf Transcriptome Sequencing

*Platycladus orientalis* 'Beverleyensis' and *Platycladus orientalis* plant materials were collected from Hangzhou, Zhejiang Province, China. To establish whether *P. orientalis* 'Beverleyensis' (sample ID: PNLI20141232) and *P. orientalis* (sample ID: PNLI20141243) contained (+)-cedrol and (−)-thujopsene, their fresh leaves were extracted with dichloromethane for chemical analysis respectively. The extracts were analysed by GC/MS, the parameters of GC/MS analysis were described as below: An Agilent 6890 series GC system equipped with a DB1-ms column 30 m×0.25 mm×0.25 m film thickness (P/N 122-0132, J&W scientific Inc., Folsom, Calif.) and coupled with a 5975 series mass spectrometer was used. The carrier gas was helium at a constant flow of 0.7 mL/min. Injection was in split (1:25) mode with the injector temperature set at 250° C. The oven temperature was programmed from 50° C. (5 min hold) to 300° C. at 5° C./min, then to 340° C. at 50° C./min and held for 3 min. Identification of products was based on mass spectra and retention indices. GC/MS analysis revealed that leaves of *P. orientalis* 'Beverleyensis' contained 37% (+)-cedrol in its total volatile sesquiterpene (FIGS. 5 and 6), whereas the leaves of *P. orientalis* contained 11% (−)-thujopsene in its total volatile sesquiterpene (FIGS. 7 and 8).

Fresh leaves of *P. orientalis* 'Beverleyensis' and *P. orientalis* were used for transcriptome analysis. Total RNA was extracted using the RNeasy Plant Mini Kit (Qiagen, Germany). These total RNA samples were processed using the NEBNext® Ultra™ RNA Library Prep Kit for Illumina (NEB, USA) and TruSeq PE Cluster Kit (Illumina, USA) and then sequenced on Illumina Hiseq 2500 sequencer. An amount of 17 and 22.6 millions of paired-end reads of 2×150 bp was generated for *P. orientalis* 'Beverleyensis' and *P. orientalis*, respectively. The reads from *P. orientalis* 'Beverleyensis' and *P. orientalis* were respectively assembled using the Trinity (http://trinityrnaseq.sf.net/) software. 58300 unigenes with an N50 of 1564 bp and 62252 unigenes with an N50 of 1602 bp were obtained from *P. orientalis* 'Beverleyensis' and *P. orientalis*, respectively. The unigenes were annotated by the InterProScan software (http://www.ebi.ac.uk/Tools/pfa/iprscan/). The sequences of (+)-cedrol synthases and (−)-thujopsene synthase from prior art were used for searching the potential (+)-cedrol synthase and (−)-thujopsene synthase from *P. orientalis* 'Beverleyensis' and *P. orientalis*. This approach provided 2 new putative sesquiterpene synthases sequences for each of the species, including PorB1 from *P. orientalis* 'Beverleyensis' and Por2-3-5 from *P. orientalis*. The enzymatic activity of PorB1 and Por2-3-5 was evaluated as described in Example 6.

Example 6

Functional Expression and Characterization of PorB1 and Por2-3-5

The total RNA extracted by RNeasy Plant Mini Kit (Qiagen, Germany) was first reverse transcribed into cDNA using SMARTer™ RACE cDNA Amplification Kit (Clontech), and then the product was used as the template for gene cloning. PorB1 was amplified from the cDNA of *P. orientalis* 'Beverleyensis' by using forward primer (5'-TT-TAAGTGCTTCTGCGATG-3' (SEQ ID NO: 20)) and reverse primer (5'-ACATCTAGGTTTGTGCCTT-3' (SEQ ID NO: 21)). Por2-3-5 was considered to be improperly assembled so a gene specific reverse primer (5'-ATCGC-CATCTCCAGTGTG-3' (SEQ ID NO: 22)) together with the Universal Primer A Mix provided by SMARTer™ RACE cDNA Amplification Kit (Clontech) were used to clone the 5' end sequence of Por2-3-5, from which the forward primer for full length cloning was designed. Por2-3-5 was then amplified from the cDNA of *P. orientalis* by using forward primer (5'-CTTTAGTGCTTCTGTGATG-3' (SEQ ID NO: 23)) and reverse primer (5'-CATACAAGTTTGTGCCTCA-3' (SEQ ID NO: 24)). The sequences of PorB1 and Por2-3-5 were optimized by following the genetic codon frequency of *E. coli* and synthesized. The restriction site of NdeI was added to the 5' end of both PorB1 and Por2-3-5 while KpnI was added to the 3' end. PorB1 and Por2-3-5 were subcloned either into the pJ401 (DNA 2.0) plasmid or into the pET-Duet-1 (Novagen) plasmid for subsequent expression in *E. coli*.

KRX *E. coli* cells (Promega) were co-transformed with the plasmid pACYC/ScMVA (containing the genes encoding for a heterologous mevalonate pathway, and the plasmid pJ401-PorB1, pETDuet-PorB1, pJ401-Por2-3-5 and pET-Duet-Por2-3-5, respectively. To construct the pACYC/Sc-MVA plasmid, we divided the eight biosynthetic genes into 2 synthetic operons referred as the 'upper' and 'lower' mevalonate (MVA) pathway. As an upper MVA pathway, we created a synthetic operon consisting of an acetoacetyl-CoA thiolase from *E. coli* encoded by atoB, a HMG-CoA synthase and a truncated version of HMG-CoA reductase from *Saccharomyces cerevisiae* encoded by ERG13 and ERG19, respectively. This operon transforms the primary metabolite Acetyl-CoA into (R)-mevalonate. As a 'lower' mevalonate pathway, we created a second synthetic operon encoding a mevalonate kinase (ERG12, *S. cerevisiae*), a phosphomevalonate kinase (ERG8, *S. cerevisiae*), a phosphomevalonate decarboxylase (MVD1, *S. cerevisiae*), an isopentenyl diphosphate isomerase (idi, *E. coli*) and a farnesyl pyrophosphate (FPP) synthase (IspA, *E. coli*). Finally, a second FPP synthase from *S. cerevisiae* (ERG20) was introduced into the upper pathway operon to improve the conversion of the isoprenoid C5 units (IPP and DMAPP) into farnesyl pyrophosphate (FPP). Each operon was subcloned into one of the multiple-cloning sites of a low-copy expression plasmid under the control of a bacteriophage T7 promoter (pACYCDuet-1, Invitrogen).

The co-transformed cells were selected on LB-agar plates containing kanamycin (50 µg/mL final) and chloramphenicol (34 µg/mL final). Single colonies were used to inoculate 5 mL liquid LB medium supplemented with the same antibiotics and glucose (0.4% w/v final), overlayed with 500 µl of decane. Cultures were incubated overnight at 37° C. and 200 rpm shaking. The next day 2 mL of TB medium supplemented with the same antibiotics and glycerol (6% w/v final) were inoculated with 0.3 mL of the overnight cultures, overlayed with 200 µl of decane. After 6 hours of incubation at 37° C. and shaking at 200 rpm, the cultures were cooled down to 25° C. for an hour and IPTG (0.1 M final) and rhamnose (0.02% w/v final) were added to each tube. The cultures were incubated for another 48 hours at 25° C. and 180 rpm shaking. The cultures were then extracted with 1 volume of MTBE, and 50 µl of isolongifolene at 2 mg/mL was added as internal standard before analysing the samples by GC/MS. GC/MS analysis used the same system as described in Example 5. The carrier gas was helium at a constant flow of 1.0 mL/min. Injection was in splitless mode with the injector temperature set at 250° C. The oven temperature was programmed from 80° C. to 220° C. at 10° C./min, then to 280° C. at 30° C./min and held for 1 min. Identification of products was based on mass spectra and retention indices. GC/MS analysis revealed that PorB1 produced (+)-cedrol as the main product with a selectivity of 78% to 88% (FIGS. 9 and 10) and that Por2-3-5 produced (−)-thujopsene as the main product with a selectivity of 45% to 55% (FIGS. 11 and 12).

Example 7

Sequence Comparison of the Cedrol Synthases

The amino acid sequences of PorB1 and Por2-3-5 and of the four *J. virginiana* cedrol synthases were aligned using the ClustalW program and the sequence identities were deduced from the alignment. The sequence identities between the synthases are shown in the table below.

| Query sequence | PorB1 | Por2-3-5 | JvCP1206-3 | JvCP1206-4 | JvCP1206-5 | JvCP1206-6 |
|---|---|---|---|---|---|---|
| PorB1 | ID | 74.10 | 76.16 | 76.33 | 77.36 | 76.16 |
| Por2-3-5 | 74.27 | ID | 76.59 | 76.42 | 79.17 | 76.25 |

-Sequence listing-

SEQ ID NO: 1
JvCP1206-4, amino acid sequence.
MSNLKGDHISSVSSIPAHAFNEWGDAFVQSMEMPYGEPEYRERAETLVKQ

VKILLKEMQTGDGDLIERLEMVDALQCLGIERYFQAEIKEALDYVYRSWD

GTVGIGLGCNSATKHLNATALGLRVLRLHRYDVSPDTLYNFKDNTGEFVL

CGENKVSNDEDTNKEEKVMRSMLNLLRLSSLAFPGEIIMEEAQAFSTRYL

KELLEISGDTFNRSFIKEVEYALTYEWPRTFTRWEAWNFIEICDLDNDRL

EDKRILQLAKLDFNILQFQYKLEMKNLSSWWVESGISNLVATRARHIEYL

FWAVASTDEMEFSSSRIALAKTTAIITVMDDIFDDYATLEYLKCISDAIS

KNWDVSIIENIPNNLKTCFEFISKTVHQMAIDATKYQGRDMMPFITKAWA

DYIEACFEEARWKLTGYFPTYDEYMKSAELCVGFGQIFLSSGLLASPNLC

DDDIEKIYLDKSRFFKLMRVCMRLIDDINDFEDERLHGKIASAIACYKGD

HPNCSESEAINQIITLNNKLLRELTREFFKSNMNFLEWQKICVNSTRGVQ

FFYIFRDGFTYSHKEIKQQIFKILVDPIKM

SEQ ID NO: 2
JvCP1206-3, amino acid sequence.
MSNLKGDHISSVSSIPAHAFNEWGDAFVQSMEMPYGEPEYRERAETLVKQ

VKILLKEMQTGDGDLIERLEMVDALQCLGIERYFQAEIKEALDYVYRSWD

GTVGIGLGCNSATKHLNATALGLRVLRLHRYDVSPDTLHNFKDNTGKFVL

TGENKDNNDEDTNKEEKVMRSILNLFRLSSLAFPGEIIMEEAKAFSTRYL

KELLEISRDTFNRSFIKEVEYALTYEWPRTFTRWEAWNFIEICDLDNDRL

EDKRILQLAKLDFNILQFQYKLEMKNLSSWWVESGISNLVATRARHIEYL

FWAVASTDEMEFSSSRIALAKTTAIITVMDDIFDDYATLEYLKCISDAIS

KNWDVSIIENIPNNLKTCFEFISKTVHQMAIDATKYQGRDMMPFITKAWA

DYIEACFEEARWKLTGYFPTYDEYMKSAELCVGFGQIFLSSGLLASPNLC

DDDIEKIYLDKSRFFKLMRVCMRLIDDINDFEDERLHGKIASAIACYKGD

HPNCSESEAINQIVMLNNKLLRELTREFLKSNMNFLEWEKICVNSTRGVQ

FCYIFGDGFTYSHKEIKQQIFKILVNPIKV

SEQ ID NO: 3
JvCP1206-6, amino acid sequence.
MSNLKGDHISSVSSIPAHAFNEWGDAFVQSMEMPYGEPEYRERAETLVKQ

VKILLKEMQTGDGDLIERLEMVDALQCLGIERYFQAEIKEALDYVYRSWD

GTVGIGLGCNSATKHLNATALGLRVLRLHRYDVSPDTLHNFKDNTGKFVL

TGENKDNNDEDTNKEEKVMRSILNLFRLSSLAFPGEIIMEEAKAFSTRYL

KELLEISRDTFNRSFIKEVEYALTYEWPRTFTRWEAWNFIEICDLDNDRL

EDKRILQLAKLDFNILQFQYKLEMKNLSSWWVESGISNLVATRARHIEYL

FWAVASTDEMEFSSSRIALAKTTAIITVMDDIFDDYATLEYLKCISDAIS

-continued

KNWDVSIIENIPNNLKTCFEFISKTVHQMAIDATKYQGRDMMPFITKAWA

DYIEACFEEARWKLTGYFPTYDEYMKSAELCVGFGQIFLSSGLLASPNLC

DDDIEKIYLDKSRFFKLMRVCMRLIDDINDFEDERLHGKIASAIACYKGD

HPNCSESEAINQIITLNNKLLRELTREFFKSNMNFLEWQKICVNSTRGVQ
FFYIFRDGFTYSHKEIKQQIFKILVDPIKM

SEQ ID NO: 4
JvCP1206-5, amino acid sequence.
MSNLKGDHISSVSSIPAHAFNEWGDAFVQSMEMPYGEPEYRERAETLVKQ
VKILLKEMQTGDGDLIERLEMVDALQCLGIERYFQAEIKEALDYVYRSWD
GTVGIGLGCNSATKHLNATALGLRVLRLHRYDVSPDTLHNFKDNTGKFVL
TGENKDNNDEDTNKEEKVMRSILNLFRLSSLAFPGEIIMEEAKAFSTRYL
KELLEISRDTFNRSFIKEVEYALTYEWPRTFTRWEARNFIEICDLDNDRL
KDKRILELAKLDFNILQFQYQLEMKNLSRWWVESGISNLVATRERSIEYL
FWAVTSTDELEFSSSRIAHAKCTTIITIMDDIFDDYATLEQLKCIVDAIS
KNWDVSIIENIPNNLKTCFEFVSKTVHELAIDATEYQGRDMMPFITKAWT
DYGEACFEQACWKVKGYFPTYNEYIKCAELSVAFGPILLHTALLASPDLC
DDDIEKIYLDKSRFFKLMRVCMRLIDDINDFEDERLHGKIASAIACYKGD
HPNCSESEAINQIITLNNKLLRELTREFFKSNMNFLEWQKICVNSTRGVQ
FFYIFRDGFTYSHKEIKQQIFKILVDPIKM SEQ ID NO: 5
JvCP1206-4, wild type cDNA sequence.
ATGTCGAATTTGAAAGGAGACCACATTTCTTCTGTTTCTTCCATTCCAGC
CCATGCTTTTAATGAGTGGGGCGATGCTTTTGTTCAATCTATGGAGATGC
CGTACGGGGAACCTGAATACCGTGAACGTGCTGAAACACTTGTGAAACAA
GTCAAAATCTTGTTAAAAGAAATGCAAACTGGAGATGGTGATCTAATCGA
GCGGCTTGAGATGGTTGATGCTTTGCAATGCCTTGGCATTGAGCGATATT
TTCAGGCTGAGATTAAAGAAGCTCTTGATTACGTTTACCGCTCTTGGGAT
GGAACTGTGGGAATAGGATTAGGCTGCAACAGTGCTACAAAGCATTTGAA
TGCCACAGCTTTGGGACTCAGAGTACTTCGACTCCATCGTTATGACGTCT
CTCCAGACACGTTGTACAATTTCAAGGACAATACTGGCGAGTTCGTCCTC
TGTGGAGAAAATAAAGTGAGTAACGATGAGGATACTAATAAGGAAGAGAA
AGTGATGAGAAGTATGCTCAACCTGTTAAGACTATCCAGTTTGGCATTCC
CTGGAGAAATCATTATGGAAGAGGCTCAAGCATTTAGCACTAGATATCTT
AAAGAATTATTAGAAATTTCTGGAGATACATTTAACAGGAGTTTTATTAA
AGAGGTGGAGTATGCTCTTACATATGAATGGCCTCGAACCTTTACTAGAT
GGGAGGCGTGGAATTTCATAGAGATCTGTGATTTAGATAATGACAGGTTG
GAAGACAAAAGGATTTTACAGCTTGCAAAATTGGATTTTAATATACTACA
ATTTCAATATAAGTTGGAGATGAAAAATCTGTCAAGTTGGTGGGTTGAAT
CTGGCATCTCCAATCTGGTTGCAACAAGGGCCCGACATATTGAATATCTT
TTTTGGGCAGTTGCTTCTACAGATGAGATGGAGTTTTCTAGTAGTAGAAT
AGCTCTTGCAAAGACCACCGCAATTATTACAGTAATGGATGACATTTTTG
ATGACTATGCAACACTTGAGTATCTCAAATGTATTTCAGATGCCATTTCT
AAAAATTGGGATGTTTCTATTATAGAAAATATTCCCAACAACTTGAAGAC
ATGTTTTGAATTTATTTCTAAAACAGTTCATCAAATGGCAATAGATGCTA
CTAAATATCAAGGACGTGACATGATGCCTTTTATTACAAAAGCGTGGGCA
GATTATATAGAAGCCTGCTTTGAGGAGGCACGCTGGAAACTGACAGGATA
TTTTCCAACCTACGATGAGTACATGAAATCTGCTGAACTATGTGTTGGAT
TTGGACAGATATTTTTATCTAGTGGGCTACTAGCATCTCCTAATTTATGT
GATGATGATATTGAGAAGATATACCTTGACAAATCTAGATTCTTTAAACT
CATGCGAGTGTGTATGCGGTTGATTGATATATAAATGATTTTGAGGATG
AGAGGCTCCATGGAAAGATTGCCTCAGCTATTGCTTGTTACAAGGGTGAT
CATCCAAATTGTTCAGAAAGCGAGGCCATCAATCAAATCATCACGCTCAA
TAATAAATTATTGAGAGAATTGACAAGAGAATTTTTTAAATCAAATATGA
ATTTTCTTGAATGGCAAAAGATATGTGTCAATAGTACCAGAGGAGTACAA
TTTTTCTATATATTTAGAGATGGGTTTACATATTCTCACAAGGAGATCAA
GCAGCAGATATTTAAAATCCTTGTTGATCCAATAAAAATGTAG SEQ ID NO: 6
JvCP1206-3, wild type cDNA sequence.
ATGTCGAATTTGAAAGGAGACCACATTTCTTCTGTTTCTTCCATTCCAGC
CCATGCTTTTAATGAGTGGGGCGATGCTTTTGTTCAATCTATGGAGATGC
CGTACGGGGAACCTGAATACCGTGAACGTGCTGAAACACTTGTGAAACAA
GTCAAAATCTTGTTAAAAGAAATGCAAACTGGAGATGGTGATCTAATCGA
GCGGCTTGAGATGGTTGATGCTTTGCAATGCCTTGGCATTGAGCGATATT
TTCAGGCTGAGATTAAAGAAGCTCTTGATTACGTTTACCGCTCTTGGGAT
GGAACTGTGGGAATAGGATTAGGCTGCAACAGTGCTACAAAGCATTTGAA
TGCCACAGCTTTGGGACTCAGAGTACTTCGACTCCATCGTTATGACGTCT
CTCCAGACACGTTGCACAATTTCAAGGACAATACTGGGAAGTTCGTCCTC
ACTGGAGAAAATAAAGACAATAACGATGAAGATACTAATAAGGAAGAGAA
AGTGATGAGAAGTATTCTCAACCTGTTCAGACTATCCAGTTGGCATTCC
CTGGAGAAATTATTATGGAAGAGGCTAAAGCATTTAGCACTAGATATCTT
AAAGAATTATTAGAAATTTCTAGAGATACATTTAACAGGAGTTTTATTAA
AGAGGTGGAGTATGCTCTTACATATGAATGGCCTCGAACCTTTACTAGAT
GGGAGGCGTGGAATTTCATAGAGATCTGTGATTTAGATAATGACAGGTTG
GAAGACAAAAGGATTTTACAGCTTGCAAAATTGGATTTTAATATACTACA
ATTTCAATATAAGTTGGAGATGAAAAATCTGTCAAGTTGGTGGGTTGAAT
CTGGCATCTCCAATCTGGTTGCAACAAGGGCCCGACATATTGAATATCTT
TTTTGGGCAGTTGCTTCTACAGATGAGATGGAGTTTTCTAGTAGTAGAAT
AGCTCTTGCAAAGACCACCGCAATTATTACAGTAATGGATGACATTTTTG
ATGACTATGCAACACTTGAGTATCTCAAATGTATTTCAGATGCCATTTCT
AAAAATTGGGATGTTTCTATTATAGAAAATATTCCCAACAACTTGAAGAC
ATGTTTTGAATTTATTTCTAAAACAGTTCATCAAATGGCAATAGATGCTA
CTAAATATCAAGGACGTGACATGATGCCTTTTATTACAAAAGCGTGGGCA
GATTATATAGAAGCCTGCTTTGAGGAGGCACGCTGGAAACTGACAGGATA
TTTTCCAACCTACGATGAGTACATGAAATCTGCTGAACTATGTGTTGGAT
TTGGACAGATATTTTTATCTAGTGGGCTACTAGCATCTCCTAATTTATGT
GATGATGATATTGAGAAGATATACCTTGACAAATCTAGATTCTTTAAACT
CATGCGAGTGTGTATGCGGTTGATTGATATATAAATGATTTTGAGGATG -continued

AGAGGCTCCATGGAAAGATTGCCTCAGCTATTGCTTGTTACAAGGGTGAT

CATCCAAATTGTTCAGAAAGTGAGGCCATCAATCAAATCGTCATGCTCAA

TAATAAATTATTGAGAGAATTGACAAGAGAATTTTTAAAATCAAATATGA

ATTTTCTTGAATGGAAAAGATATGTGTCAATAGTACAAGAGGGGTACAA

TTTTGCTATATATTTGGAGATGGGTTTACATATTCTCACAAGGAGATCAA

GCAACAGATATTTAAAATTCTTGTCAATCCAATAAAGTGTAG

SEQ ID NO: 7
JvCP1206-6, wild type cDNA sequence.
ATGTCGAATTTGAAAGGAGACCACATTTCTTCTGTTTCTTCCATTCCAGC

CCATGCTTTTAATGAGTGGGGCGATGCTTTTGTTCAATCTATGGAGATGC

CGTACGGGGAACCTGAATACCGTGAACGTGCTGAAACACTTGTGAAACAA

GTCAAAATCTTGTTAAAAGAAATGCAAACTGGAGATGGTGATCTAATCGA

GCGGCTTGAGATGGTTGATGCTTTGCAATGCCTTGGCATTGAGCGATATT

TTCAGGCTGAGATTAAAGAAGCTCTTGATTACGTTTACCGCTCTTGGGAT

GGAACTGTGGGAATAGGATTAGGCTGCAACAGTGCTACAAAGCATTTGAA

TGCCACAGCTTTGGGACTCAGAGTACTTCGACTCCATCGTTATGACGTCT

CTCCAGACACGTTGCACAATTTCAAGGACAATACTGGGAAGTTCGTCCTC

ACTGGAGAAAATAAAGACAATAACGATGAAGATACTAATAAGGAAGAGAA

AGTGATGAGAAGTATTCTCAACCTGTTCAGACTATCCAGTTTGGCATTCC

CTGGAGAAATTATTATGGAAGAGGCTAAAGCATTTAGCACTAGATATCTT

AAAGAATTATTAGAAATTTCTAGAGATACATTTAACAGGAGTTTTATTAA

AGAGGTGGAGTATGCTCTTACATATGAATGGCCTCGAACCTTTACTAGAT

GGGAGGCGTGGAATTTCATAGAGATCTGTGATTTAGATAATGACAGGTTG

GAAGACAAAAGGATTTTACAGCTTGCAAAATTGGATTTTAATATACTACA

ATTTCAATATAAGTTGGAGATGAAAAATCTGTCAAGTTGGTGGGTTGAAT

CTGGCATCTCCAATCTGGTTGCAACAAGGGCCCGACATATTGAATATCTT

TTTTGGGCAGTTGCTTCTACAGATGAGATGGAGTTTTCTAGTAGTAGAAT

AGCTCTTGCAAAGACCACCGCAATTATTACAGTAATGGATGACATTTTTG

ATGACTATGCAACACTTGAGTATCTCAAATGTATTTCAGATGCCATTTCT

AAAAATTGGGATGTTTCTATTATAGAAAATATTCCCAACAACTTGAAGAC

ATGTTTGAATTTATTTCTAAAACAGTTCATCAAATGGCAATAGATGCTA

CTAAATATCAAGGACGTGACATGATGCCTTTTATTACAAAAGCGTGGGCA

GATTATATAGAAGCCTGCTTTGAGGAGGCACGCTGGAAACTGACAGGATA

TTTTCCAACCTACGATGAGTACATGAAATCTGCTGAACTATGTGTTGGAT

TTGGACAGATATTTTTATCTAGTGGGCTACTAGCATCTCCTAATTTATGT

GATGATGATATTGAGAAGATATACCTTGACAAATCTAGATTCTTTAAACT

CATGCGAGTGTGTATGCGGTTGATTGATGATATAAATGATTTTGAGGATG

AGAGGCTCCATGGAAAGATTGCCTCAGCTATTGCTTGTTACAAGGGTGAT

CATCCAAATTGTTCAGAAAGCGAGGCCATCAATCAAATCATCACGCTCAA

TAATAAATTATTGAGAGAATTGACAAGAGAATTTTTTAAATCAAATATGA

ATTTTCTTGAATGGCAAAAGATATGTGTCAATAGTACCAGAGGAGTACAA

TTTTTCTATATATTTAGAGATGGGTTTACATATTCTCACAAGGAGATCAA

GCAGCAGATATTTAAAATCCTTGTTGATCCAATAAAAATGTAG

SEQ ID NO: 8
JvCP1206-5, wild type cDNA sequence.
ATGTCGAATTTGAAAGGAGACCACATTTCTTCTGTTTCTTCCATTCCAGC

CCATGCTTTTAATGAGTGGGGCGATGCTTTTGTTCAATCTATGGAGATGC

CGTACGGGGAACCTGAATACCGTGAACGTGCTGAAACACTTGTGAAACAA

GTCAAAATCTTGTTAAAAGAAATGCAAACTGGAGATGGTGATCTAATCGA

GCGGCTTGAGATGGTTGATGCTTTGCAATGCCTTGGCATTGAGCGATATT

TTCAGGCTGAGATTAAAGAAGCTCTTGATTACGTTTACCGCTCTTGGGAT

GGAACTGTGGGAATAGGATTAGGCTGCAACAGTGCTACAAAGCATTTGAA

TGCCACAGCTTTGGGACTCAGAGTACTTCGACTCCATCGTTATGACGTCT

CTCCAGACACGTTGCACAATTTCAAGGACAATACTGGGAAGTTCGTCCTC

ACTGGAGAAAATAAAGACAATAACGATGAAGATACTAATAAGGAAGAGAA

AGTGATGAGAAGTATTCTCAACCTGTTCAGACTATCCAGTTTGGCATTCC

CTGGAGAAATTATTATGGAAGAGGCTAAAGCATTTAGCACTAGATATCTT

AAAGAATTATTAGAAATTTCTAGAGATACATTTAACAGGAGTTTTATTAA

AGAGGTGGAGTATGCTCTTACATATGAATGGCCTCGAACCTTTACTAGAT

GGGAGGCCCGGAATTTCATAGAAATCTGTGATTTAGATAATGACAGGTTG

AAAGATAAAGGATTTTAGAGCTTGCAAAATTGGATTTTAATATACTACA

ATTTCAATATCAGCTGGAGATGAAAAATCTCTCAAGGTGGTGGGTTGAAT

CTGGCATCTCCAATCTAGTTGCAACAAGGGAGCGATCTATTGAATATCTT

TTTTGGGCAGTTACTTCTACAGATGAGTTGGAATTTTCTAGTAGTAGAAT

AGCTCATGCAAAGTGCACCACAATAATTACAATAATGGATGATATTTTTG

ATGACTATGCAACACTTGAGCAACTCAAATGTATTGTAGATGCCATTTCA

AAAAATTGGGATGTTTCTATTATAGAGAATATACCCAATAACTTGAAGAC

ATGCTTTGAATTTGTTTCTAAAACAGTTCATGAATTGGCAATAGATGCTA

CTGAATATCAAGGACGTGACATGATGCCTTTTATTACAAAAGCGTGGACA

GATTATGGAGAAGCTTGCTTTGAGCAGGCATGCTGGAAAGTGAAAGGATA

TTTTCCAACCTACAATGAGTACATAAAGTGTGCTGAATTAAGTGTTGCAT

TTGGACCGATATTGTTACATACTGCACTACTAGCATCTCCCGATTTATGC

GATGATGATATTGAGAAGATATACCTTGACAAATCTAGATTCTTTAAACT

CATGCGAGTGTGTATGCGGTTGATTGATGATATAAATGATTTTGAGGATG

AGAGGCTCCATGGAAAGATTGCCTCAGCTATTGCTTGTTACAAGGGTGAT

CATCCAAATTGTTCAGAAAGCGAGGCCATCAATCAAATCATCACGCTCAA

TAATAAATTATTGAGAGAATTGACAAGAGAATTTTTTAAATCAAATATGA

ATTTTCTTGAATGGCAAAAGATATGTGTCAATAGTACCAGAGGAGTACAA

TTTTTCTATATATTTAGAGATGGGTTTACATATTCTCACAAGGAGATCAA

GCAGCAGATATTTAAAATCCTTGTTGATCCAATAAAAATGTAG

SEQ ID NO: 9
JvCP1206-4, codon optimized cDNA sequence.
ATGAGCAATTTGAAAGGCGATCACATCAGCAGCGTATCTAGCATTCCGGC

ACATGCATTCAATGAATGGGGCGACGCCTTTGTTCAGAGCATGGAAATGC

CGTACGGTGAGCCGGAATATCGCGAGCGTGCGGAGACTCTGGTCAAACAA

GTGAAGATTCTGCTGAAAGAGATGCAAACCGGTGACGGCGACTTGATTGA

ACGTCTGGAGATGGTGGATGCGCTGCAATGCCTGGGTATTGAGCGTTATT

TCCAAGCGGAGATTAAAGAGGCGCTGGATTACGTGTACCGTAGCTGGGAC

GGCACGGTGGGCATCGGTCTGGGTTGCAACTCGGCCACCAAGCATCTGAA

CGCTACCGCTCTGGGCCTGCGTGTTCTGCGCCTGCATCGTTATGATGTGA

GCCCTGACACCTTGTATAACTTTAAGGACAATACCGGCGAATTTGTCCTG

TGTGGTGAGAACAAAGTTAGCAATGATGAAGATACTAACAAAGAAGAGAA

GGTTATGCGCAGCATGTTGAATTTGCTGCGCCTGAGCTCTTTGGCTTTTC

CGGGTGAGATCATCATGGAAGAAGCGCAGGCGTTTAGCACCCGTTATCTG

AAAGAACTGCTGGAGATCTCTGGCGACACCTTTAATCGTAGCTTCATCAA

AGAGGTCGAGTACGCGCTGACCTATGAATGGCCACGTACCTTCACCCGCT

GGGAAGCATGGAATTTCATTGAAATTTGTGACCTGGACAACGACCGTCTG

GAAGATAAGCGTATCCTGCAGCTGGCGAAGCTGGACTTCAACATCCTGCA

GTTTCAGTACAAGCTGGAGATGAAGAATCTGAGCAGCTGGTGGGTTGAGA

GCGGTATTTCCAACTTGGTCGCGACGCGTGCGCGCCACATCGAGTACTTG

TTTTGGGCGGTCGCGTCTACGGACGAGATGGAGTTTTCCAGCTCCCGTAT

CGCCCTGGCGAAAACCACGGCTATTATCACCGTTATGGATGACATTTTCG

ATGATTACGCGACGCTGGAGTACCTGAAATGTATTTCCGACGCCATTAGC

AAGAATTGGGATGTCAGCATTATTGAAAACATCCCGAACAATCTGAAAAC

GTGCTTCGAGTTCATTAGCAAAACGGTGCACCAGATGGCCATTGATGCGA

CGAAGTATCAGGGCCGTGACATGATGCCGTTTATCACTAAGGCCTGGGCT

GATTACATTGAAGCCTGTTTCGAAGAAGCACGCTGGAAGCTGACGGGTTA

CTTCCCGACCTATGATGAGTACATGAAAAGCGCGGAACTGTGCGTGGGTT

TCGGTCAGATTTTTCTGAGCTCGGGCCTGTTGGCAAGCCCGAATTTGTGT

GATGACGATATTGAGAAGATTTACCTGGATAAAAGCCGTTTCTTCAAGCT

GATGCGCGTTTGCATGCGTCTGATCGATGACATCAACGACTTCGAGGACG

AACGTCTGCACGGTAAGATCGCAAGCGCAATCGCATGCTATAAGGGTGAC

CACCCGAATTGCAGCGAAAGCGAGGCAATTAACCAAATCATCACCTTGAA

CAATAAACTGCTGCGCGAACTGACCCGCGAGTTTTTCAAGAGCAATATGA

ACTTTCTGGAGTGGCAGAAAATCTGTGTGAACTCCACCCGTGGTGTCCAA

TTCTTCTATATCTTTCGTGATGGTTTTACCTACTCTCACAAAGAGATTAA

ACAACAAATCTTCAAAATTCTGGTTGACCCGATCAAGATGTAA

SEQ ID NO: 10
JvCP1206-3, codon optimized cDNA sequence.
ATGAGCAATTTGAAAGGCGATCACATCAGCAGCGTATCTAGCATTCCGGC

ACATGCATTCAATGAGTGGGGTGATGCGTTCGTCCAAAGCATGGAAATGC

CGTATGGTGAGCCGGAGTACCGTGAACGTGCTGAAACGCTGGTTAAACAA

GTGAAGATTCTGCTGAAAGAAATGCAGACCGGCGATGGTGACCTGATCGA

ACGCCTGGAGATGGTGGACGCACTGCAATGTCTGGGTATTGAGCGTTACT

TTCAAGCCGAGATCAAAGAAGCGCTGGACTACGTGTACCGCAGCTGGGAT

GGCACCGTCGGTATTGGTCTGGGTTGCAATAGCGCGACCAAGCACCTGAA

TGCAACGGCGCTGGGTCTGCGCGTTCTGCGCCTGCACCGCTATGATGTTA

GCCCGGATACTCTGCATAACTTCAAGGATAACACGGGTAAGTTTGTCCTG

ACGGGCGAGAACAAAGACAATAACGACGAAGATACTAACAAAGAAGAGAA

GGTTATGCGTTCCATTCTGAATCTGTTTCGTTTGAGCTCCCTGGCATTTC

CGGGCGAGATCATTATGGAAGAGGCTAAAGCGTTCTCTACTCGTTACCTG

AAAGAACTGCTGGAAATCAGCCGCGACACCTTCAATCGTAGCTTCATCAA

AGAGGTTGAGTATGCTTTGACCTACGAGTGGCCTCGCACCTTTACGCGTT

GGGAAGCGTGGAATTTCATCGAAATTTGCGACCTGGACAACGACCGTCTG

GAAGATAAGCGTATCTTGCAGCTGGCAAAGCTGGACTTCAATATCCTGCA

ATTTCAGTACAAACTGGAAATGAAGAATCTGTCCAGCTGGTGGGTCGAGA

GCGGTATTAGCAACCTGGTGGCGACGCGTGCGCGTCATATCGAATACTTG

TTCTGGGCGGTCGCCAGCACGGACGAGATGGAGTTCAGCAGCTCTCGTAT

TGCCCTGGCAAAGACCACCGCAATTATCACCGTGATGGATGACATTTTCG

ATGACTACGCGACCCTGGAGTACCTGAAATGTATTTCGGATGCGATCAGC

AAGAACTGGGATGTTTCCATTATTGAAAACATTCCGAACAACCTGAAAAC

CTGTTTTGAGTTTATCAGCAAAACCGTTCACCAGATGGCCGATCGATGCTA

CGAAATATCAGGGTCGTGACATGATGCCATTCATTACGAAGGCGTGGGCC

GACTATATTGAGGCATGTTTCGAAGAAGCGCGTTGGAAGCTGACGGGCTA

CTTTCCGACCTACGACGAGTATATGAAGAGCGCGGAATTGTGCGTTGGTT

TTGGTCAGATCTTTCTGAGCTCTGGCCTGTTGGCTTCCCCGAATCTGTGC

GACGACGACATTGAGAAAATCTATTTGGACAAGTCCCGCTTCTTCAAGCT

GATGCGTGTTTGTATGCGCTTGATCGATGACATTAACGATTTCGAGGATG

AGCGTCTGCACGGCAAAATCGCCAGCGCCATCGCCTGCTATAAAGGCGAC

CATCCGAATTGTAGCGAGTCTGAGGCGATCAACCAGATCGTGATGCTGAA

TAACAAATTGCTGCGCGAACTGACCCGCGAGTTCCTGAAGAGCAATATGA

ACTTTCTGGAGTGGGAAGATTTGCGTGAACAGCACCCGTGGTGTGCAA

TTCTGCTACATTTTTGGCGATGGTTTTACCTATAGCCACAAAGAAATCAA

ACAACAGATCTTTAAGATTCTGGTCAATCCGATCAAGGTCTAA

SEQ ID NO: 11
JvCP1206-6, codon optimized cDNA sequence.
ATGAGCAATTTGAAAGGCGATCACATCAGCAGCGTATCTAGCATTCCGGC

ACATGCATTCAATGAGTGGGGTGACGCGTTTGTCAGAGCATGGAAATGC

CGTATGGTGAACCGGAATATCGTGAGCGTGCTGAAACCCTGGTGAAGCAA

GTCAAGATTCTGTTGAAAGAAATGCAAACCGGCGACGGTGATCTGATCGA

GCGCCTGGAGATGGTTGATGCGCTGCAGTGTCTGGGTATTGAGCGCTATT

TTCAAGCCGAGATCAAAGAAGCGCTGGATTACGTTTATCGTAGCTGGGAT

GGCACGGTTGGTATTGGCCTGGGCTGCAATAGCGCGACCAAGCACCTGAA

CGCTACCGCGCTGGGTCTGCGCGTGTTGCGTTTGCACCGCTACGACGTTT

-continued
```
CGCCGGATACTCTGCATAACTTTAAAGATAATACGGGCAAATTCGTCCTG
ACGGGTGAGAACAAAGATAACAACGATGAGGACACGAACAAAGAAGAAA
AGTCATGCGCTCCATCCTGAATCTGTTTCGTCTGAGCAGCCTGGCTTTTC
CTGGCGAGATCATTATGGAAGAAGCGAAGGCGTTTAGCACCCGTTACCTG
AAAGAACTGTTGGAGATCAGCCGTGATACCTTCAACCGTAGCTTTATCAA
AGAGGTGGAGTACGCGCTGACCTACGAGTGGCCGCGTACCTTTACCCGTT
GGGAAGCCTGGAATTTCATTGAGATCTGCGACCTGGATAACGACCGTCTG
GAAGATAAGCGTATTCTGCAATTGGCGAAACTGGACTTCAATATTCTGCA
GTTCCAGTACAAGCTGGAGATGAAGAATCTGTCCAGCTGGTGGGTTGAGA
GCGGTATCAGCAACCTGGTCGCGACGCGTGCACGTCATATCGAGTACCTG
TTTTGGGCGGTCGCTAGCACGGACGAAATGGAGTTTAGCTCCAGCCGCAT
TGCACTGGCCAAGACCACTGCAATCATTACCGTGATGGATGATATCTTTG
ACGATTACGCGACCTTGGAGTATCTGAAATGCATCTCTGACGCGATCAGC
AAGAACTGGGACGTTAGCATTATTGAAAACATTCCGAATAACTTGAAAAC
GTGTTTTGAGTTCATTAGCAAAACTGTTCACCAAATGGCAATCGACGCCA
CCAAATATCAGGGCCGTGACATGATGCCGTTTATCACCAAGGCCTGGGCA
GACTACATCGAGGCATGCTTTGAAGAAGCTCGCTGGAAACTGACGGGTTA
TTTCCCGACCTACGATGAGTACATGAAGTCCGCCGAGCTGTGCGTCGGCT
TCGGTCAGATTTTCCTGTCGAGCGGTCTGCTGGCAAGCCCAAATCTGTGT
GACGACGACATTGAAAAGATTTACTTGGACAAGAGCCGCTTTTTCAAGCT
GATGCGTGTGTGTATGCGTCTGATTGATGACATTAACGATTTCGAGGACG
AACGCCTGCACGGTAAGATCGCGTCCGCCATTGCGTGCTACAAGGGCGAC
CATCCGAATTGCTCTGAATCTGAAGCGATTAACCAAATCATCACCCTGAA
CAATAAACTGCTGCGTGAGTTGACCCGTGAGTTCTTCAAGTCTAACATGA
ATTTTCTGGAGTGGCAGAAGATTTGTGTTAATAGCACGCGCGGTGTGCAA
TTCTTCTATATCTTCCGCGATGGTTTCACGTATAGCCACAAAGAGATCAA
GCAGCAGATTTTCAAAATCCTGGTGGACCCGATCAAAATGTAA
```
SEQ ID NO: 12
JvCP1206-5, codon optimized cDNA sequence.
```
ATGAGCAATTTGAAAGGCGATCACATCAGCAGCGTATCTAGCATTCCGGC
ACATGCATTCAACGAGTGGGGCGACGCTTTCGTGCAATCTATGGAGATGC
CGTATGGTGAGCCGGAGTACCGTGAGCGTGCGGAAACGCTGGTGAAACAA
GTTAAGATCCTGCTGAAAGAGATGCAGACCGGTGATGGCGATCTGATTGA
ACGTCTGGAGATGGTCGATGCGCTGCAATGCCTGGGTATCGAACGTTACT
TCCAGGCGGAGATCAAAGAGGCCCTGGACTATGTTTACCGTAGCTGGGAT
GGCACGGTCGGTATTGGTCTGGGTTGCAACAGCGCGACGAAACACCTGAA
CGCGACGGCTCTGGGTCTGCGCGTTCTGCGCCTGCACCGTTACGATGTCA
GCCCGGACACGCTGCATAACTTTAAGGACAATACGGGCAAATTTGTGCTG
ACTGGTGAAAACAAAGATAACAACGACGAGGATACCAATAAAGAAGAAA
GGTCATGCGTTCCATCCTGAATTTGTTCCGCCTGAGCAGCTTGGCCTTTC
CGGGGCGAGATCATTATGGAAGAAGCGAAGGCGTTTAGCACCCGTTATCTG
AAAGAACTGCTGGAAATTAGCCGCGACACCTTTAACCGCAGCTTTATCAA
AGAAGTCGAATACGCCCTGACCTACGAGTGGCCGCGTACCTTTACCCGTT
GGGAAGCGCGTAATTTCATTGAAATCTGTGATTTGGATAATGACCGTCTG
AAGGATAAGCGTATCCTGGAGCTGGCGAAGCTGGACTTTAACATTTTGCA
GTTCCAATATCAGTTGGAGATGAAAAATCTGAGCCGCTGGTGGGTGGAGA
GCGGTATTAGCAACTTGGTTGCCACTCGTGAGCGTTCCATTGAATACCTG
TTCTGGGCGGTCACGTCTACCGACGAACTGGAGTTTAGCTCTAGCCGCAT
CGCGCACGCGAAATGCACCACGATCATCACCATCATGGATGATATCTTTG
ACGATTATGCAACCCTGGAGCAACTGAAGTGTATTGTGGACGCTATTTCG
AAGAACTGGGACGTTTCCATCATTGAGAACATTCCGAATAATCTGAAAAC
CTGTTTCGAGTTCGTGAGCAAAACCGTTCACGAGCTGGCAATTGATGCCA
CCGAGTATCAAGGTCGTGACATGATGCCGTTCATCACCAAGGCCTGGACC
GATTATGGTGAAGCATGTTTCGAGCAGGCTTGCTGGAAGGTGAAGGGTTA
CTTTCCTACCTACAACGAGTATATCAAGTGCGCAGAACTGAGCGTCGCCT
TTGGCCCGATTCTGCTGCATACGGCGCTGTTGGCGAGCCCAGACCTGTGC
GACGATGACATTGAGAAAATCTATTTGGACAAGTCGCGCTTCTTTAAACT
GATGCGCGTTTGTATGCGCCTGATTGACGACATTAATGACTTCGAGGATG
AGCGCTTGCACGGCAAGATTGCAAGCGCGATTGCATGCTACAAGGGTGAT
CATCCGAATTGCAGCGAATCCGAGGCAATCAACCAGATCATTACTCTGAA
CAATAAACTGCTGCGTGAACTGACGCGTGAGTTCTTTAAGAGCAATATGA
ATTTTCTGGAATGGCAGAAGATTTGTGTTAACTCCACCCGTGGCGTTCAG
TTCTTCTACATCTTCCGTGACGGTTTCACCTACAGCCACAAAGAAATCAA
ACAGCAAATCTTCAAAATCCTGGTGGACCCGATCAAGATGTAA
```
SEQ ID NO: 13
Por B1, amino acid sequence
```
MSNLMGDHISSLSSIPSNAFNQWDDAFIQSMETPYGEPEYRERAETLAKE
IKIFLKDMQSGGGDGDLIERLEIVDALQCLGIDRYFQAEIKAALDYVYNC
WDESVGIGLGSQSATKDLNATALALRVFRLNRYDVSADTLKYFKDNNGRF
VLCGDNKDNNDEDNSKEEKVMRSMLNLLRLSSLAFPAEIVMEEAKAFSSR
YLKELLGKSGDTSKKSFLKEVEYALIYEWPRTFIRWEARNFIEIYELDNE
RLKEKRILELAKLDFNILQFHYKLEMKNLSSWWVESEISKLIATRERSIE
YLLWAISSMDELEHSSSRIALAKITSLITILDDIFDDYATFEQLKCIRDA
IFKGWDVSIIENIPNNWKRCVEFVFKTIHQLTIDATDYQGRDMMPFVSKA
WEDYVEACFEQARWKLKGYFPTYNEYIKIAGKCVGFGPFSLHSAILASPN
LCDDDIQKIYLDKSRFYQLMRVAMRLIDDIHDFEEERLHGKMASAISCYM
ADHPNCSEKEAMNHIIELNNEVLKELTREFLKPSMIFHEWEKIFVNSTRG
VQFFYVHGDGFTYTHKEIKHQILKIIVDPIKI
```
SEQ ID NO: 14
Por2-3-5, amino acid sequence
```
MSTLEGDNIYSVSSLPAHAFNEWEDASVQSMEMSYGEPEYRERAETLVKE
VKILLKEMHTGDGDLIERLEMVDALQCLGIYRYFQAEIKQALDYVYSCWD
GNVGIGLGSESPTQHLNATALGIRVLRLHRYDVSADTLKNFKDKNGQFVL
CGGNNDNNDEEEKVMRSMLNLFRLSSVAIPGEMVLEEAKAFSSRYLKELL
```

ENSGDTVKRSFIKEVEYALTYEWPITFDRWEALNFIEIYDLNNERLMDKR

ILELAKLNFNILQFQYKLEMKNLSSWWAKSGISKLLAVRERSIEYLFWAI

TSVEELELSSSRIALVKCTTVITIVDDIFDDYATFEQLQCITDAISKDWD

VSLLENIPSNLKTSLEFVSKTIHELAMDATKYQGRDMMPFVTKAWLDYTN

ACFEQARWKVTGYFPSYNEYIKAAELSVAFGPILLHTALAASPILCDEDI

EKIYLDKSRFYHIMRVSMRLTDDIHDFEDERLHGKMASAISCYKGDHPNC

SEEEAINNIVTLNNELLKEMIREFFKPNSHYLEWEKICVNSTRGIGFFYI

FGDGFTYSHKEIKEQIFKIIVNPIKV

SEQ ID NO: 15
PorB1, coding DNA sequence (wild type)
ATGTCTAATTTGATGGGAGATCACATTTCTTCTCTTTCTTCCATTCCATC

CAATGCTTTCAATCAGTGGGACGATGCGTTTATTCAATCTATGGAGACGC

CATACGGGGAACCTGAATACCGTGAACGTGCTGAAACACTTGCTAAGGAA

ATAAAAATCTTTTTAAAAGACATGCAATCTGGAGGTGGAGATGGCGATCT

AATCGAGCGGCTTGAGATTGTTGACGCCTTGCAATGCCTCGGAATAGATC

GTTATTTTCAGGCTGAAATAAAAGCGGCTCTTGATTACGTTTATAACTGT

TGGGATGAAAGTGTGGGGATAGGATTAGGGAGCCAAAGTGCTACAAAGGA

TTTGAATGCTACAGCTTTAGCACTTCGAGTGTTTCGACTTAATCGTTATG

ATGTGTCTGCAGACACGTTGAAGTATTTCAAGGATAATAATGGGCGGTTC

GTACTCTGTGGAGACAATAAAGACAACAACGACGAGGATAATAGCAAAGA

AGAAAAAGTGATGAGAAGTATGCTCAACCTGTTAAGACTTTCCAGTTTGG

CATTTCCTGCAGAAATCGTTATGGAAGAGGCTAAAGCATTCAGTTCTAGA

TATCTTAAAGAACTATTAGGAAAATCTGGAGATACATCTAAGAAAAGTTT

TCTTAAAGAGGTGGAGTATGCCCTTATATATGAATGGCCTCGAACATTTA

TTAGATGGGAGGCACGAAATTTCATAGAAATCTATGAACTAGATAATGAG

AGGTTAAAAGAGAAAAGGATTTTAGAACTTGCGAAATTGGATTTTAACAT

ACTACAATTTCACTACAAGCTAGAGATGAAAAATCTCTCAAGTTGGTGGG

TTGAATCTGAAATCTCCAAGCTAATTGCAACAAGAGAACGATCCATTGAA

TATCTTTTGTGGGCAATTAGTTCTATGGATGAATTGGAGCATTCTAGTAG

TAGAATAGCTCTTGCAAAAATCACATCACTTATCACAATATTGGATGATA

TTTTTGATGACTATGCAACATTTGAGCAACTCAAATGCATTAGGGATGCC

ATTTTTAAAGGTTGGGATGTTTCTATCATAGAAAACATTCCCAACAACTG

GAAAAGATGCGTGGAATTTGTTTTAAAACAATTCATCAATTGACAATAG

ATGCTACTGATTATCAAGGGCGTGACATGATGCCTTTTGTTTCAAAAGCG

TGGGAAGATTATGTGGAAGCCTGCTTTGAGCAGGCACGATGGAAATTGAA

AGGATATTTTCCAACCTACAATGAGTACATAAAGATAGCTGGAAAATGTG

TAGGGTTTGGACCCTTTTCTTTACATTCTGCCATACTAGCATCTCCAAAT

TTATGTGATGATGATATTCAGAAGATATACCTTGATAAATCTAGATTTTA

TCAACTCATGCGAGTGGCTATGAGGTTAATTGATGATATACACGACTTTG

AGGAAGAGAGACTCCATGGAAAGATGGCCTCAGCTATTTCTTGTTATATG

GCTGATCATCCAAATTGTTCAGAGAAAGAGGCAATGAATCATATCATCGA

ACTAAATAATGAAGTATTGAAGGAATTGACAAGAGAATTTTTAAAACCAA

GTATGATATTTCATGAGTGGGAGAAGATATTTGTCAATTCTACTCGAGGA

GTACAATTTTTCTATGTACATGGTGATGGATTTACATATACGCATAAGGA

GATCAAGCATCAGATACTAAAAATTATTGTCGATCCAATAAAAATCTAG

SEQ ID NO: 16
Por2-3-5, coding DNA sequence (wild type)
ATGTCGACTTTGGAAGGAGACAACATTTATTCTGTTTCTTCCTTACCAGC

CCATGCTTTTAATGAGTGGGAAGATGCTTCTGTTCAATCTATGGAGATGT

CATACGGGGAACCTGAATACCGTGAACGTGCTGAAACACTTGTGAAAGAA

GTAAAAATCTTGTTGAAAGAAATGCACACTGGAGATGGCGATCTAATCGA

GCGGCTTGAGATGGTTGATGCATTGCAATGCCTTGGAATTTATCGATACT

TTCAGGCTGAGATTAAACAAGCTCTTGATTACGTTTACAGCTGCTGGGAT

GGAAATGTGGGGATAGGATTAGGCTCCGAGAGTCCTACACAGCATTTGAA

TGCCACAGCTTTGGGAATCAGAGTACTGCGACTCCATCGTTATGATGTGT

CTGCAGACACGTTGAAGAATTTCAAGGACAAAAATGGGCAGTTCGTACTC

TGTGGAGGAAATAATGACAATAACGATGAGGAAGAGAAAGTGATGAGAAG

TATGCTCAACCTGTTCAGACTTTCCAGTGTGGCAATTCCTGGAGAAATGG

TTCTGGAAGAGGCTAAAGCATTTAGCAGTAGATATCTTAAAGAATTATTA

GAAAATTCTGGAGATACAGTTAAGAGAAGTTTTATTAAAGAGGTGGAGTA

TGCTCTTACCTATGAATGGCCTATAACTTTTGATAGATGGGAGGCACTGA

ATTTCATAGAAATCTATGATTTAAATAATGAGAGGTTGATGGACAAAAGG

ATATTAGAGCTTGCAAAATTGAATTTTAATATACTACAATTTCAATACAA

GTTGGAGATGAAAAATCTCTCAAGTTGGTGGGCTAAATCTGGCATCTCGA

AACTACTTGCAGTAAGGGAGCGATCCATTGAATATCTTTTTTGGGCAATT

ACTTCTGTAGAAGAATTGGAGCTTTCTAGTAGTAGAATAGCTCTTGTAAA

GTGCACAACAGTTATTACAATAGTGGATGATATTTTTGATGACTATGCAA

CATTTGAGCAACTCCAATGTATTACAGATGCTATCTCTAAAGATTGGGAT

GTTTCTCTTTTAGAAAACATTCCCAGCAACTTGAAGACAAGCTTGGAATT

TGTTTCAAAAACAATTCATGAGTTGGCAATGGATGCTACTAAATATCAAG

GGCGTGACATGATGCCTTTTGTTACAAAAGCGTGGTTAGATTACACGAAC

GCCTGCTTTGAGCAAGCACGATGGAAAGTGACTGGTTATTTTCCAAGCTA

CAATGAGTACATAAAGGCTGCTGAATTAAGTGTAGCATTTGGACCGATAT

TGTTACATACTGCCCTAGCAGCATCTCCTATTTTATGCGATGAAGATATT

GAGAAGATATACCTTGATAAATCTAGATTCTATCATATCATGCGAGTGTC

TATGCGGTTGACTGATGATATACATGATTTTGAGGATGAGAGGCTGCATG

GAAAGATGGCTTCAGCTATTTCTTGTTATAAGGGTGATCATCCAAATTGT

TCAGAAGAAGAGGCAATAAATAATATTGTCACCCTCAATAATGAATTATT

GAAGGAAATGATAAGGGAATTTTTTAAACCAAATAGTCATTATCTTGAAT

GGGAAAAGATATGTGTCAATAGTACTAGAGGAATAGGATTTTTCTATATA

TTTGGAGATGGGTTTACATATTCTCACAAGGAAATCAAGGAGCAGATATT

TAAAATTATTGTTAATCCAATAAAAGTGTAG

SEQ ID NO: 17
PorB1, coding DNA sequence (optimised by
Genscript genetic codon frequency of E. coli)
ATGTCCAACCTGATGGGCGATCATATTAGCTCTCTGAGTTCCATCCCGTC

CAACGCTTTTAATCAGTGGGATGACGCGTTCATTCAATCAATGGAAACCC

CGTATGGTGAACCGGAATACCGTGAACGCGCTGAAACGCTGGCGAAAGAA

ATCAAAATCTTCCTGAAAGATATGCAGTCTGGCGGTGGCGACGGCGATCT

GATTGAACGTCTGGAAATCGTGGACGCCCTGCAGTGCCTGGGTATTGATC

GCTATTTTCAAGCAGAAATCAAAGCGGCCCTGGACTATGTTTACAACTGT

TGGGATGAATCGGTCGGTATTGGCCTGGGTTCCCAATCAGCCACCAAAGA

TCTGAACGCAACGGCTCTGGCGCTGCGTGTGTTTCGCCTGAATCGTTATG

ACGTTTCTGCGGATACCCTGAAATACTTCAAAGATAACAACGGCCGTTTC

GTTCTGTGCGGTGACAACAAAGATAACAACGACGAAGATAACTCTAAAGA

AGAAAAAGTCATGCGTAGTATGCTGAATCTGCTGCGCCTGTCATCGCTGG

CTTTCCCGGCGGAAATTGTCATGGAAGAAGCCAAAGCATTTAGCTCTCGC

TATCTGAAAGAACTGCTGGGCAAAAGCGGTGATACCAGCAAAAAATCTTT

TCTGAAAGAAGTGGAATACGCCCTGATTTACGAATGGCCGCGCACGTTCA

TCCGTTGGGAAGCACGCAACTTCATCGAAATCTACGAACTGGACAACGAA

CGTCTGAAAGAAAAACGCATTCTGGAACTGGCGAAACTGGATTTTAACAT

CCTGCAGTTCCATTACAAACTGGAAATGAAAAACCTGAGTTCCTGGTGGG

TGGAATCTGAAATTAGTAAACTGATCGCTACCCGTGAACGCTCCATTGAA

TATCTGCTGTGGGCGATCTCATCGATGGATGAACTGGAACACAGCTCTAG

TCGTATTGCTCTGGCGAAAATCACCTCACTGATTACGATCCTGGATGACA

TTTTTGATGACTACGCTACCTTCGAACAGCTGAAATGCATTCGTGACGCG

ATCTTCAAAGGCTGGGATGTTAGTATTATCGAAAACATCCCGAACAATTG

GAAACGCTGTGTGGAATTTGTTTTCAAAACGATTCATCAGCTGACCATCG

ACGCTACGGATTATCAAGGTCGTGACATGATGCCGTTTGTCAGCAAAGCA

TGGGAAGATTATGTGGAAGCCTGTTTCGAACAGGCACGCTGGAAACTGAA

AGGCTACTTTCCGACCTATAACGAATACATTAAAATCGCCGGTAAATGCG

TTGGCTTTGGTCCGTTCTCCCTGCACTCAGCCATTCTGGCATCTCCGAAT

CTGTGTGATGACGATATCCAGAAAATCTACCTGGATAAAGTCGTTTCTA

CCAACTGATGCGTGTCGCGATGCGCCTGATTGACGATATCCATGATTTTG

AAGAAGAACGCCTGCACGGCAAAATGGCCTCGGCAATTAGCTGCTATATG

GCCGATCATCCGAACTGTAGCGAAAAAGAAGCAATGAATCACATTATCGA

ACTGAACAATGAAGTGCTGAAAGAACTGACCCGTGAATTTCTGAAACCGT

CGATGATCTTCCATGAATGGGAAAAAATCTTCGTTAACAGCACGCGCGGT

GTCCAGTTTTTCTATGTGCACGGCGACGGTTTCACCTACACGCATAAAGA

AATCAAACACCAAATCCTGAAAATTATCGTTGATCCGATTAAAATCTAA

SEQ ID NO: 18
PorB1, coding DNA sequence (optimised by
DNA2.0 genetic codon frequency of E. coli)
ATGTCTAATTTGATGGGTGATCACATTTCGAGCCTGAGCAGCATTCCGAG

CAACGCATTCAATCAGTGGGATGACGCATTCATCCAGTCGATGGAAACCC

CGTATGGTGAGCCGGAGTACCGTGAGCGTGCGGAAACCCTGGCAAAAGAA

ATCAAGATTTTTCTGAAAGACATGCAGAGCGGCGGCGGCGATGGCGATCT

GATCGAGCGTTTGGAAATCGTGGATGCGCTGCAATGCCTGGGTATCGACC

GTTACTTCCAAGCCGAGATCAAAGCTGCCCTGGACTACGTTTATAATTGT

TGGGACGAGTCTGTTGGCATTGGTCTGGGTAGCCAGAGCGCCACTAAAGA

TCTGAACGCAACGGCGCTGGCGCTCCGTGTTTTCCGCTTGAACCGTTACG

ACGTCAGCGCGGACACCTTAAAGTATTTCAAAGATAACAACGGTCGTTTT

GTGCTGTGTGGCGATAATAAAGACAACAATGACGAAGATAACAGCAAAGA

AGAAAAAGTCATGCGCAGCATGCTGAATTTGCTGCGCCTGAGCAGCCTGG

CGTTTCCTGCTGAGATTGTCATGGAAGAAGCAAAGGCCTTTAGCTCTCGT

TATCTGAAAGAACTGCTGGGTAAGAGCGGCGATACCAGCAAAAAGTCGTT

TTTGAAAGAAGTGGAGTACGCACTGATTTATGAGTGGCCGCGTACCTTCA

TCCGCTGGGAGGCACGCAACTTTATCGAGATCTACGAACTGGACAACGAA

CGCCTGAAAGAAAAGCGTATCTTGGAACTGGCGAAACTGGACTTCAACAT

TCTGCAGTTCCACTATAAACTGGAGATGAAGAATTTGTCCTCCTGGTGGG

TGGAGTCCGAGATCAGCAAGCTGATTGCGACGCGTGAGCGTAGCATTGAG

TATCTGCTGTGGGCTATTAGCAGCATGGACGAACTGGAGCACTCCAGCAG

CCGTATCGCCCTGGCGAAGATTACCTCTCTGATTACCATTCTGGATGATA

TTTTTGACGACTACGCGACCTTTGAGCAACTGAAGTGCATCCGCGACGCC

ATCTTCAAGGGCTGGGATGTTAGCATCATTGAGAACATCCCGAACAATTG

GAAACGTTGTGTTGAATTTGTCTTTAAGACGATTCATCAACTGACCATCG

ACGCTACGGACTACCAGGGTCGCGACATGATGCCGTTCGTGAGCAAAGCG

TGGGAAGATTATGTTGAGGCGTGCTTCGAGCAAGCGCGTTGGAAGCTGAA

GGGTTACTTTCCGACGTACAACGAATACATCAAGATCGCGGGTAAATGCG

TCGGTTTCGGTCCATTCTCCCTTCATAGCGCGATTTTGGCGAGCCCGAAC

CTGTGCGATGACGACATCCAAAAGATCTATCTGGATAAGAGCCGTTTTTA

TCAATTGATGCGCGTCGCGATGCGTCTGATTGACGACATTCACGACTTTG

AAGAGGAACGCCTGCACGGTAAAATGGCCTCCGCGATCAGCTGCTACATG

GCAGATCACCCGAACTGTTCAGAGAAAGAGGCAATGAACCACATTATTGA

GTTGAATAATGAAGTCCTGAAAGAACTGACCCGTGAGTTCCTGAAACCGA

GCATGATCTTCCATGAGTGGGAAAAGATCTTTGTGAATAGCACGCGCGGT

GTGCAATTCTTTTACGTTCACGGCGATGGCTTCACCTACACGCATAAAGA

AATCAAGCATCAGATTCTGAAGATTATCGTGGACCCGATTAAGATTTAA

SEQ ID NO: 19
Por2-3-5, coding DNA sequence (optimised by
Genscript genetic codon frequency of E. coli)
ATGAGCACCCTGGAAGGCGACAACATCTACAGCGTGAGCAGCCTGCCGGC

GCACGCGTTCAACGAGTGGGAAGATGCGAGCGTTCAGAGCATGGAGATGA

GCTACGGTGAACCGGAATATCGTGAGCGTGCGGAAACCCTGGTGAAGGAA

GTTAAAATCCTGCTGAAGGAGATGCACACCGGTGACGGCGATCTGATTGA

GCGTCTGGAAATGGTGGACGCGCTGCAATGCCTGGGCATCTACCGTTATT

TTCAGGCGGAAATTAAACAAGCGCTGGACTACGTGTATAGCTGCTGGGAT

GGCAACGTTGGTATCGGTCTGGGTAGCGAGAGCCCGACCCAGCACCTGAA

-continued

```
CGCGACCGCGCTGGGTATTCGTGTGCTGCGTCTGCACCGTTACGACGTTA
GCGCGGATACCCTGAAGAACTTCAAGGATAAAAACGGTCAATTTGTGCTG
TGCGGTGGCAACAACGACAACAACGATGAGGAAGAGAAAGTTATGCGTAG
CATGCTGAACCTGTTCCGTCTGAGCAGCGTGGCGATCCCGGGTGAAATGG
TTCTGGAAGAGGCGAAGGCGTTTAGCAGCCGTTATCTGAAAGAGCTGCTG
GAAAACAGCGGTGACACCGTGAAGCGTAGCTTCATCAAAGAGGTTGAATA
CGCGCTGACCTATGAGTGGCCGATTACCTTCGATCGTTGGGAAGCGCTGA
ACTTTATCGAGATTTACGACCTGAACAACGAACGTCTGATGGATAAGCGT
ATCCTGGAGCTGGCGAAACTGAACTTCAACATTCTGCAGTTTCAATATAA
GCTGGAAATGAAAAACCTGAGCTCCTGGTGGGCGAAGAGCGGCATCAGCA
AACTGCTGGCGGTTCGTGAGCGTAGCATCGAATACCTGTTTTGGGCGATT
ACCAGCGTGGAAGAGCTGGAGCTGAGCAGCAGCCGTATCGCGCTGGTTAA
GTGCACCACCGTGATCACCATTGTTGACGATATTTTCGACGATTATGCGA
CCTTTGAACAGCTGCAATGCATCACCGACGCGATTAGCAAAGACTGGGAT
GTGAGCCTGCTGGAGAACATCCCGAGCAACCTGAAGACCAGCCTGGAATT
CGTTAGCAAAACCATTCACGAGCTGGCGATGGACGCGACCAAGTACCAGG
GTCGTGATATGATGCCGTTTGTGACCAAAGCGTGGCTGGATTACACCAAC
GCGTGCTTCGAGCAAGCGCGTTGGAAGGTGACCGGCTATTTTCCGAGCTA
CAACGAATATATCAAAGCGGCGGAGCTGAGCGTTGCGTTCGGTCCGATCC
TGCTGCACACCGCGCTGGCGGCGAGCCCGATTCTGTGCGACGAGGATATC
GAAAAGATTTACCTGGACAAAAGCCGTTTCTATCACATCATGCGTGTTAG
CATGCGTCTGACCGACGATATTCACGACTTTGAGGATGAACGTCTGCACG
GCAAGATGGCGAGCGCGATTAGCTGCTACAAAGGTGATCACCCGAACTGC
AGCGAAGAGGAAGCGATCAACAACATTGTGACCCTGAACAACGAGCTGCT
GAAGGAAATGATCCGTGAGTTCTTTAAACCGAACAGCCACTATCTGGAGT
GGGAAAAGATTTGCGTTAACAGCACCCGTGGCATCGGTTTCTTTTACATT
TTCGGCGACGGTTTTACCTATAGCCACAAGGAGATCAAAGAACAGATTTT
CAAGATCATTGTGAACCCGATCAAAGTTTAA
```

```
                                          SEQ ID NO: 20
Forward primer
TTTAAGTGCTTCTGCGATG SEQ ID NO: 21
Reverse primer
ACATCTAGGTTTGTGCCTT SEQ ID NO: 22
Gene specific reverse primer
ATCGCCATCTCCAGTGTG SEQ ID NO: 23
Forward primer
CTTTAGTGCTTCTGTGATG SEQ ID NO: 24
Reverse primer
CATACAAGTTTGTGCCTCA
```

The invention claimed is:

1. A method of producing one or more sesquiterpenes comprising (+)-cedrol and/or (−)-thujopsene, the method comprising:
   a. contacting an acyclic farnesyl diphosphate (FPP) precursor with a polypeptide having a (+)-cedrol synthase activity and/or a (−)-thujopsene synthase activity wherein the polypeptide comprises:
      i. a sequence of amino acids that has at least 90% sequence identity to a polypeptide selected from the group consisting of SEQ ID NO:1, SEQ ID NO:2, SEQ ID NO:3, SEQ ID NO:4, SEQ ID NO: 13 and SEQ ID NO: 14; or
      ii. a sequence of amino acids selected from the group consisting of SEQ ID NO:1, SEQ ID NO:2, SEQ ID NO:3, SEQ ID NO:4, SEQ ID NO: 13 and SEQ ID NO: 14,
         to produce one or more sesquiterpenes comprising (+)-cedrol and/or (−)-thujopsene; and
   b. optionally isolating the (+)-cedrol and/or (−)-thujopsene.

2. The method as recited in claim 1 further comprising transforming a host cell or non-human host organism with a nucleic acid encoding a polypeptide having a (+)-cedrol and/or (−)-thujopsene activity wherein the polypeptide comprises:
   a. a sequence of amino acids that has at least 90% sequence identity to SEQ ID NO:1, SEQ ID NO:2, SEQ ID NO:3, SEQ ID NO:4, SEQ ID NO: 13 or SEQ ID NO: 14; or
   b. a sequence of amino acids comprising SEQ ID NO:1, SEQ ID NO:2, SEQ ID NO:3, SEQ ID NO:4, SEQ ID NO: 13 or SEQ ID NO: 14,
   and wherein the method further comprises culturing the host cell or organism under conditions that allow for the production of the polypeptide.

3. The method as recited in claim 1 further comprising cultivating a non-human host organism or cell capable of producing FPP and transformed to express a polypeptide wherein the polypeptide comprises:
   a. a sequence of amino acids that has at least 90% sequence identity to SEQ ID NO:1, SEQ ID NO:2, SEQ ID NO:3, SEQ ID NO:4, SEQ ID NO: 13 or SEQ ID NO: 14; or
   b. a sequence of amino acids comprising SEQ ID NO:1, SEQ ID NO:2, SEQ ID NO:3, SEQ ID NO:4, SEQ ID NO: 13 or SEQ ID NO: 14, and wherein said cultivating is done under conditions conducive to the production of (+)-cedrol or (−)-thujopsene.

4. The method as recited in claim 3, wherein the cell is a prokaryotic cell, a bacterial cell, or a eukaryotic cell.

5. The method as recited in claim 4, wherein the eukaryotic cell is a yeast cell or a plant cell.

6. The method of claim 1 further comprising processing the (+)-cedrol to a derivative using a chemical or biochemical synthesis or a combination of both.

7. The method of claim 1 further comprising contacting the (+)-cedrol with at least one enzyme to produce a (+)-cedrol derivative.

8. The method of claim 1 further comprising converting the (−)-thujopsene to a (−)-thujopsene derivative using a chemical or biochemical synthesis or a combination of both.

9. The method of claim 1 further comprising contacting the (−)-thujopsene with at least one enzyme to produce a thujopsene derivative.

10. The method of claim 1, wherein the polypeptide comprises:
   a. a sequence of amino acids that has at least 90% 95% sequence identity to SEQ ID NO:1, SEQ ID NO:2, SEQ ID NO:3, or SEQ ID NO: 13; or
   b. a sequence of amino acids comprising SEQ ID NO:1, SEQ ID NO:2, SEQ ID NO:3, or SEQ ID NO: 13,
   and wherein the main sesquiterpene compound produced is (+)-cedrol.

11. The method of claim 1, wherein the polypeptide comprises:
   a. a sequence of amino acids that has at least 90% sequence identity to SEQ ID NO:4 or SEQ ID NO: 14; or
   b. a sequence of amino acids comprising SEQ ID NO:4 or SEQ ID NO: 14,
   and wherein the main sesquiterpene compound produced is (−)-thujopsene.

* * * * *

SEQUENCE LISTING

<160> NUMBER OF SEQ ID NOS: 24

<210> SEQ ID NO 1
<211> LENGTH: 580
<212> TYPE: PRT
<213> ORGANISM: Juniperus virginiana

<400> SEQUENCE: 1

```
Met Ser Asn Leu Lys Gly Asp His Ile Ser Ser Val Ser Ile Pro
1               5                  10                  15

Ala His Ala Phe Asn Glu Trp Gly Asp Ala Phe Val Gln Ser Met Glu
                20                  25                  30

Met Pro Tyr Gly Glu Pro Glu Tyr Arg Glu Arg Ala Glu Thr Leu Val
                35                  40                  45

Lys Gln Val Lys Ile Leu Leu Lys Glu Met Gln Thr Gly Asp Gly Asp
        50                  55                  60

Leu Ile Glu Arg Leu Glu Met Val Asp Ala Leu Gln Cys Leu Gly Ile
65                  70                  75                  80

Glu Arg Tyr Phe Gln Ala Glu Ile Lys Glu Ala Leu Asp Tyr Val Tyr
                85                  90                  95

Arg Ser Trp Asp Gly Thr Val Gly Ile Gly Leu Gly Cys Asn Ser Ala
                100                 105                 110

Thr Lys His Leu Asn Ala Thr Ala Leu Gly Leu Arg Val Leu Arg Leu
        115                 120                 125

His Arg Tyr Asp Val Ser Pro Asp Thr Leu Tyr Asn Phe Lys Asp Asn
        130                 135                 140
```

-continued

```
Thr Gly Glu Phe Val Leu Cys Gly Glu Asn Lys Val Ser Asn Asp Glu
145                 150                 155                 160

Asp Thr Asn Lys Glu Glu Lys Val Met Arg Ser Met Leu Asn Leu Leu
                165                 170                 175

Arg Leu Ser Ser Leu Ala Phe Pro Gly Glu Ile Ile Met Glu Glu Ala
            180                 185                 190

Gln Ala Phe Ser Thr Arg Tyr Leu Lys Glu Leu Leu Glu Ile Ser Gly
        195                 200                 205

Asp Thr Phe Asn Arg Ser Phe Ile Lys Glu Val Glu Tyr Ala Leu Thr
    210                 215                 220

Tyr Glu Trp Pro Arg Thr Phe Thr Arg Trp Glu Ala Trp Asn Phe Ile
225                 230                 235                 240

Glu Ile Cys Asp Leu Asp Asn Asp Arg Leu Glu Asp Lys Arg Ile Leu
                245                 250                 255

Gln Leu Ala Lys Leu Asp Phe Asn Ile Leu Gln Phe Gln Tyr Lys Leu
            260                 265                 270

Glu Met Lys Asn Leu Ser Ser Trp Trp Val Ser Gly Ile Ser Asn
        275                 280                 285

Leu Val Ala Thr Arg Ala Arg His Ile Glu Tyr Leu Phe Trp Ala Val
    290                 295                 300

Ala Ser Thr Asp Glu Met Glu Phe Ser Ser Arg Ile Ala Leu Ala
305                 310                 315                 320

Lys Thr Thr Ala Ile Ile Thr Val Met Asp Asp Ile Phe Asp Asp Tyr
                325                 330                 335

Ala Thr Leu Glu Tyr Leu Lys Cys Ile Ser Asp Ala Ile Ser Lys Asn
            340                 345                 350

Trp Asp Val Ser Ile Ile Glu Asn Ile Pro Asn Asn Leu Lys Thr Cys
        355                 360                 365

Phe Glu Phe Ile Ser Lys Thr Val His Gln Met Ala Ile Asp Ala Thr
    370                 375                 380

Lys Tyr Gln Gly Arg Asp Met Met Pro Phe Ile Thr Lys Ala Trp Ala
385                 390                 395                 400

Asp Tyr Ile Glu Ala Cys Phe Glu Glu Ala Arg Trp Lys Leu Thr Gly
                405                 410                 415

Tyr Phe Pro Thr Tyr Asp Glu Tyr Met Lys Ser Ala Glu Leu Cys Val
            420                 425                 430

Gly Phe Gly Gln Ile Phe Leu Ser Ser Gly Leu Leu Ala Ser Pro Asn
        435                 440                 445

Leu Cys Asp Asp Ile Glu Lys Ile Tyr Leu Asp Lys Ser Arg Phe
    450                 455                 460

Phe Lys Leu Met Arg Val Cys Met Arg Leu Ile Asp Asp Ile Asn Asp
465                 470                 475                 480

Phe Glu Asp Glu Arg Leu His Gly Lys Ile Ala Ser Ala Ile Ala Cys
                485                 490                 495

Tyr Lys Gly Asp His Pro Asn Cys Ser Glu Ser Glu Ala Ile Asn Gln
            500                 505                 510

Ile Ile Thr Leu Asn Asn Lys Leu Leu Arg Glu Leu Thr Arg Glu Phe
        515                 520                 525

Phe Lys Ser Asn Met Asn Phe Leu Glu Trp Gln Lys Ile Cys Val Asn
    530                 535                 540

Ser Thr Arg Gly Val Gln Phe Phe Tyr Ile Phe Arg Asp Gly Phe Thr
545                 550                 555                 560

Tyr Ser His Lys Glu Ile Lys Gln Gln Ile Phe Lys Ile Leu Val Asp
```

Pro Ile Lys Met
            580

<210> SEQ ID NO 2
<211> LENGTH: 580
<212> TYPE: PRT
<213> ORGANISM: Juniperus virginiana

<400> SEQUENCE: 2

Met Ser Asn Leu Lys Gly Asp His Ile Ser Val Ser Ser Ile Pro
1               5                   10                  15

Ala His Ala Phe Asn Glu Trp Gly Asp Ala Phe Val Gln Ser Met Glu
                20                  25                  30

Met Pro Tyr Gly Glu Pro Glu Tyr Arg Glu Arg Ala Glu Thr Leu Val
            35                  40                  45

Lys Gln Val Lys Ile Leu Leu Lys Glu Met Gln Thr Gly Asp Gly Asp
        50                  55                  60

Leu Ile Glu Arg Leu Glu Met Val Asp Ala Leu Gln Cys Leu Gly Ile
65                  70                  75                  80

Glu Arg Tyr Phe Gln Ala Glu Ile Lys Glu Ala Leu Asp Tyr Val Tyr
                85                  90                  95

Arg Ser Trp Asp Gly Thr Val Gly Ile Gly Leu Gly Cys Asn Ser Ala
            100                 105                 110

Thr Lys His Leu Asn Ala Thr Ala Leu Gly Leu Arg Val Leu Arg Leu
        115                 120                 125

His Arg Tyr Asp Val Ser Pro Asp Thr Leu His Asn Phe Lys Asp Asn
            130                 135                 140

Thr Gly Lys Phe Val Leu Thr Gly Glu Asn Lys Asp Asn Asn Asp Glu
145                 150                 155                 160

Asp Thr Asn Lys Glu Glu Lys Val Met Arg Ser Ile Leu Asn Leu Phe
                165                 170                 175

Arg Leu Ser Ser Leu Ala Phe Pro Gly Glu Ile Ile Met Glu Glu Ala
            180                 185                 190

Lys Ala Phe Ser Thr Arg Tyr Leu Lys Glu Leu Leu Glu Ile Ser Arg
        195                 200                 205

Asp Thr Phe Asn Arg Ser Phe Ile Lys Glu Val Glu Tyr Ala Leu Thr
            210                 215                 220

Tyr Glu Trp Pro Arg Thr Phe Thr Arg Trp Glu Ala Trp Asn Phe Ile
225                 230                 235                 240

Glu Ile Cys Asp Leu Asp Asn Asp Arg Leu Glu Asp Lys Arg Ile Leu
                245                 250                 255

Gln Leu Ala Lys Leu Asp Phe Asn Ile Leu Gln Phe Gln Tyr Lys Leu
            260                 265                 270

Glu Met Lys Asn Leu Ser Ser Trp Trp Val Glu Ser Gly Ile Ser Asn
        275                 280                 285

Leu Val Ala Thr Arg Ala Arg His Ile Glu Tyr Leu Phe Trp Ala Val
            290                 295                 300

Ala Ser Thr Asp Glu Met Glu Phe Ser Ser Arg Ile Ala Leu Ala
305                 310                 315                 320

Lys Thr Thr Ala Ile Ile Thr Val Met Asp Asp Ile Phe Asp Tyr
                325                 330                 335

Ala Thr Leu Glu Tyr Leu Lys Cys Ile Ser Asp Ala Ile Ser Lys Asn
            340                 345                 350

```
Trp Asp Val Ser Ile Ile Glu Asn Ile Pro Asn Asn Leu Lys Thr Cys
            355                 360                 365

Phe Glu Phe Ile Ser Lys Thr Val His Gln Met Ala Ile Asp Ala Thr
    370                 375                 380

Lys Tyr Gln Gly Arg Asp Met Met Pro Phe Ile Thr Lys Ala Trp Ala
385                 390                 395                 400

Asp Tyr Ile Glu Ala Cys Phe Glu Glu Ala Arg Trp Lys Leu Thr Gly
                405                 410                 415

Tyr Phe Pro Thr Tyr Asp Glu Tyr Met Lys Ser Ala Glu Leu Cys Val
            420                 425                 430

Gly Phe Gly Gln Ile Phe Leu Ser Ser Gly Leu Leu Ala Ser Pro Asn
        435                 440                 445

Leu Cys Asp Asp Asp Ile Glu Lys Ile Tyr Leu Asp Lys Ser Arg Phe
    450                 455                 460

Phe Lys Leu Met Arg Val Cys Met Arg Leu Ile Asp Asp Ile Asn Asp
465                 470                 475                 480

Phe Glu Asp Glu Arg Leu His Gly Lys Ile Ala Ser Ala Ile Ala Cys
                485                 490                 495

Tyr Lys Gly Asp His Pro Asn Cys Ser Glu Ser Glu Ala Ile Asn Gln
            500                 505                 510

Ile Val Met Leu Asn Asn Lys Leu Leu Arg Glu Leu Thr Arg Glu Phe
        515                 520                 525

Leu Lys Ser Asn Met Asn Phe Leu Glu Trp Glu Lys Ile Cys Val Asn
    530                 535                 540

Ser Thr Arg Gly Val Gln Phe Cys Tyr Ile Phe Gly Asp Gly Phe Thr
545                 550                 555                 560

Tyr Ser His Lys Glu Ile Lys Gln Gln Ile Phe Lys Ile Leu Val Asn
                565                 570                 575

Pro Ile Lys Val
            580

<210> SEQ ID NO 3
<211> LENGTH: 580
<212> TYPE: PRT
<213> ORGANISM: Juniperus virginiana

<400> SEQUENCE: 3

Met Ser Asn Leu Lys Gly Asp His Ile Ser Val Ser Ser Ile Pro
1               5                   10                  15

Ala His Ala Phe Asn Glu Trp Gly Asp Ala Phe Val Gln Ser Met Glu
                20                  25                  30

Met Pro Tyr Gly Glu Pro Glu Tyr Arg Glu Arg Ala Glu Thr Leu Val
            35                  40                  45

Lys Gln Val Lys Ile Leu Leu Lys Glu Met Gln Thr Gly Asp Gly Asp
        50                  55                  60

Leu Ile Glu Arg Leu Glu Met Val Asp Ala Leu Gln Cys Leu Gly Ile
65                  70                  75                  80

Glu Arg Tyr Phe Gln Ala Glu Ile Lys Glu Ala Leu Asp Tyr Val Tyr
                85                  90                  95

Arg Ser Trp Asp Gly Thr Val Gly Ile Gly Leu Gly Cys Asn Ser Ala
            100                 105                 110

Thr Lys His Leu Asn Ala Thr Ala Leu Gly Leu Arg Val Leu Arg Leu
        115                 120                 125

His Arg Tyr Asp Val Ser Pro Asp Thr Leu His Asn Phe Lys Asp Asn
    130                 135                 140
```

```
Thr Gly Lys Phe Val Leu Thr Gly Glu Asn Lys Asp Asn Asp Glu
145                 150                 155                 160

Asp Thr Asn Lys Glu Lys Val Met Arg Ser Ile Leu Asn Leu Phe
                165                 170                 175

Arg Leu Ser Ser Leu Ala Phe Pro Gly Glu Ile Ile Met Glu Glu Ala
            180                 185                 190

Lys Ala Phe Ser Thr Arg Tyr Leu Lys Glu Leu Leu Glu Ile Ser Arg
            195                 200                 205

Asp Thr Phe Asn Arg Ser Phe Ile Lys Glu Val Glu Tyr Ala Leu Thr
            210                 215                 220

Tyr Glu Trp Pro Arg Thr Phe Thr Arg Trp Glu Ala Trp Asn Phe Ile
225                 230                 235                 240

Glu Ile Cys Asp Leu Asp Asn Asp Arg Leu Glu Asp Lys Arg Ile Leu
                245                 250                 255

Gln Leu Ala Lys Leu Asp Phe Asn Ile Leu Gln Phe Gln Tyr Lys Leu
            260                 265                 270

Glu Met Lys Asn Leu Ser Ser Trp Val Glu Ser Gly Ile Ser Asn
            275                 280                 285

Leu Val Ala Thr Arg Ala Arg His Ile Glu Tyr Leu Phe Trp Ala Val
            290                 295                 300

Ala Ser Thr Asp Glu Met Glu Phe Ser Ser Arg Ile Ala Leu Ala
305                 310                 315                 320

Lys Thr Thr Ala Ile Ile Thr Val Met Asp Asp Ile Phe Asp Tyr
                325                 330                 335

Ala Thr Leu Glu Tyr Leu Lys Cys Ile Ser Asp Ala Ile Ser Lys Asn
            340                 345                 350

Trp Asp Val Ser Ile Ile Glu Asn Ile Pro Asn Asn Leu Lys Thr Cys
            355                 360                 365

Phe Glu Phe Ile Ser Lys Thr Val His Gln Met Ala Ile Asp Ala Thr
370                 375                 380

Lys Tyr Gln Gly Arg Asp Met Met Pro Phe Ile Thr Lys Ala Trp Ala
385                 390                 395                 400

Asp Tyr Ile Glu Ala Cys Phe Glu Glu Ala Arg Trp Lys Leu Thr Gly
                405                 410                 415

Tyr Phe Pro Thr Tyr Asp Glu Tyr Met Lys Ser Ala Glu Leu Cys Val
            420                 425                 430

Gly Phe Gly Gln Ile Phe Leu Ser Ser Gly Leu Leu Ala Ser Pro Asn
            435                 440                 445

Leu Cys Asp Asp Asp Ile Glu Lys Ile Tyr Leu Asp Lys Ser Arg Phe
            450                 455                 460

Phe Lys Leu Met Arg Val Cys Met Arg Leu Ile Asp Asp Ile Asn Asp
465                 470                 475                 480

Phe Glu Asp Glu Arg Leu His Gly Lys Ile Ala Ser Ala Ile Ala Cys
                485                 490                 495

Tyr Lys Gly Asp His Pro Asn Cys Ser Glu Ser Glu Ala Ile Asn Gln
            500                 505                 510

Ile Ile Thr Leu Asn Asn Lys Leu Leu Arg Glu Leu Thr Arg Glu Phe
            515                 520                 525

Phe Lys Ser Asn Met Asn Phe Leu Glu Trp Gln Lys Ile Cys Val Asn
            530                 535                 540

Ser Thr Arg Gly Val Gln Phe Pro Tyr Ile Phe Arg Asp Gly Phe Thr
545                 550                 555                 560
```

Tyr Ser His Lys Glu Ile Lys Gln Gln Ile Phe Lys Ile Leu Val Asp
                565                 570                 575
Pro Ile Lys Met
            580

<210> SEQ ID NO 4
<211> LENGTH: 580
<212> TYPE: PRT
<213> ORGANISM: Juniperus virginiana

<400> SEQUENCE: 4

Met Ser Asn Leu Lys Gly Asp His Ile Ser Val Ser Ser Ile Pro
1               5                   10                  15

Ala His Ala Phe Asn Glu Trp Gly Asp Ala Phe Val Gln Ser Met Glu
                20                  25                  30

Met Pro Tyr Gly Glu Pro Glu Tyr Arg Glu Arg Ala Glu Thr Leu Val
                35                  40                  45

Lys Gln Val Lys Ile Leu Leu Lys Glu Met Gln Thr Gly Asp Gly Asp
50                  55                  60

Leu Ile Glu Arg Leu Glu Met Val Asp Ala Leu Gln Cys Leu Gly Ile
65                  70                  75                  80

Glu Arg Tyr Phe Gln Ala Glu Ile Lys Glu Ala Leu Asp Tyr Val Tyr
                85                  90                  95

Arg Ser Trp Asp Gly Thr Val Gly Ile Gly Leu Gly Cys Asn Ser Ala
                100                 105                 110

Thr Lys His Leu Asn Ala Thr Ala Leu Gly Leu Arg Val Leu Arg Leu
                115                 120                 125

His Arg Tyr Asp Val Ser Pro Asp Thr Leu His Asn Phe Lys Asp Asn
                130                 135                 140

Thr Gly Lys Phe Val Leu Thr Gly Glu Asn Lys Asp Asn Asn Asp Glu
145                 150                 155                 160

Asp Thr Asn Lys Glu Glu Lys Val Met Arg Ser Ile Leu Asn Leu Phe
                165                 170                 175

Arg Leu Ser Ser Leu Ala Phe Pro Gly Glu Ile Ile Met Glu Glu Ala
                180                 185                 190

Lys Ala Phe Ser Thr Arg Tyr Leu Lys Glu Leu Leu Glu Ile Ser Arg
                195                 200                 205

Asp Thr Phe Asn Arg Ser Phe Ile Lys Glu Val Glu Tyr Ala Leu Thr
                210                 215                 220

Tyr Glu Trp Pro Arg Thr Phe Thr Arg Trp Glu Ala Arg Asn Phe Ile
225                 230                 235                 240

Glu Ile Cys Asp Leu Asp Asn Asp Arg Leu Lys Asp Lys Arg Ile Leu
                245                 250                 255

Glu Leu Ala Lys Leu Asp Phe Asn Ile Leu Gln Phe Gln Tyr Gln Leu
                260                 265                 270

Glu Met Lys Asn Leu Ser Arg Trp Trp Val Glu Ser Gly Ile Ser Asn
                275                 280                 285

Leu Val Ala Thr Arg Glu Arg Ser Ile Glu Tyr Leu Phe Trp Ala Val
                290                 295                 300

Thr Ser Thr Asp Glu Leu Glu Phe Ser Ser Arg Ile Ala His Ala
305                 310                 315                 320

Lys Cys Thr Thr Ile Ile Thr Ile Met Asp Asp Ile Phe Asp Tyr
                325                 330                 335

Ala Thr Leu Glu Gln Leu Lys Cys Ile Val Asp Ala Ile Ser Lys Asn
                340                 345                 350

```
Trp Asp Val Ser Ile Ile Glu Asn Ile Pro Asn Asn Leu Lys Thr Cys
            355                 360                 365

Phe Glu Phe Val Ser Lys Thr Val His Glu Leu Ala Ile Asp Ala Thr
        370                 375                 380

Glu Tyr Gln Gly Arg Asp Met Met Pro Phe Ile Thr Lys Ala Trp Thr
385                 390                 395                 400

Asp Tyr Gly Glu Ala Cys Phe Glu Gln Ala Cys Trp Lys Val Lys Gly
                405                 410                 415

Tyr Phe Pro Thr Tyr Asn Glu Tyr Ile Lys Cys Ala Glu Leu Ser Val
            420                 425                 430

Ala Phe Gly Pro Ile Leu Leu His Thr Ala Leu Leu Ala Ser Pro Asp
            435                 440                 445

Leu Cys Asp Asp Asp Ile Glu Lys Ile Tyr Leu Asp Lys Ser Arg Phe
        450                 455                 460

Phe Lys Leu Met Arg Val Cys Met Arg Leu Ile Asp Asp Ile Asn Asp
465                 470                 475                 480

Phe Glu Asp Glu Arg Leu His Gly Lys Ile Ala Ser Ala Ile Ala Cys
                485                 490                 495

Tyr Lys Gly Asp His Pro Asn Cys Ser Glu Ser Glu Ala Ile Asn Gln
            500                 505                 510

Ile Ile Thr Leu Asn Asn Lys Leu Leu Arg Glu Leu Thr Arg Glu Phe
        515                 520                 525

Phe Lys Ser Asn Met Asn Phe Leu Glu Trp Gln Lys Ile Cys Val Asn
530                 535                 540

Ser Thr Arg Gly Val Gln Phe Phe Tyr Ile Phe Arg Asp Gly Phe Thr
545                 550                 555                 560

Tyr Ser His Lys Glu Ile Lys Gln Gln Ile Phe Lys Ile Leu Val Asp
                565                 570                 575

Pro Ile Lys Met
            580

<210> SEQ ID NO 5
<211> LENGTH: 1743
<212> TYPE: DNA
<213> ORGANISM: Juniperus virginiana

<400> SEQUENCE: 5
atgtcgaatt tgaaaggaga ccacatttct tctgtttctt ccattccagc ccatgctttt     60
aatgagtggg gcgatgcttt tgttcaatct atggagatgc cgtacgggga acctgaatac    120
cgtgaacgtg ctgaaacact tgtgaaacaa gtcaaaatct tgttaaaaga aatgcaaact    180
ggagatggtg atctaatcga gcggcttgag atggttgatg cttttgcaatg ccttggcatt    240 gagcgatatt ttcaggctga gattaaagaa gctcttgatt acgtttaccg ctcttgggat    300
ggaactgtgg gaataggatt aggctgcaac agtgctacaa agcatttgaa tgccacagct    360
ttgggactca gagtacttcg actccatcgt tatgacgtct ctccagacac gttgtacaat    420
ttcaaggaca atactggcga gttcgtcctc tgtggagaaa ataaagtgag taacgatgag    480
gatactaata aggaagagaa agtgatgaga agtatgctca acctgttaag actatccagt    540
ttggcattcc ctggagaaat cattatggaa gaggctcaag catttagcac tagatatctt    600
aaagaattat tagaaatttc tggagataca tttaacagga gttttattaa agaggtggag    660
tatgctctta catatgaatg gcctcgaacc tttactagat gggaggcgtg gaatttcata    720
gagatctgtg atttagataa tgacaggttg gaagacaaaa ggattttaca gcttgcaaaa    780
```

```
ttggatttta atatactaca atttcaatat aagttggaga tgaaaaatct gtcaagttgg      840
tgggttgaat ctggcatctc caatctggtt gcaacaaggg cccgacatat tgaatatctt      900
ttttgggcag ttgcttctac agatgagatg gagttttcta gtagtagaat agctcttgca      960
aagaccaccg caattattac agtaatggat gacattttg atgactatgc aacacttgag     1020
tatctcaaat gtatttcaga tgccattct aaaaattggg atgtttctat tatagaaaat     1080
attcccaaca acttgaagac atgttttgaa tttatttcta aaacagttca tcaaatggca     1140
atagatgcta ctaaatatca aggacgtgac atgatgcctt ttattacaaa agcgtgggca     1200
gattatatag aagcctgctt tgaggaggca cgctggaaac tgacaggata ttttccaacc     1260
tacgatgagt acatgaaatc tgctgaacta tgtgttggat ttggacagat attttttatct    1320 agtgggctac tagcatctcc taatttatgt gatgatgata ttgagaagat ataccttgac     1380
aaatctagat tctttaaact catgcgagtg tgtatgcggt tgattgatga tataaatgat     1440
tttgaggatg agaggctcca tggaaagatt gcctcagcta ttgcttgtta caagggtgat     1500
catccaaatt gttcagaaag cgaggccatc aatcaaatca tcacgctcaa taataaatta     1560
ttgagagaat tgacaagaga attttttaaa tcaaatatga attttcttga atggcaaaag     1620
atatgtgtca atagtaccag aggagtacaa ttttctctata tatttagaga tgggtttaca    1680
tattctcaca aggagatcaa gcagcagata tttaaaatcc ttgttgatcc aataaaaatg     1740
tag                                                                   1743

<210> SEQ ID NO 6
<211> LENGTH: 1743
<212> TYPE: DNA
<213> ORGANISM: Juniperus virginiana

<400> SEQUENCE: 6
atgtcgaatt tgaaaggaga ccacatttct tctgtttctt ccattccagc ccatgctttt      60
aatgagtggg gcgatgcttt tgttcaatct atggagatgc cgtacgggga acctgaatac     120
cgtgaacgtg ctgaaacact tgtgaaacaa gtcaaaatct tgttaaaaga atgcaaact      180 ggagatggtg atctaatcga gcggcttgag atggttgatg ctttgcaatg ccttggcatt     240
gagcgatatt ttcaggctga gattaaagaa gctcttgatt acgtttaccg ctcttgggat     300
ggaactgtgg gaataggatt aggctgcaac agtgctacaa agcatttgaa tgccacagct     360
ttgggactca gagtacttcg actccatcgt tatgacgtct ctccagacac gttgcacaat     420 tcaaggaca atactgggaa gttcgtcctc actggagaaa ataaagacaa taacgatgaa     480
gatactaata aggaagagaa agtgatgaga agtattctca acctgttcag actatccagt     540
ttggcattcc ctggagaaat tattatgaa gaggctaaag catttagcac tagatatctt    600
aaagaattat tagaaattc tagagataca tttaacagga gttttattaa agaggtggag     660
tatgctctta catatgaatg gcctcgaacc tttactagat gggaggcgtg gaatttcata     720
gagatctgtg atttagataa tgacaggttg gaagacaaaa ggattttaca gcttgcaaaa     780
ttggatttta atatactaca atttcaatat aagttggaga tgaaaaatct gtcaagttgg     840
tgggttgaat ctggcatctc caatctggtt gcaacaaggg cccgacatat tgaatatctt      900
ttttgggcag ttgcttctac agatgagatg gagttttcta gtagtagaat agctcttgca      960
aagaccaccg caattattac agtaatggat gacattttg atgactatgc aacacttgag     1020
tatctcaaat gtatttcaga tgccattct aaaaattggg atgtttctat tatagaaaat     1080
```

```
attcccaaca acttgaagac atgttttgaa tttatttcta aaacagttca tcaaatggca    1140
atagatgcta ctaaatatca aggacgtgac atgatgcctt ttattacaaa agcgtgggca    1200
gattatatag aagcctgctt tgaggaggca cgctggaaac tgacaggata ttttccaacc    1260
tacgatgagt acatgaaatc tgctgaacta tgtgttggat ttggacagat attttttatct   1320 agtgggctac tagcatctcc taatttatgt gatgatgata ttgagaagat ataccttgac    1380
aaatctagat tctttaaact catgcgagtg tgtatgcggt tgattgatga tataaatgat    1440
tttgaggatg agaggctcca tggaaagatt gcctcagcta ttgcttgtta caagggtgat    1500
catccaaatt gttcagaaag tgaggccatc aatcaaatcg tcatgctcaa taataaatta    1560
ttgagagaat tgacaagaga attttttaaaa tcaaatatga attttcttga atgggaaaag   1620
atatgtgtca atagtacaag aggggtacaa ttttgctata tatttggaga tgggtttaca   1680
tattctcaca aggagatcaa gcaacagata tttaaaattc ttgtcaatcc aataaaagtg   1740
tag                                                                 1743

<210> SEQ ID NO 7
<211> LENGTH: 1743
<212> TYPE: DNA
<213> ORGANISM: Juniperus virginiana

<400> SEQUENCE: 7
atgtcgaatt tgaaaggaga ccacatttct tctgtttctt ccattccagc ccatgctttt     60
aatgagtggg gcgatgcttt tgttcaatct atggagatgc cgtacgggga acctgaatac    120
cgtgaacgtg ctgaaacact tgtgaaacaa gtcaaaatct tgttaaaaga aatgcaaact    180
ggagatggtg atctaatcga gcggcttgag atggttgatg ctttgcaatg ccttggcatt    240
gagcgatatt tcaggctgac gattaaagaa gctcttgatt acgtttaccg ctcttgggat    300
ggaactgtgg gaataggatt aggctgcaac agtgctacaa agcatttgaa tgccacagct    360
ttgggactca gagtacttcg actccatcgt tatgacgtct ctccagacac gttgcacaat    420
ttcaaggaca atactgggaa gttcgtcctc actggagaaa ataaagacaa taacgatgaa    480
gatactaata aggaagagaa agtgatgaga agtattctca acctgttcag actatccagt    540
ttggcattcc ctggagaaat tattatggaa gaggctaaag catttagcac tagatatctt    600
aaagaattat tagaaatttc tagagataca tttaacagga gttttattaa agaggtggag    660
tatgctctta catatgaatg gcctcgaacc tttactagat gggaggcgtg gaatttcata    720
gagatctgtg atttagataa tgacaggttg gaagacaaaa ggattttaca gcttgcaaaa    780
ttggatttta atatactaca atttcaatat aagttggaga tgaaaaatct gtcaagttgg    840
tgggttgaat ctggcatctc caatctggtt gcaacaaggg cccgacatat tgaatatctt    900
ttttgggcag ttgcttctac agatgagatg gagttttcta gtagtagaat agctcttgca    960
aagaccaccg caattattac agtaatggat gacatttttg atgactatgc aacacttgag   1020
tatctcaaat gtatttcaga tgccattcct aaaaattggg atgtttctat tatagaaaat   1080
attcccaaca acttgaagac atgttttgaa tttatttcta aaacagttca tcaaatggca   1140
atagatgcta ctaaatatca aggacgtgac atgatgcctt ttattacaaa agcgtgggca   1200
gattatatag aagcctgctt tgaggaggca cgctggaaac tgacaggata ttttccaacc   1260
tacgatgagt acatgaaatc tgctgaacta tgtgttggat ttggacagat attttttatct  1320 agtgggctac tagcatctcc taatttatgt gatgatgata ttgagaagat ataccttgac   1380
aaatctagat tctttaaact catgcgagtg tgtatgcggt tgattgatga tataaatgat   1440
```

```
tttgaggatg agaggctcca tggaaagatt gcctcagcta ttgcttgtta caagggtgat    1500
catccaaatt gttcagaaag cgaggccatc aatcaaatca tcacgctcaa taataaatta    1560
ttgagagaat tgacaagaga atttttaaa tcaaatatga attttcttga atggcaaaag     1620
atatgtgtca atagtaccag aggagtacaa ttttctata tatttagaga tgggtttaca     1680
tattctcaca aggagatcaa gcagcagata tttaaaatcc ttgttgatcc aataaaaatg    1740
tag                                                                  1743

<210> SEQ ID NO 8
<211> LENGTH: 1743
<212> TYPE: DNA
<213> ORGANISM: Juniperus virginiana

<400> SEQUENCE: 8
atgtcgaatt tgaaggaga ccacatttct tctgtttctt ccattccagc ccatgctttt     60
aatgagtggg gcgatgcttt tgttcaatct atggagatgc cgtacgggga acctgaatac    120
cgtgaacgtg ctgaaacact tgtgaaacaa gtcaaaatct tgttaaaaga aatgcaaact    180
ggagatggtg atctaatcga gcggcttgag atggttgatg ctttgcaatg ccttggcatt    240
gagcgatatt ttcaggctga gattaaagaa gctcttgatt acgtttaccg ctcttgggat    300
ggaactgtgg gaataggatt aggctgcaac agtgctacaa agcatttgaa tgccacagct    360
ttgggactca gagtacttcg actccatcgt tatgacgtct ctccagacac gttgcacaat    420
ttcaaggaca atactgggaa gttcgtcctc actggagaaa ataaagacaa taacgatgaa    480
gatactaata aggaagagaa agtgatgaga agtattctca acctgttcag actatccagt    540
ttggcattcc ctggagaaat tattatgaa gaggctaaag catttagcac tagatatctt     600
aaagaattat tagaaatttc tagagataca tttaacagga gttttattaa agaggtggag    660
tatgctctta catatgaatg gcctcgaacc tttactagat ggagggcccg gaatttcata    720
gaaatctgtg atttagataa tgacaggttg aaagataaaa ggattttaga gcttgcaaaa    780 ttggattta atatactaca atttcaatat cagctggaga tgaaaaatct ctcaaggtgg    840
tgggttgaat ctggcatctc caatctagtt gcaacaaggg agcgatctat tgaatatctt    900
ttttgggcag ttacttctac agatgagttg gaattttcta gtagtagaat agctcatgca    960
aagtgcacca caataattac aataatggat gatattttg atgactatgc aacacttgag    1020
caactcaaat gtattgtaga tgccatttca aaaaattggg atgtttctat tatagagaat    1080 atcccaata acttgaagac atgctttgaa tttgtttcta aaacagttca tgaattggca    1140
atagatgcta ctgaatatca aggacgtgac atgatgcctt ttattacaaa agcgtggaca    1200
gattatggag aagcttgctt tgagcaggca tgctggaaag tgaaaggata ttttccaacc    1260
tacaatgagt acataaagtg tgctgaatta agtgttgcat ttggaccgat attgttacat    1320
actgcactac tagcatctcc cgatttatgc gatgatgata ttgagaagat ataccttgac    1380
aaatctagat tctttaaact catgcgagtg tgtatgcggt tgattgatga tataaatgat    1440
tttgaggatg agaggctcca tggaaagatt gcctcagcta ttgcttgtta caagggtgat    1500
catccaaatt gttcagaaag cgaggccatc aatcaaatca tcacgctcaa taataaatta    1560
ttgagagaat tgacaagaga atttttaaa tcaaatatga attttcttga atggcaaaag     1620
atatgtgtca atagtaccag aggagtacaa ttttctata tatttagaga tgggtttaca     1680
tattctcaca aggagatcaa gcagcagata tttaaaatcc ttgttgatcc aataaaaatg    1740
``` tag                                                                    1743

<210> SEQ ID NO 9
<211> LENGTH: 1743
<212> TYPE: DNA
<213> ORGANISM: artificial sequence
<220> FEATURE:
<223> OTHER INFORMATION: codon optimised cDNA sequence

<400> SEQUENCE: 9
atgagcaatt tgaaaggcga tcacatcagc agcgtatcta gcattccggc acatgcattc      60
aatgaatggg gcgacgcctt tgttcagagc atggaaatgc cgtacggtga gccggaatat     120
cgcgagcgtg cggagactct ggtcaaacaa gtgaagattc tgctgaaaga gatgcaaacc     180
ggtgacggcg acttgattga acgtctggag atggtggatg cgctgcaatg cctgggtatt     240
gagcgttatt ccaagcgga gattaaagag gcgctggatt acgtgtaccg tagctgggac     300
ggcacggtgg gcatcggtct gggttgcaac tcggccacca gcatctgaa cgctaccgct     360
ctgggcctgc gtgttctgcg cctgcatcgt tatgatgtga gccctgacac cttgtataac     420
tttaaggaca taccggcga atttgtcctg tgtggtgaga caaagttag caatgatgaa     480
gatactaaca agaagagaa ggttatgcgc agcatgttga atttgctgcg cctgagctct     540
ttggctttc cgggtgagat catcatggaa gaagcgcagg cgtttagcac ccgttatctg     600
aaagaactgc tggagatctc tggcgacacc tttaatcgta gcttcatcaa agaggtcgag     660
tacgcgctga cctatgaatg gccacgtacc ttcacccgct gggaagcatg gaatttcatt     720
gaaatttgtg acctggacaa cgaccgtctg gaagataagc gtatcctgca gctggcgaag     780
ctggacttca acatcctgca gtttcagtac aagctggaga tgaagaatct gagcagctgg     840
tgggttgaga gcgtatttc caacttggtc gcgacgcgtg cgcgccacat cgagtacttg     900
tttttgggcgg tcgcgtctac ggacgagatg gagttttcca gctcccgtat cgccctggcg     960
aaaaccacgg ctattatcac cgttatggat gacatttcg atgattacgc gacgctggag    1020
tacctgaaat gtatttccga cgccattagc aagaattggg atgtcagcat tattgaaaac    1080
atcccgaaca atctgaaaac gtgcttcgag ttcattagca aaacggtgca ccagatggcc    1140
attgatgcga cgaagtatca gggccgtgac atgatgccgt ttatcactaa ggcctgggct    1200
gattacattg aagcctgttt cgaagaagca cgctggaagc tgacgggtta cttcccgacc    1260
tatgatgagt acatgaaaag cgcggaactg tgcgtgggtt tcggtcagat ttttctgagc    1320
tcgggcctgt tggcaagccc gaatttgtgt gatgacgata ttgagaagat ttacctggat    1380
aaaagccgtt tcttcaagct gatgcgcgtt tgcatgcgtc tgatcgatga catcaacgac    1440
ttcgaggacg aacgtctgca cggtaagatc gcaagcgcaa tcgcatgcta agggtgac    1500
cacccgaatt gcagcgaaag cgaggcaatt aaccaaatca tcaccttgaa caataaactg    1560
ctgcgcgaac tgacccgcga gttttttcaag agcaatatga ctttctgga gtggcagaaa    1620
atctgtgtga actccacccg tggtgtccaa ttcttctata tctttcgtga tggttttacc    1680
tactctcaca aagagattaa acaacaaatc ttcaaaattc tggttgaccc gatcaagatg    1740
taa                                                                  1743

<210> SEQ ID NO 10
<211> LENGTH: 1743
<212> TYPE: DNA
<213> ORGANISM: artificial sequence
<220> FEATURE:
<223> OTHER INFORMATION: codon optimised cDNA sequence

<400> SEQUENCE: 10

```
atgagcaatt tgaaaggcga tcacatcagc agcgtatcta gcattccggc acatgcattc      60
aatgagtggg gtgatgcgtt cgtccaaagc atggaaatgc cgtatggtga gccggagtac     120
cgtgaacgtg ctgaaacgct ggttaaacaa gtgaagattt gctgaaaga aatgcagacc      180
ggcgatggtg acctgatcga acgcctggag atggtggacg cactgcaatg tctgggtatt    240
gagcgttact tcaagccga gatcaaagaa gcgctggact acgtgtaccg cagctgggat    300
ggcaccgtcg gtattggtct gggttgcaat agcgcgacca agcacctgaa tgcaacggcg    360
ctgggtctgc gcgttctgcg cctgcaccgc tatgatgtta gcccggatac tctgcataac    420
ttcaaggata cacgggtaa gtttgtcctg acgggcgaga caaagacaa taacgacgaa      480
gatactaaca agaagagaa ggttatgcgt tccattctga atctgtttcg tttgagctcc     540
ctggcatttc cgggcgagat cattatggaa gaggctaaag cgttctctac tcgttacctg    600
aaagaactgc tggaaatcag ccgcgacacc ttcaatcgta gcttcatcaa agaggttgag    660
tatgctttga cctacgagtg gcctcgcacc tttacgcgtt gggaagcgtg gaatttcatc    720
gaaatttgcg acctggacaa cgaccgtctg gaagataagc gtatcttgca gctggcaaag    780
ctggacttca atatcctgca atttcagtac aaactggaaa tgaagaatct gtccagctgg    840
tgggtcgaga gcggtattag caacctggtg gcgacgcgtg cgcgtcatat cgaatacttg    900
ttctgggcgg tcgccagcac ggacgagatg gagttcagca gctctcgtat tgccctggca    960
aagaccaccg caattatcac cgtgatggat gacatttttcg atgactacgc gaccctggag   1020
tacctgaaat gtatttcgga tgcgatcagc aagaactggg atgtttccat tattgaaaac   1080
attccgaaca acctgaaaac ctgttttgag tttatcagca aaaccgttca ccagatggcg   1140
atcgatgcta cgaaatatca gggtcgtgac atgatgccat tcattacgaa ggcgtgggcc   1200
gactatattg aggcatgttt cgaagaagcg cgttggaagc tgacgggcta ctttccgacc   1260
tacgacgagt atatgaagag cgcggaattg tgcgttggtt ttggtcagat ctttctgagc   1320
tctggcctgt tggcttcccc gaatctgtgc gacgacgaca ttgagaaaat ctatttggac   1380
aagtcccgct tcttcaagct gatgcgtgtt tgtatgcgct tgatcgatga cattaacgat   1440
ttcgaggatg agcgtctgca cggcaaaatc gccagcgcca tcgcctgcta taaaggcgac   1500
catccgaatt gtagcgagtc tgaggcgatc aaccagatcg tgatgctgaa taacaaattg   1560
ctgcgcgaac tgacccgcga gttcctgaag agcaatatga actttctgga gtgggagaag   1620
atttgcgtga acagcacccg tggtgtgcaa ttctgctaca ttttttggcga tggttttacc   1680
tatagccaca agaaatcaa acaacagatc tttaagattc tggtcaatcc gatcaaggtc   1740
taa                                                                 1743
```

<210> SEQ ID NO 11
<211> LENGTH: 1743
<212> TYPE: DNA
<213> ORGANISM: artificial sequence
<220> FEATURE:
<223> OTHER INFORMATION: codon optimised cDNA sequence

<400> SEQUENCE: 11

```
atgagcaatt tgaaaggcga tcacatcagc agcgtatcta gcattccggc acatgcattc      60
aatgagtggg gtgacgcgtt tgtgcagagc atggaaatgc cgtatggtga accggaatat    120
cgtgagcgtg ctgaaacccct ggtgaagcaa gtcaagattt gttgaaaga aatgcaaacc     180
```

| | |
|---|---:|
| ggcgacggtg atctgatcga gcgcctggag atggttgatg cgctgcagtg tctgggtatt | 240 |
| gagcgctatt ttcaagccga gatcaaagaa gcgctggatt acgtttatcg tagctgggat | 300 |
| ggcacggttg gtattggcct gggctgcaat agcgcgacca agcacctgaa cgctaccgcg | 360 |
| ctgggtctgc gcgtgttgcg tttgcaccgc tacgacgttt cgccggatac tctgcataac | 420 |
| tttaaagata tacgggcaa attcgtcctg acgggtgaga acaaagataa caacgatgag | 480 |
| gacacgaaca agaagaaaa agtcatgcgc tccatcctga atctgtttcg tctgagcagc | 540 |
| ctggctttc ctggcgagat cattatggaa gaagcgaagg cgtttagcac ccgttacctg | 600 |
| aaagaactgt tggagatcag ccgtgatacc ttcaaccgta gctttatcaa agaggtggag | 660 |
| tacgcgctga cctacgagtg gccgcgtacc tttacccgtt gggaagcctg gaatttcatt | 720 |
| gagatctgcg acctggataa cgaccgtctg gaagataagc gtattctgca attggcgaaa | 780 |
| ctggacttca atattctgca gttccagtac aagctggaga tgaagaatct gtccagctgg | 840 |
| tgggttgaga gcggtatcag caacctggtc gcgacgcgtg cacgtcatat cgagtacctg | 900 |
| ttttgggcgg tcgctagcac ggacgaaatg gagtttagct ccagccgcat tgcactggcc | 960 |
| aagaccactg caatcattac cgtgatggat gatatctttg acgattacgc gaccttggag | 1020 |
| tatctgaaat gcatctctga cgcgatcagc aagaactggg acgttagcat tattgaaaac | 1080 |
| attccgaata acttgaaaac gtgttttgag ttcattagca aaactgttca ccaaatggca | 1140 |
| atcgacgcca ccaaatatca gggccgtgac atgatgccgt tatcaccaa ggcctgggca | 1200 |
| gactacatcg aggcatgctt tgaagaagct cgctggaaac tgacgggtta ttttcccgacc | 1260 |
| tacgatgagt acatgaagtc cgccgagctg tgcgtcggct tcggtcagat tttcctgtcg | 1320 |
| agcggtctgc tggcaagccc aaatctgtgt gacgacgaca ttgaaaagat ttacttggac | 1380 |
| aagagccgct ttttcaagct gatgcgtgtg tgtatgcgtc tgattgatga cattaacgat | 1440 |
| ttcgaggacg aacgcctgca cggtaagatc gcgtccgcca ttgcgtgcta caagggcgac | 1500 |
| catccgaatt gctctgaatc tgaagcgatt aaccaaatca tcaccctgaa caataaactg | 1560 |
| ctgcgtgagt tgacccgtga gttcttcaag tctaacatga ttttctgga gtggcagaag | 1620 |
| atttgtgtta atagcacgcg cggtgtgcaa ttcttctata tcttccgcga tggtttcacg | 1680 |
| tatagccaca aagagatcaa gcagcagatt ttcaaaatcc tggtggaccc gatcaaaatg | 1740 |
| taa | 1743 |

<210> SEQ ID NO 12
<211> LENGTH: 1743
<212> TYPE: DNA
<213> ORGANISM: artificial sequence
<220> FEATURE:
<223> OTHER INFORMATION: codon optimised cDNA sequence

<400> SEQUENCE: 12

| | |
|---|---:|
| atgagcaatt tgaaaggcga tcacatcagc agcgtatcta gcattccggc acatgcattc | 60 |
| aacgagtggg gcgacgcttt cgtgcaatct atggagatgc cgtatggtga gccggagtac | 120 |
| cgtgagcgtg cggaaacgct ggtgaaacaa gttaagatcc tgctgaaaga gatgcagacc | 180 |
| ggtgatggcg atctgattga acgtctggag atgtcgatg cgctgcaatg cctgggtatc | 240 |
| gaacgttact tccaggcgga gatcaaagag gccctggact atgtttaccg tagctgggat | 300 |
| ggcacggtcg gtattggtct gggttgcaac agcgcgacga acacctgaa cgcgacggct | 360 |
| ctgggtctgc gcgttctgcg cctgcaccgt tacgatgtca gcccggacac gctgcataac | 420 |
| tttaaggaca atacgggcaa atttgtgctg actggtgaaa acaaagataa caacgacgag | 480 |

```
gataccaata agaagaaaaa ggtcatgcgt tccatcctga atttgttccg cctgagcagc        540 ttggccttc  cgggcgagat cattatggaa gaagcgaagg cgtttagcac ccgttatctg        600
aaagaactgc tggaaattag ccgcgacacc tttaaccgca gctttatcaa agaagtcgaa        660
tacgccctga cctacgagtg gccgcgtacc tttacccgtt gggaagcgcg taatttcatt        720
gaaatctgtg atttggataa tgaccgtctg aaggataagc gtatcctgga gctggcgaag        780
ctggacttta acattttgca gttccaatat cagttggaga tgaaaaatct gagccgctgg        840
tgggtggaga gcggtattag caacttggtt gccactcgtg agcgttccat tgaatacctg        900
ttctgggcgg tcacgtctac cgacgaactg gagtttagct ctagccgcat cgcgcacgcg        960
aaatgcacca cgatcatcac catcatggat gatatctttg acgattatgc aaccctggag       1020
caactgaagt gtattgtgga cgctatttcg aagaactggg acgtttccat cattgagaac       1080
attccgaata atctgaaaac ctgtttcgag ttcgtgagca aaaccgttca cgagctggca       1140
attgatgcca ccgagtatca aggtcgtgac atgatgccgt tcatcaccaa ggcctggacc       1200
gattatggtg aagcatgttt cgagcaggct tgctggaagg tgaagggtta ctttcctacc       1260
tacaacgagt atatcaagtg cgcagaactg agcgtcgcct ttggcccgat tctgctgcat       1320
acggcgctgt ggcgagcccc agacctgtgc gacgatgaca ttgagaaaat ctatttggac       1380
aagtcgcgct tctttaaact gatgcgcgtt tgtatgcgcc tgattgacga cattaatgac       1440
ttcgaggatg agcgcttgca cggcaagatt gcaagcgcga ttgcatgcta aagggtgat        1500 catccgaatt gcagcgaatc cgaggcaatc aaccagatca ttactctgaa caataaactg       1560
ctgcgtgaac tgacgcgtga gttctttaag agcaatatga attttctgga atggcagaag       1620
atttgtgtta actccacccg tggcgttcag ttcttctaca tcttccgtga cggtttcacc       1680
tacagccaca agaaatcaa  acagcaaatc ttcaaaatcc tggtggaccc gatcaagatg       1740
taa                                                                    1743
```

<210> SEQ ID NO 13
<211> LENGTH: 582
<212> TYPE: PRT
<213> ORGANISM: Platycladus orientalis "Beverleyensis"

<400> SEQUENCE: 13

```
Met Ser Asn Leu Met Gly Asp His Ile Ser Ser Leu Ser Ser Ile Pro
1               5                   10                  15

Ser Asn Ala Phe Asn Gln Trp Asp Asp Ala Phe Ile Gln Ser Met Glu
            20                  25                  30

Thr Pro Tyr Gly Glu Pro Glu Tyr Arg Glu Arg Ala Glu Thr Leu Ala
        35                  40                  45

Lys Glu Ile Lys Ile Phe Leu Lys Asp Met Gln Ser Gly Gly Gly Asp
    50                  55                  60

Gly Asp Leu Ile Glu Arg Leu Glu Ile Val Asp Ala Leu Gln Cys Leu
65                  70                  75                  80

Gly Ile Asp Arg Tyr Phe Gln Ala Glu Ile Lys Ala Ala Leu Asp Tyr
                85                  90                  95

Val Tyr Asn Cys Trp Asp Glu Val Gly Ile Gly Leu Gly Ser Gln
            100                 105                 110

Ser Ala Thr Lys Asp Leu Asn Ala Thr Ala Leu Ala Leu Arg Val Phe
        115                 120                 125

Arg Leu Asn Arg Tyr Asp Val Ser Ala Asp Thr Leu Lys Tyr Phe Lys
    130                 135                 140
```

```
Asp Asn Asn Gly Arg Phe Val Leu Cys Gly Asp Asn Lys Asp Asn
145                 150                 155                 160

Asp Glu Asp Asn Ser Lys Glu Lys Val Met Arg Ser Met Leu Asn
            165                 170                 175

Leu Leu Arg Leu Ser Ser Leu Ala Phe Pro Ala Glu Ile Val Met Glu
        180                 185                 190

Glu Ala Lys Ala Phe Ser Ser Arg Tyr Leu Lys Glu Leu Leu Gly Lys
        195                 200                 205

Ser Gly Asp Thr Ser Lys Lys Ser Phe Leu Lys Glu Val Glu Tyr Ala
    210                 215                 220

Leu Ile Tyr Glu Trp Pro Arg Thr Phe Ile Arg Trp Glu Ala Arg Asn
225                 230                 235                 240

Phe Ile Glu Ile Tyr Glu Leu Asp Asn Glu Arg Leu Lys Glu Lys Arg
                245                 250                 255

Ile Leu Glu Leu Ala Lys Leu Asp Phe Asn Ile Leu Gln Phe His Tyr
            260                 265                 270

Lys Leu Glu Met Lys Asn Leu Ser Ser Trp Val Glu Ser Glu Ile
        275                 280                 285

Ser Lys Leu Ile Ala Thr Arg Glu Arg Ser Ile Glu Tyr Leu Leu Trp
    290                 295                 300

Ala Ile Ser Ser Met Asp Glu Leu Glu His Ser Ser Ser Arg Ile Ala
305                 310                 315                 320

Leu Ala Lys Ile Thr Ser Leu Ile Thr Ile Leu Asp Asp Ile Phe Asp
                325                 330                 335

Asp Tyr Ala Thr Phe Glu Gln Leu Lys Cys Ile Arg Asp Ala Ile Phe
            340                 345                 350

Lys Gly Trp Asp Val Ser Ile Ile Glu Asn Ile Pro Asn Asn Trp Lys
        355                 360                 365

Arg Cys Val Glu Phe Val Phe Lys Thr Ile His Gln Leu Thr Ile Asp
    370                 375                 380

Ala Thr Asp Tyr Gln Gly Arg Asp Met Met Pro Phe Val Ser Lys Ala
385                 390                 395                 400

Trp Glu Asp Tyr Val Glu Ala Cys Phe Glu Gln Ala Arg Trp Lys Leu
                405                 410                 415

Lys Gly Tyr Phe Pro Thr Tyr Asn Glu Tyr Ile Lys Ile Ala Gly Lys
            420                 425                 430

Cys Val Gly Phe Gly Pro Phe Ser Leu His Ser Ala Ile Leu Ala Ser
        435                 440                 445

Pro Asn Leu Cys Asp Asp Ile Gln Lys Ile Tyr Leu Asp Lys Ser
    450                 455                 460

Arg Phe Tyr Gln Leu Met Arg Val Ala Met Arg Leu Ile Asp Asp Ile
465                 470                 475                 480

His Asp Phe Glu Glu Glu Arg Leu His Gly Lys Met Ala Ser Ala Ile
                485                 490                 495

Ser Cys Tyr Met Ala Asp His Pro Asn Cys Ser Glu Lys Glu Ala Met
            500                 505                 510

Asn His Ile Ile Glu Leu Asn Asn Glu Val Leu Lys Glu Leu Thr Arg
        515                 520                 525

Glu Phe Leu Lys Pro Ser Met Ile Phe His Glu Trp Glu Lys Ile Phe
    530                 535                 540

Val Asn Ser Thr Arg Gly Val Gln Phe Phe Tyr Val His Gly Asp Gly
545                 550                 555                 560
```

```
Phe Thr Tyr Thr His Lys Glu Ile Lys His Gln Ile Leu Lys Ile Ile
                565                 570                 575

Val Asp Pro Ile Lys Ile
            580
```

<210> SEQ ID NO 14
<211> LENGTH: 576
<212> TYPE: PRT
<213> ORGANISM: Platycladus orientalis

<400> SEQUENCE: 14

```
Met Ser Thr Leu Glu Gly Asp Asn Ile Tyr Ser Val Ser Ser Leu Pro
1               5                   10                  15

Ala His Ala Phe Asn Glu Trp Glu Asp Ala Ser Val Gln Ser Met Glu
                20                  25                  30

Met Ser Tyr Gly Glu Pro Glu Tyr Arg Glu Arg Ala Glu Thr Leu Val
                35                  40                  45

Lys Glu Val Lys Ile Leu Leu Lys Glu Met His Thr Gly Asp Gly Asp
    50                  55                  60

Leu Ile Glu Arg Leu Glu Met Val Asp Ala Leu Gln Cys Leu Gly Ile
65                  70                  75                  80

Tyr Arg Tyr Phe Gln Ala Glu Ile Lys Gln Ala Leu Asp Tyr Val Tyr
                85                  90                  95

Ser Cys Trp Asp Gly Asn Val Gly Ile Gly Leu Gly Ser Glu Ser Pro
                100                 105                 110

Thr Gln His Leu Asn Ala Thr Ala Leu Gly Ile Arg Val Leu Arg Leu
                115                 120                 125

His Arg Tyr Asp Val Ser Ala Asp Thr Leu Lys Asn Phe Lys Asp Lys
    130                 135                 140

Asn Gly Gln Phe Val Leu Cys Gly Gly Asn Asn Asp Asn Asn Asp Glu
145                 150                 155                 160

Glu Glu Lys Val Met Arg Ser Met Leu Asn Leu Phe Arg Leu Ser Ser
                165                 170                 175

Val Ala Ile Pro Gly Glu Met Val Leu Glu Glu Ala Lys Ala Phe Ser
                180                 185                 190

Ser Arg Tyr Leu Lys Glu Leu Leu Glu Asn Ser Gly Asp Thr Val Lys
                195                 200                 205

Arg Ser Phe Ile Lys Glu Val Glu Tyr Ala Leu Thr Tyr Glu Trp Pro
    210                 215                 220

Ile Thr Phe Asp Arg Trp Glu Ala Leu Asn Phe Ile Glu Ile Tyr Asp
225                 230                 235                 240

Leu Asn Asn Glu Arg Leu Met Asp Lys Arg Ile Leu Glu Leu Ala Lys
                245                 250                 255

Leu Asn Phe Asn Ile Leu Gln Phe Gln Tyr Lys Leu Glu Met Lys Asn
                260                 265                 270

Leu Ser Ser Trp Trp Ala Lys Ser Gly Ile Ser Lys Leu Leu Ala Val
                275                 280                 285

Arg Glu Arg Ser Ile Glu Tyr Leu Phe Trp Ala Ile Thr Ser Val Glu
    290                 295                 300

Glu Leu Glu Leu Ser Ser Arg Ile Ala Leu Val Lys Cys Thr Thr
305                 310                 315                 320

Val Ile Thr Ile Val Asp Asp Ile Phe Asp Asp Tyr Ala Thr Phe Glu
                325                 330                 335

Gln Leu Gln Cys Ile Thr Asp Ala Ile Ser Lys Asp Trp Asp Val Ser
                340                 345                 350
```

```
Leu Leu Glu Asn Ile Pro Ser Asn Leu Lys Thr Ser Leu Glu Phe Val
        355                 360                 365
Ser Lys Thr Ile His Glu Leu Ala Met Asp Ala Thr Lys Tyr Gln Gly
        370                 375                 380
Arg Asp Met Met Pro Phe Val Thr Lys Ala Trp Leu Asp Tyr Thr Asn
385                 390                 395                 400
Ala Cys Phe Glu Gln Ala Arg Trp Lys Val Thr Gly Tyr Phe Pro Ser
                405                 410                 415
Tyr Asn Glu Tyr Ile Lys Ala Ala Glu Leu Ser Val Ala Phe Gly Pro
            420                 425                 430
Ile Leu Leu His Thr Ala Leu Ala Ala Ser Pro Ile Leu Cys Asp Glu
        435                 440                 445
Asp Ile Glu Lys Ile Tyr Leu Asp Lys Ser Arg Phe Tyr His Ile Met
        450                 455                 460
Arg Val Ser Met Arg Leu Thr Asp Asp Ile His Asp Phe Glu Asp Glu
465                 470                 475                 480
Arg Leu His Gly Lys Met Ala Ser Ala Ile Ser Cys Tyr Lys Gly Asp
                485                 490                 495
His Pro Asn Cys Ser Glu Glu Ala Ile Asn Asn Ile Val Thr Leu
            500                 505                 510
Asn Asn Glu Leu Leu Lys Glu Met Ile Arg Glu Phe Phe Lys Pro Asn
        515                 520                 525
Ser His Tyr Leu Glu Trp Glu Lys Ile Cys Val Asn Ser Thr Arg Gly
        530                 535                 540
Ile Gly Phe Phe Tyr Ile Phe Gly Asp Gly Phe Thr Tyr Ser His Lys
545                 550                 555                 560
Glu Ile Lys Glu Gln Ile Phe Lys Ile Ile Val Asn Pro Ile Lys Val
                565                 570                 575

<210> SEQ ID NO 15
<211> LENGTH: 1749
<212> TYPE: DNA
<213> ORGANISM: Platycladus orientalis "Beverleyensis"

<400> SEQUENCE: 15
atgtctaatt tgatgggaga tcacatttct tctctttctt ccattccatc caatgctttc      60
aatcagtggg acgatgcgtt tattcaatct atggagacgc catacgggga acctgaatac     120
cgtgaacgtg ctgaaacact tgctaaggaa ataaaaatct ttttaaaaga catgcaatct     180
ggaggtggag atggcgatct aatcgagcgg cttgagattt tgacgccttt gcaatgcctc     240
ggaatagatc gttatttttca ggctgaaata aaagcggctc ttgattacgt ttataactgt     300
tgggatgaaa gtgtggggat aggattaggg agccaaagtg ctacaaagga tttgaatgct     360
acagctttag cacttcgagt gtttcgactt aatcgttatg atgtgtctgc agacacgttg     420
aagtatttca aggataataa tgggcggttc gtactctgtg agacaataa agacaacaac     480
gacgaggata atagcaaaga agaaaaagtg atgagaagta tgctcaacct gttaagactt     540
tccagtttgg catttcctgc agaaatcgtt atggaagagg ctaaagcatt cagttctaga     600
tatcttaaag aactattagg aaaatctgga gatacatcta gaaaagtttt tcttaaagag     660
gtggagtatg cccttatata tgaatggcct cgaacattta ttagatggga ggcacgaaat     720
ttcatagaaa tctatgaact agataatgag aggttaaaag agaaaggat tttagaactt     780
gcgaaattgg attttaacat actacaattt cactacaagc tagagatgaa aaatctctca     840
```

| | |
|---|---|
| agttggtggg ttgaatctga atctccaag ctaattgcaa caagagaacg atccattgaa | 900 |
| tatcttttgt gggcaattag ttctatggat gaattggagc attctagtag tagaatagct | 960 |
| cttgcaaaaa tcacatcact tatcacaata ttggatgata tttttgatga ctatgcaaca | 1020 |
| tttgagcaac tcaaatgcat tagggatgcc attttaaag gttgggatgt ttctatcata | 1080 |
| gaaaacattc ccaacaactg aaaagatgc gtggaatttg ttttaaaac aattcatcaa | 1140 |
| ttgacaatag atgctactga ttatcaaggg cgtgacatga tgccttttgt ttcaaaagcg | 1200 |
| tgggaagatt atgtggaagc ctgctttgag caggcacgat ggaaattgaa aggatatttt | 1260 |
| ccaacctaca atgagtacat aaagatagct ggaaaatgtg tagggtttgg acccttttct | 1320 |
| ttacattctg ccatactagc atctccaaat ttatgtgatg atgatattca gaagatatac | 1380 |
| cttgataaat ctagatttta tcaactcatg cgagtggcta tgaggttaat tgatgatata | 1440 |
| cacgactttg aggaagagag actccatgga aagatggcct cagctatttc ttgttatatg | 1500 |
| gctgatcatc caaattgttc agagaaagag gcaatgaatc atatcatcga actaaataat | 1560 |
| gaagtattga aggaattgac aagagaattt ttaaaaccaa gtatgatatt tcatgagtgg | 1620 |
| gagaagatat ttgtcaattc tactcgagga gtacaatttt tctatgtaca tggtgatgga | 1680 |
| tttacatata cgcataagga gatcaagcat cagatactaa aaattattgt cgatccaata | 1740 |
| aaaatctag | 1749 |

<210> SEQ ID NO 16
<211> LENGTH: 1731
<212> TYPE: DNA
<213> ORGANISM: Platycladus orientalis

<400> SEQUENCE: 16

| | |
|---|---|
| atgtcgactt tggaaggaga caacatttat tctgtttctt ccttaccagc ccatgctttt | 60 |
| aatgagtggg aagatgcttc tgttcaatct atggagatgt catacgggga acctgaatac | 120 |
| cgtgaacgtg ctgaaacact tgtgaaagaa gtaaaaatct tgttgaaaga atgcacact | 180 |
| ggagatggcg atctaatcga gcggcttgag atggttgatg cattgcaatg ccttggaatt | 240 |
| tatcgatact tcaggctga gattaaacaa gctcttgatt acgtttacag ctgctgggat | 300 |
| ggaaatgtgg ggataggatt aggctccgag agtcctacac agcatttgaa tgccacagct | 360 |
| ttgggaatca gagtactgcg actccatcgt tatgatgtgt ctgcagacac gttgaagaat | 420 |
| ttcaaggaca aaaatgggca gttcgtactc tgtggaggaa ataatgacaa taacgatgag | 480 |
| gaagagaaag tgatgagaag tatgctcaac ctgttcagac tttccagtgt ggcaattcct | 540 |
| ggagaaatgg ttctggaaga ggctaaagca tttagcagta gatatcttaa agaattatta | 600 |
| gaaaattctg gagatacagt taagagaagt tttattaaag aggtggagta tgctcttacc | 660 |
| tatgaatggc ctataacttt tgatagatgg gaggcactga atttcataga aatctatgat | 720 |
| ttaaataatg agaggttgat ggacaaaagg atattagagc ttgcaaaatt gaatttaat | 780 |
| atactacaat ttcaatacaa gttggagatg aaaaatctct caagttggtg ggctaaatct | 840 |
| ggcatctcga aactacttgc agtaagggag cgatccattg aatatctttt tgggcaatt | 900 |
| acttctgtag aagaattgga gctttctagt agtagaatag ctcttgtaaa gtgcacaaca | 960 |
| gttattacaa tagtggatga tattttgat gactatgcaa catttgagca actccaatgt | 1020 |
| attacagatg ctatctctaa agattgggat gtttctcttt tagaaaacat tcccagcaac | 1080 |
| ttgaagacaa gcttggaatt tgtttcaaaa acaattcatg agttggcaat ggatgctact | 1140 |
| aaatatcaag ggcgtgacat gatgcctttt gttacaaaag cgtggttaga ttacacgaac | 1200 |

```
gcctgctttg agcaagcacg atggaaagtg actggttatt ttccaagcta caatgagtac    1260
ataaaggctg ctgaattaag tgtagcattt ggaccgatat tgttacatac tgccctagca    1320
gcatctccta ttttatgcga tgaagatatt gagaagatat accttgataa atctagattc    1380
tatcatatca tgcgagtgtc tatgcggttg actgatgata tacatgattt tgaggatgag    1440
aggctgcatg gaaagatggc ttcagctatt tcttgttata agggtgatca tccaaattgt    1500
tcagaagaag aggcaataaa taatattgtc accctcaata tgaattatt gaaggaaatg    1560 ataagggaat ttttaaacc aaatagtcat tatcttgaat gggaaaagat atgtgtcaat    1620
agtactagag aataggatt tttctatata tttggagatg ggtttacata ttctcacaag    1680
gaaatcaagg agcagatatt taaaattatt gttaatccaa taaaagtgta g            1731
```

<210> SEQ ID NO 17
<211> LENGTH: 1749
<212> TYPE: DNA
<213> ORGANISM: artificial sequence
<220> FEATURE:
<223> OTHER INFORMATION: codon optimised cDNA sequence

<400> SEQUENCE: 17

```
atgtccaacc tgatgggcga tcatattagc tctctgagtt ccatcccgtc caacgctttt      60
aatcagtggg atgacgcgtt cattcaatca atggaaaccc gtatggtga accggaatac     120 cgtgaacgcg ctgaaacgct ggcgaaagaa atcaaaatct tcctgaaaga tatgcagtct    180
ggcggtggcg acggcgatct gattgaacgt ctggaaatcg tggacgccct gcagtgcctg    240
ggtattgatc gctattttca gcagaaatc aaagcggccc tggactatgt ttacaactgt    300
tgggatgaat cggtcggtat tggcctgggt tcccaatcag ccaccaaaga tctgaacgca    360
acggctctgg cgctgcgtgt gtttcgcctg aatcgttatg acgtttctgc ggataccctg    420
aaatacttca agataacaa cggccgtttc gttctgtgcg gtgacaacaa agataacaac    480
gacgaagata actctaaaga agaaaaagtc atgcgtagta tgctgaatct gctgcgcctg    540
tcatcgctgg cttttccggc ggaaattgtc atggaagaag ccaaagcatt tagctctcgc    600
tatctgaaag aactgctggg caaaagcggt gataccagca aaaaatcttt tctgaaagaa    660
gtggaatacg ccctgattta cgaatggccg cgcacgttca tccgttggga agcacgcaac    720
ttcatcgaaa tctacgaact ggacaacgaa cgtctgaaag aaaaacgcat tctggaactg    780
gcgaaactgg attttaacat cctgcagttc cattacaaac tggaaatgaa aaacctgagt    840
tcctggtggg tggaatctga aattagtaaa ctgatcgcta cccgtgaacg ctccattgaa    900
tatctgctgt gggcgatctc atcgatggat gaactggaac acagctctag tcgtattgct    960
ctggcgaaaa tcacctcact gattacgatc ctggatgaca ttttgatga ctacgctacc    1020 ttcgaacagc tgaaatgcat tcgtgacgcg atcttcaaag ctgggatgt tagtattatc    1080 gaaaacatcc cgaacaattg aaacgctgt gtggaatttg ttttcaaaac gattcatcag    1140
ctgaccatcg acgctacgga ttatcaaggt cgtgacatga tgccgtttgt cagcaaagca    1200
tgggaagatt atgtggaagc ctgtttcgaa caggcacgct ggaaactgaa aggctacttt    1260
ccgacctata cgaatacat aaaatcgcc ggtaaatgcg ttggctttgg tccgttctcc    1320
ctgcactcag ccattctggc atctccgaat ctgtgtgatg acgatatcca gaaaatctac    1380
ctggataaaa gtcgtttcta ccaactgatg cgtgtcgcga tgcgcctgat tgacgatatc    1440 catgatttg aagaagaacg cctgcacggc aaaatggcct cggcaattag ctgctatatg    1500
```

```
gccgatcatc cgaactgtag cgaaaaagaa gcaatgaatc acattatcga actgaacaat    1560
gaagtgctga agaactgac ccgtgaattt ctgaaaccgt cgatgatctt ccatgaatgg     1620
gaaaaaatct tcgttaacag cacgcgcggt gtccagtttt tctatgtgca cggcgacggt    1680
ttcacctaca cgcataaaga aatcaaacac caaatcctga aaattatcgt tgatccgatt    1740
aaaatctaa                                                            1749

<210> SEQ ID NO 18
<211> LENGTH: 1749
<212> TYPE: DNA
<213> ORGANISM: artificial sequence
<220> FEATURE:
<223> OTHER INFORMATION: codon optimised cDNA sequence

<400> SEQUENCE: 18
atgtctaatt tgatgggtga tcacatttcg agcctgagca gcattccgag caacgcattc      60
aatcagtggg atgacgcatt catccagtcg atggaaaccc cgtatggtga gccggagtac    120
cgtgagcgtg cggaaaccct ggcaaaagaa atcaagattt ttctgaaaga catgcagagc    180
ggcggcggcg atggcgatct gatcgagcgt ttggaaatcg tggatgcgct gcaatgcctg    240
ggtatcgacc gttacttcca agccgagatc aaagctgccc tggactacgt ttataattgt    300
tgggacgagt ctgttggcat tggtctgggt agccagagcg ccactaaaga tctgaacgca    360
acggcgctgg cgctccgtgt tttccgcttg aaccgttacg acgtcagcgc ggacaccttca    420 aagtatttca agataacaa cggtcgtttt gtgctgtgtg cgataataa agacaacaat      480 gacgaagata cagcaaaga gaaaaagtc atgcgcagca tgctgaattt gctgcgtctg     540
agcagcctgg cgtttcctgc tgagattgtc atggaagaag caaaggcctt tagctctcgt    600
tatctgaaag aactgctggg taagagcggc gataccagca aaaagtcgtt tttgaaagaa     660
gtggagtacg cactgattta tgagtggccg cgtaccttca tccgctggga ggcacgcaac    720
tttatcgaga tctacgaact ggacaacgaa cgcctgaaag aaaagcgtat cttgaactg     780 gcgaaactgg acttcaacat tctgcagttc cactataaac tggagatgaa gaatttgtcc    840
tcctggtggg tggagtccga gatcagcaag ctgattgcga cgcgtgagcg tagcattgag    900
tatctgctgt gggctattag cagcatggac gaactggagc actccagcag ccgtatcgcc    960
ctggcgaaga ttcctctct gattaccatt ctggatgata ttttgacga ctacgcgacc    1020 tttgagcaac tgaagtgcat ccgcgacgcc atcttcaagg gctggatgt tagcatcatt    1080 gagaacatcc gaacaattg aaacgttgt gttgaatttg tcttaagac gattcatcaa     1140 ctgaccatcg acgctacgga ctaccagggt cgcgacatga tgccgttcgt gagcaaagcg    1200
tgggaagatt atgttgaggc gtgcttcgag caagcgcgtt ggaagctgaa gggttacttt    1260
ccgacgtaca acgaatacat caagatcgcg ggtaaatgcg tcggtttcgg tccattctcc    1320
cttcatagcg cgattttggc gagcccgaac ctgtgcgatg acgacatcca aaagatctat    1380
ctggataaga gccgttttta tcaattgatg cgcgtcgcga tgcgtctgat tgacgacatt    1440
cacgactttg aagaggaacg cctgcacggt aaaatggcct ccgcgatcag ctgctacatg    1500
gcagatcacc cgaactgttc agagaaagag gcaatgaacc acattattga gttgaataat    1560
gaagtcctga agaactgac ccgtgagttc ctgaaaccga gcatgatctt ccatgagtgg    1620
gaaaagatct tgtgaatag cacgcgcggt gtgcaattct tttacgttca cggcgatggc    1680
ttcacctaca cgcataaaga aatcaagcat cagattctga agattatcgt ggacccgatt    1740
aagatttaa                                                           1749
```

<210> SEQ ID NO 19
<211> LENGTH: 1731
<212> TYPE: DNA
<213> ORGANISM: artificial sequence
<220> FEATURE:
<223> OTHER INFORMATION: codon optimised cDNA sequence

<400> SEQUENCE: 19

| | | | | | |
|---|---|---|---|---|---|
| atgagcaccc | tggaaggcga | caacatctac | agcgtgagca | gcctgccggc | gcacgcgttc | 60 |
| aacgagtggg | aagatgcgag | cgttcagagc | atggagatga | gctacggtga | accggaatat | 120 |
| cgtgagcgtg | cggaaaccct | ggtgaaggaa | gttaaaatcc | tgctgaagga | gatgcacacc | 180 |
| ggtgacggcg | atctgattga | gcgtctggaa | atggtggacg | cgctgcaatg | cctgggcatc | 240 |
| taccgttatt | ttcaggcgga | aattaaacaa | gcgctggact | acgtgtatag | ctgctgggat | 300 |
| ggcaacgttg | gtatcggtct | gggtagcgag | agcccgaccc | agcacctgaa | cgcgaccgcg | 360 |
| ctgggtattc | gtgtgctgcg | tctgcaccgt | tacgacgtta | gcgcggatac | cctgaagaac | 420 |
| ttcaaggata | aaaacggtca | atttgtgctg | tgcggtggca | caacgacaa | caacgatgag | 480 |
| gaagagaaag | ttatgcgtag | catgctgaac | ctgttccgtc | tgagcagcgt | ggcgatcccg | 540 |
| ggtgaaatgg | ttctggaaga | ggcgaaggcg | tttagcagcc | gttatctgaa | agagctgctg | 600 |
| gaaaacagcg | gtgacaccgt | gaagcgtagc | ttcatcaaag | aggttaaata | cgcgctgacc | 660 |
| tatgagtggc | cgattacctt | cgatcgttgg | gaagcgctga | actttatcga | gatttacgac | 720 |
| ctgaacaacg | aacgtctgat | ggataagcgt | atcctggagc | tggcgaaaact | gaacttcaac | 780 |
| attctgcagt | ttcaatataa | gctggaaatg | aaaaacctga | gctcctggtg | ggcgaagagc | 840 |
| ggcatcagca | aactgctggc | ggttcgtgag | cgtagcatcg | aatacctgtt | ttgggcgatt | 900 |
| accagcgtgg | aagagctgga | gctgagcagc | agccgtatcg | cgctggttaa | gtgcaccacc | 960 |
| gtgatcacca | ttgttgacga | tatttcgac | gattatgcga | cctttgaaca | gctgcaatgc | 1020 |
| atcaccgacg | cgattagcaa | agactgggat | gtgagcctgc | tggagaacat | cccgagcaac | 1080 |
| ctgaagacca | gcctggaatt | cgttagcaaa | accattcacg | agctggcgat | ggacgcgacc | 1140 |
| aagtaccagg | tcgtgatat | gatgccgttt | gtgaccaaag | cgtggctgga | ttacaccaac | 1200 |
| gcgtgcttcg | agcaagcgcg | ttggaaggtg | accggctatt | ttccgagcta | caacgaatat | 1260 |
| atcaaagcgg | ggagctgag | cgttgcgttc | ggtccgatcc | tgctgcacac | cgcgctggcg | 1320 |
| gcgagcccga | ttctgtgcga | cgaggatatc | gaaaagattt | acctggacaa | agccgtttc | 1380 |
| tatcacatca | tgcgtgttag | catgcgtctg | accgacgata | ttcacgactt | tgaggatgaa | 1440 |
| cgtctgcacg | gcaagatggc | gagcgcgatt | agctgctaca | aggtgatca | cccgaactgc | 1500 |
| agcgaagagg | aagcgatcaa | caacattgtg | accctgaaca | acgagctgct | gaaggaaatg | 1560 |
| atccgtgagt | tctttaaacc | gaacagccac | tatctggagt | gggaaaagat | tgcgttaac | 1620 |
| agcacccgtg | gcatcggttt | cttttacatt | ttcggcgacg | gttttaccta | tagccacaag | 1680 |
| gagatcaaag | aacagatttt | caagatcatt | gtgaacccga | tcaaagttta | a | 1731 |

<210> SEQ ID NO 20
<211> LENGTH: 19
<212> TYPE: DNA
<213> ORGANISM: artificial sequence
<220> FEATURE:
<223> OTHER INFORMATION: primer sequence

<400> SEQUENCE: 20

```
tttaagtgct tctgcgatg                                              19
```

<210> SEQ ID NO 21
<211> LENGTH: 19
<212> TYPE: DNA
<213> ORGANISM: artificial sequence
<220> FEATURE:
<223> OTHER INFORMATION: primer sequence

<400> SEQUENCE: 21

```
acatctaggt ttgtgcctt                                              19
```

<210> SEQ ID NO 22
<211> LENGTH: 18
<212> TYPE: DNA
<213> ORGANISM: artificial sequence
<220> FEATURE:
<223> OTHER INFORMATION: primer sequence

<400> SEQUENCE: 22

```
atcgccatct ccagtgtg                                               18
```

<210> SEQ ID NO 23
<211> LENGTH: 19
<212> TYPE: DNA
<213> ORGANISM: artificial sequence
<220> FEATURE:
<223> OTHER INFORMATION: primer sequence

<400> SEQUENCE: 23

```
ctttagtgct tctgtgatg                                              19
```

<210> SEQ ID NO 24
<211> LENGTH: 19
<212> TYPE: DNA
<213> ORGANISM: artificial sequence
<220> FEATURE:
<223> OTHER INFORMATION: primer sequence

<400> SEQUENCE: 24

```
catacaagtt tgtgcctca                                              19
```